US010300073B2

(12) United States Patent
Haudenschild et al.

(10) Patent No.: US 10,300,073 B2
(45) Date of Patent: May 28, 2019

(54) USE OF CDK9 AND BRD4 INHIBITORS TO INHIBIT INFLAMMATION

(71) Applicant: The Regents of the University of California, Oakland, CA (US)

(72) Inventors: Dominik Haudenschild, Davis, CA (US); Jasper Yik, Elk Grove, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/517,476

(22) PCT Filed: Oct. 13, 2015

(86) PCT No.: PCT/US2015/055394
§ 371 (c)(1),
(2) Date: Apr. 6, 2017

(87) PCT Pub. No.: WO2016/061144
PCT Pub. Date: Apr. 21, 2016

(65) Prior Publication Data
US 2017/0304315 A1    Oct. 26, 2017

Related U.S. Application Data

(60) Provisional application No. 62/063,839, filed on Oct. 14, 2014.

(51) Int. Cl.
A61K 31/00      (2006.01)
A61K 45/06      (2006.01)
A61K 31/352     (2006.01)
A61K 31/445     (2006.01)
A61K 31/551     (2006.01)
A61K 31/5513    (2006.01)

(52) U.S. Cl.
CPC ........ A61K 31/5513 (2013.01); A61K 31/352 (2013.01); A61K 31/445 (2013.01); A61K 31/551 (2013.01); A61K 45/06 (2013.01); A61K 31/00 (2013.01)

(58) Field of Classification Search
CPC ................ A61K 31/352; A61K 31/551; A61K 31/5513; A61K 2300/00
See application file for complete search history.

(56) References Cited

U.S. PATENT DOCUMENTS

| 6,660,750 B2 | 12/2003 | Price et al. |
| 9,498,471 B2 | 11/2016 | Haudenschild et al. |
| 2005/0025765 A1 | 2/2005 | Dimauro et al. |
| 2006/0264628 A1 | 11/2006 | McInnes et al. |
| 2007/0021419 A1 | 1/2007 | Wang et al. |
| 2007/0021452 A1 | 1/2007 | Wang et al. |
| 2007/0072882 A1 | 3/2007 | Guzi et al. |
| 2007/0225270 A1 | 9/2007 | Guzi et al. |
| 2007/0275963 A1 | 11/2007 | Guzi et al. |
| 2008/0125404 A1 | 5/2008 | Benigni et al. |
| 2009/0012082 A1 | 1/2009 | Guicherit et al. |
| 2009/0137572 A1 | 5/2009 | Wang et al. |
| 2009/0162376 A1 | 6/2009 | Brown et al. |
| 2009/0215805 A1 | 8/2009 | Wood et al. |
| 2009/0258886 A1 | 10/2009 | Blanchard et al. |
| 2009/0270427 A1 | 10/2009 | Fisher et al. |
| 2009/0318441 A1 | 12/2009 | Brain et al. |
| 2009/0318446 A1 | 12/2009 | Fisher et al. |
| 2009/0325983 A1 | 12/2009 | Fisher et al. |
| 2010/0003246 A1 | 1/2010 | Hunag et al. |
| 2010/0035870 A1 | 2/2010 | Jones et al. |
| 2010/0076000 A1 | 3/2010 | Lucking et al. |
| 2010/0160350 A1 | 6/2010 | Kluge |
| 2010/0249149 A1 | 9/2010 | Allgeier et al. |
| 2012/0142680 A1 | 6/2012 | Blanchard et al. |
| 2012/0196855 A1 | 8/2012 | Blanchard et al. |
| 2012/0225899 A1 | 9/2012 | Costales et al. |
| 2015/0105423 A1 | 4/2015 | Haudenschild et al. |
| 2015/0148344 A1* | 5/2015 | Babaoglu ............ C07D 413/04 514/235.2 |
| 2017/0246156 A1 | 8/2017 | Haudenschild et al. |

FOREIGN PATENT DOCUMENTS

| WO | WO 2006/021803 A2 | 3/2006 |
| WO | WO 2006/024858 A1 | 3/2006 |
| WO | WO 2007/117653 A2 | 10/2007 |
| WO | WO 2008/079933 A2 | 7/2008 |

(Continued)

OTHER PUBLICATIONS

Maturitas 78 (2014) 188-198.*
Sokolove et al. (Ther Adv Musculoskelet Dis. Apr. 2013; 5(2): 77-94).*
U.S. Office Action dated Feb. 27, 2015 issued in U.S. Appl. No. 14/351,878.
U.S. Final Office Action dated Aug. 21, 2015 issued in U.S. Appl. No. 14/351,878.
U.S. Notice of Allowance dated Jul. 15, 2016 issued in U.S. Appl. No. 14/351,878.
U.S. Notice of Allowance dated Jul. 28, 2016 issued in U.S. Appl. No. 14/351,878.
U.S. Office Action dated Jun. 9, 2017 issued in U.S. Appl. No. 15/356,231.
PCT International Search Report dated Mar. 28, 2013 issued in Application No. PCT/US2012/061079.

(Continued)

Primary Examiner — Shirley V Gembeh
(74) Attorney, Agent, or Firm — Mintz, Levin, Cohn, Ferris, Glovsky and Popeo, P.C.

(57) ABSTRACT

Provided are methods for the combined use of cyclin-dependent kinase 9 (CDK9) inhibitors and bromodomain containing 4 (BRD4) inhibitors to reduce, inhibit and/or prevent cartilage degradation and systemic traumatic inflammation. A combination of CDK9 inhibitors and BRD4 inhibitors can be used to reduce, inhibit and/or prevent cartilage degradation and loss of cartilage viability during allograft storage. A combination of CDK9 inhibitors and BRD4 inhibitors can be used as a post-injury intervention treatment to reduce, inhibit and/or prevent the acute cellular responses that lead to future cartilage degradation and osteoarthritis.

27 Claims, 18 Drawing Sheets

(56) References Cited

FOREIGN PATENT DOCUMENTS

| WO | WO 2008/129080 A1 | 10/2008 |
|---|---|---|
| WO | WO 2010/020675 A1 | 2/2010 |
| WO | WO 2011/012661 A1 | 2/2011 |
| WO | WO 2011/077171 A1 | 6/2011 |
| WO | WO 2012/066065 A1 | 5/2012 |
| WO | WO 2012/066070 A1 | 5/2012 |
| WO | WO 2012/1101063 A1 | 8/2012 |
| WO | WO 2012/1101064 A1 | 8/2012 |
| WO | WO 2012/1101065 A2 | 8/2012 |
| WO | WO 2012/1101066 A1 | 8/2012 |
| WO | WO 2013/059634 A1 | 4/2013 |
| WO | WO 2016/061144 A1 | 4/2016 |

OTHER PUBLICATIONS

PCT Written Opinion dated Mar. 28, 2013 issued in Application No. PCT/US2012/061079.

PCT International Preliminary Report on Patentability and Written Opinion dated May 1, 2014 issued in Application No. PCT/US2012/061079.

PCT International Search Report and Written Opinion dated Jan. 12, 2016 issued in Application No. PCT/US15/55394.

PCT International Preliminary Report on Patentability and Written Opinion dated Apr. 18, 2017 issued in Application No. PCT/US15/55394.

Anderson et al., (Jun. 2011) "Post-Traumatic Osteoarthritis: Improved Understanding and Opportunities for Early Intervention," *Journal of Orthopaedic Research*, 29:802-809.

Byrd et al., (2007) "Flavopiridol administered using a pharmacologically derived schedule is associated with marked clinical efficacy in refractory, genetically high-risk chronic lymphocytic leukemia," *Blood Journal*, 109(2):399-404.

Christiansen, B.A. et al., (Oct. 2015) "Non-invasive mouse models of post-traumatic osteoarthritis," *Osteoarthritis Cartilage*, 23(10):1627-1638. [Epub May 21, 2015, Abstract Only], 2pp.

Chu et al., (2014) "Osteoarthritis: From Palliation to Prevention," *J Bone Joint Surg Am*, 96(e130):1-9.

Craft et al., (2015) "Physical Examination and Imaging of Medial Collateral Ligament and Posteromedial Corner of the Knee," *Sports Med Arthrosc Rev*, 23(2):e1-e6.

De Falco, Giulia et al., (1998) "CDK9 (PITALRE): A Multifunctional cdc2-Related Kinase," *Journal of Cellular Physiology*, 177:501-506.

Fanelli et al., (Jun. 2015) "Management of Chronic Combined PCL Medial Posteromedial Instability of the Knee," *Sports Med Arthrosc Rev*, 23(2):96-103.

Felson, D.T. (2013) "Osteoarthritis as a disease of mechanics," *Osteoarthritis and Cartilage*, 21:10-15.

Fukui et al., (2014) "The Analysis of the Effect of JQ1 and Flavopiridol on Chondrocytes under Inflammatory Stimuli," *Orthopaedic Research Society (ORS) 2014 Annual Meeting*, Mar. 15-18, 2014, 3pp.

Haudenschild, Dominik R., (2014) "Reply to the Editor," *Arthritis Rhemuamtol Letters*, p. 3526.

Haudenschild, Dominik R., (Oct. 2013) "Early Intervention with Cdk9 Inhibitors to Prevent Post-Traumatic Osteoarthritis," *Annual Report*, OMB No. 0704-0188, pp. 1-136, 8pp.

Heard et al., (2013) "Changes of early post-traumatic osteoarthritis in an ovine model of simulated ACL reconstruction are associated with transient acute post-injury synovial inflammation and tissue catabolism," *Osteoarthritis and Cartilage*, 21:1942-1949.

Hu et al., (Feb. 11, 2016) "Inhibition of CDK9 prevents mechanical injury-induced inflammation, apoptosis and matrix degradation in cartilage explants," *Eur Cell Mater.*, 30:200-209.

Krystof et al., (2012) "Perspective of Cyclin-dependent kinase 9 (CDK9) as a Drug Target," *Current Pharmaceutical Design*, 18(20):2883-2890.

Németh et al., (2011) "Novel, selective CDK9 inhibitors for the treatment of HIV infection," *Current Medical Chemistry*, 18(3):342-358. [Abstract Only], 2pp.

Nowicki et al., (Oct. 29, 2010) "CDK9 Inhibitors Push Cancer Cells over the Edge," *Chemistry & Biology*, 17:1047-1048.

Pelletier et al. (Jun. 2001) "Osteoarthritis, an Inflammatory Disease: Potential Implication for the Selection of New Therapeutic Targets," *Arthritis & Rheumatism*, 44(6):1237-1247.

Polier et al., (2011) "Wogonin and related natural flavones are inhibitors of CDK9 that induce apoptosis in cancer cells by transcriptional suppression of Mcl-1," *Cell Death and Disease*, 2:e182, 10pp.

Phelps et al., (Mar. 19, 2009) "Clinical response and pharmacokinetics from a phase 1 study of an active dosing schedule of flavopiridol in relapsed chronic lymphocytic leukemia," *Blood Journal* 113(12):2637-2645.

Ramaswamy et al., (2012) "A dose-finding, pharmacokinetic and pharmacodynamic study of a novel schedule of flavopiridol in patients with advanced solid tumors," *Invest New Drugs* 30(2):629-638 [Abstract Only].

Schmerwitz et al., (2011) "Flavopiridol Protects Against Inflammation by Attenuating Leukocyte-Endothelial Interaction via Inhibition of Cyclin-Dependent Kinase 9," *Arterioscler Thromb Vasc Biol*, 31:280-288.

Schmerwitz et al., (2010) "Novel mechanisms of flavopiridol: protection against inflammation-induced endothelium-leukocyte interactions in vivo and in vitro," *Dissertation zur Erlangung des Doktorgrades der Fakultät für Chemie und Pharmazie der Ludwig-Maximilians-Universität München* pp. 1-113.

Sekine et al., (2008) "Successful Treatment of Animal Models of Rheumatoid Arthritis with Small-Molecule Cyclin-Dependent Kinase Inhibitors," *The Journal of Immunology*, 180:1954-1961.

Szczodry et al., (2009) "Progressive Chondrocyte Death After Impact Injury Indicates a Need for Chondroprotective Therapy," *Am J Sports Med.*, 37(12):2318-2322.

Tam et al., (Sep. 2007) "In Vitro Model of Full-Thickness Cartilage Defect Healing," *Journal of Orthopedic Research*, 25:1136-1144.

Tsuchida et al., (2014) "Cytokine profiles in the joint depend on pathology, but are different between synovial fluid, cartilage tissue and cultured chondrocytes," *Arthritis Research & Therapy*, 16(441):1-15.

Wassilew et al., (2010) "The expression of proinflammatory cytokines and matrix metalloproteinases in the synovial membranes of patients with osteoarthritis compared with traumatic knee disorders," *Arthroscopy*, 26(8):1096-1104. [Abstract Only], 2pp.

Wen et al., (2014) "Does post-injury ACL reconstruction prevent future OA?" *Nature Reviews Rheumatology*, 10:577-578.

Yik et al., (Oct. 21, 2011) "Discoveries in Molecular and Biomechanical Research," *Research Symposium 2011*, The Lawrence J. Ellison Musculoskeletal Research Center, Department of Orthopaedic Surgery, University of California, Davis School of Medicine, pp. 1-28.

Yik, et al., (2012) "The cdk9 inhibitor flavopiridol effectively suppresses the activation of primary inflammatory response genes in human articular chondrocytes," *Orthopaedic Research Society (ORS) 2012 meeting*, Feb. 4-7, 2012, one page.

Yik et al., (Jun. 2014) "Cyclin-Dependent Kinase 9 Inhibition Protects Cartilage From the Catabolic Effects of Proinflammatory Cytokines," *Arthritis & Rheumatology* 66(6):1537-1546.

BRD4—Wikipedia, retrieved from the Internet: URL:http://en.wikipedia.org/wiki/BRD4 [retrieved on Nov. 26, 2018].

JQ1—Wikipedia, retrieved from the Internet: URL:http://en.wikipedia.org/wiki/JQ1 [retrieved on Nov. 26, 2018].

I-BET762>98% (HPLC), Sigma Aldrich, retrieved from the Internet: URL:https://www.sigmaaldrich.com/catalog/product/sigma/sml1272?lang=en&region=US [retrieved on Nov. 26, 2018].

Fukui et al., The in vivo and in vitro effect of inhibitors of BRD4 and CDK4 on early phase of post traumatic osteoarthritis, Osteoarthritis and Cartilage, 23 (Jan. 1, 2015) A82-A416.

\* cited by examiner

Flavopiridol – Targets Cdk9

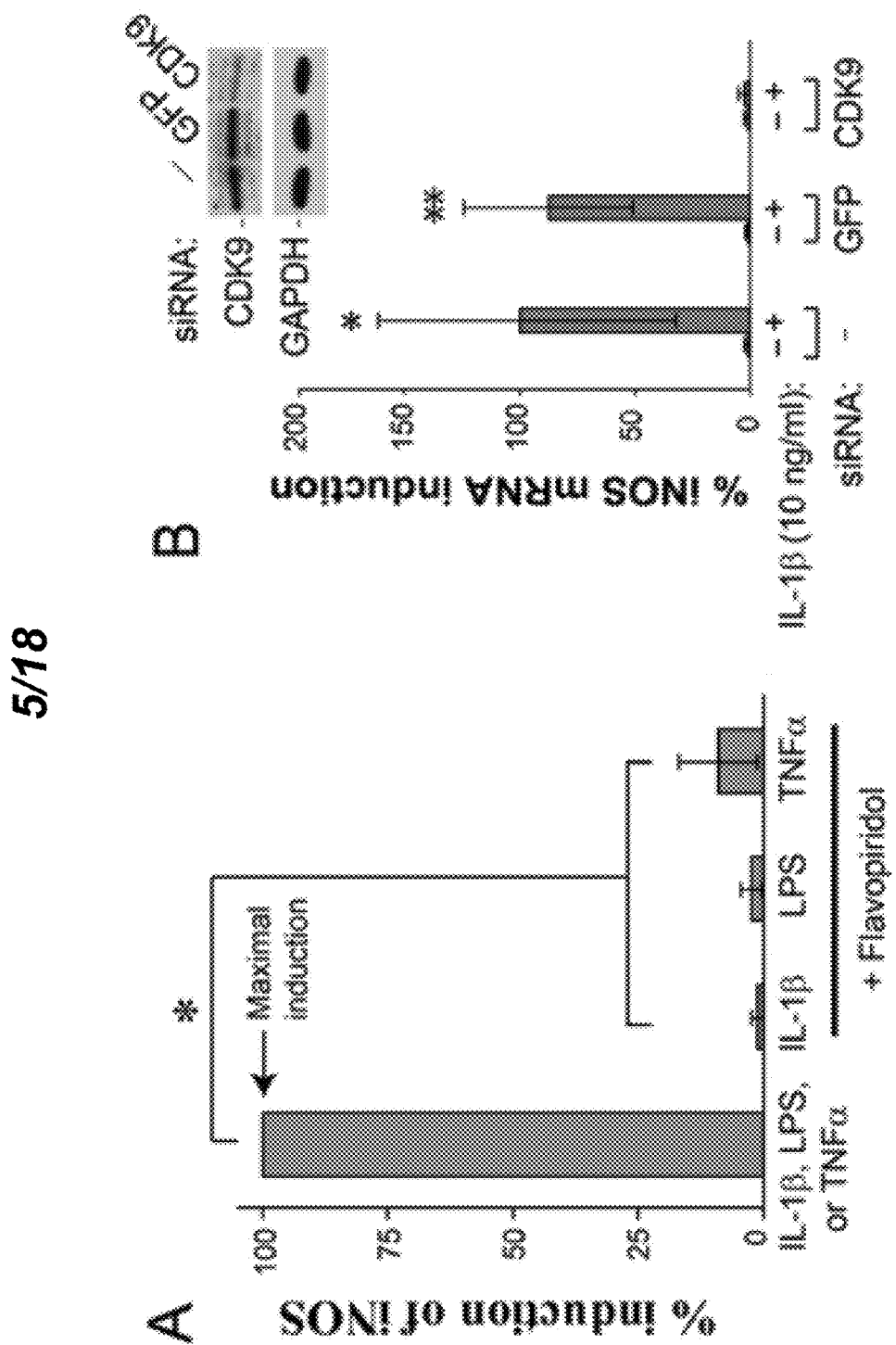
Figure 5A-B

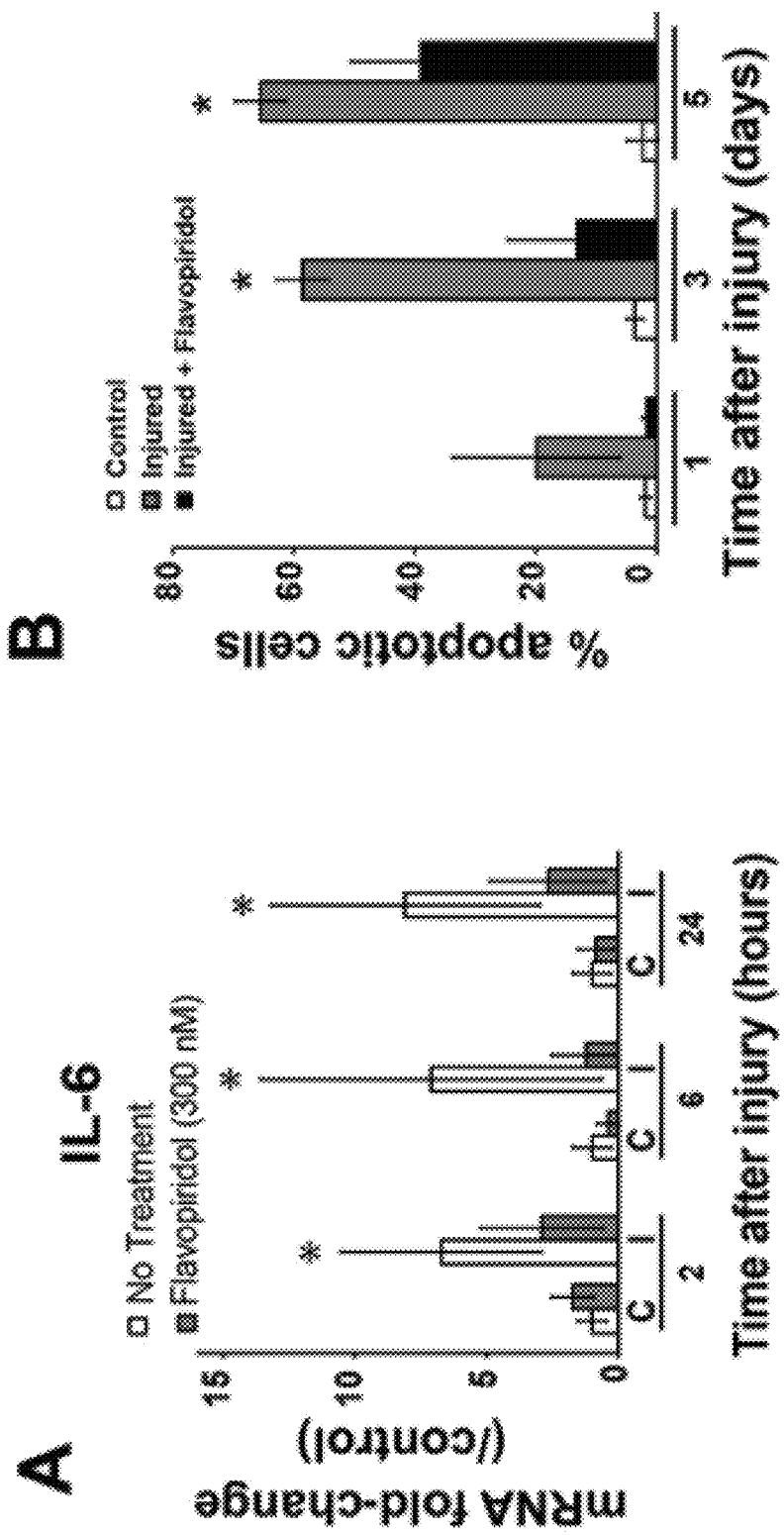
Figure 6A-B

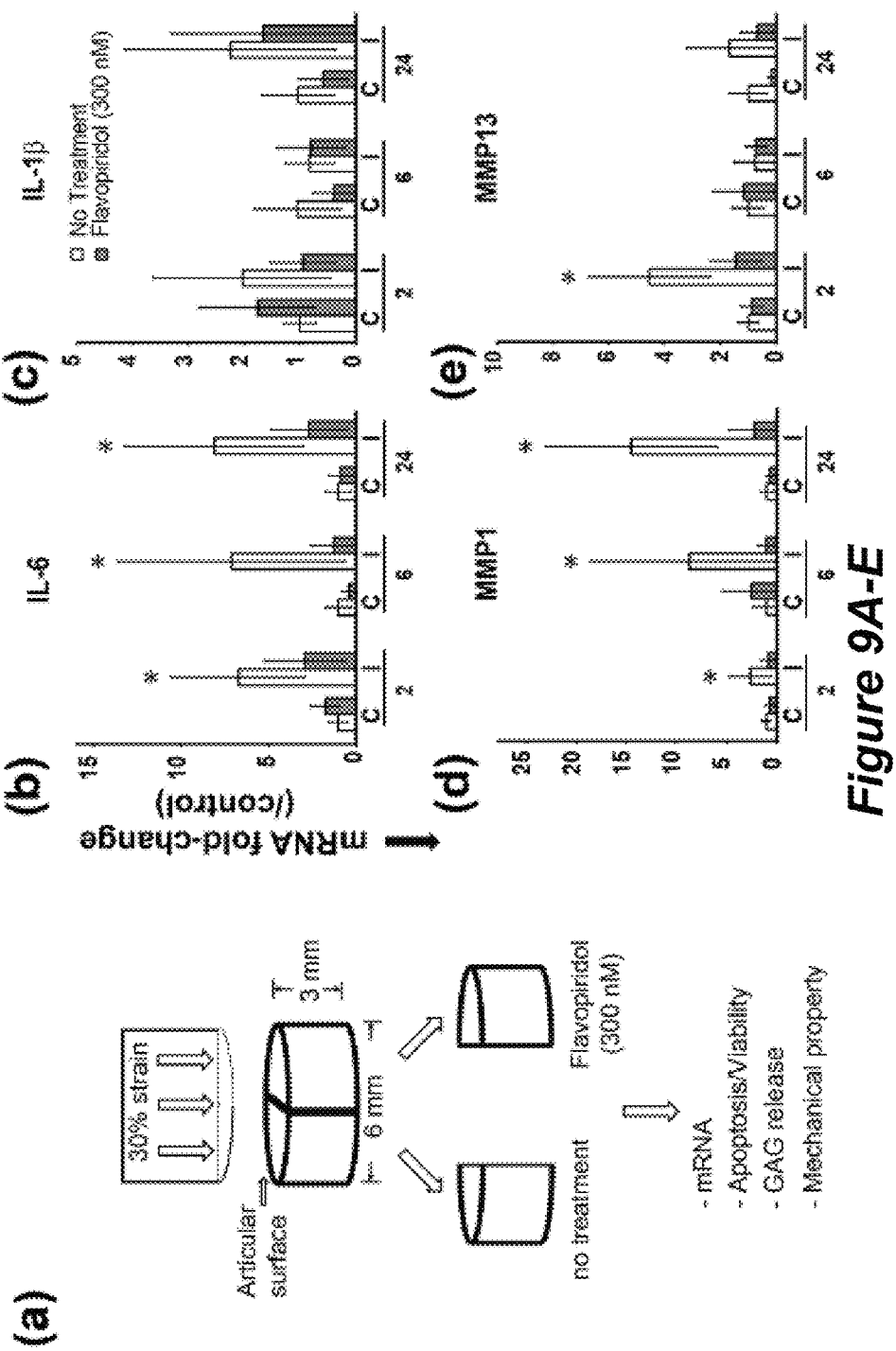
Figure 9A-E

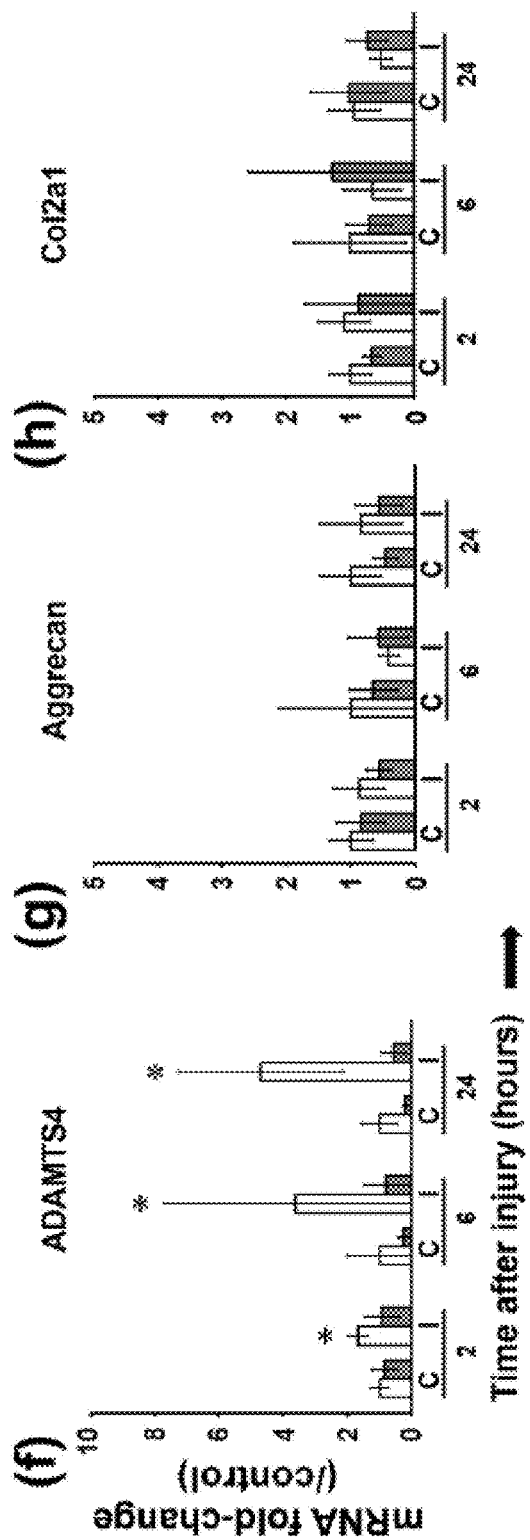
Figure 9F-G

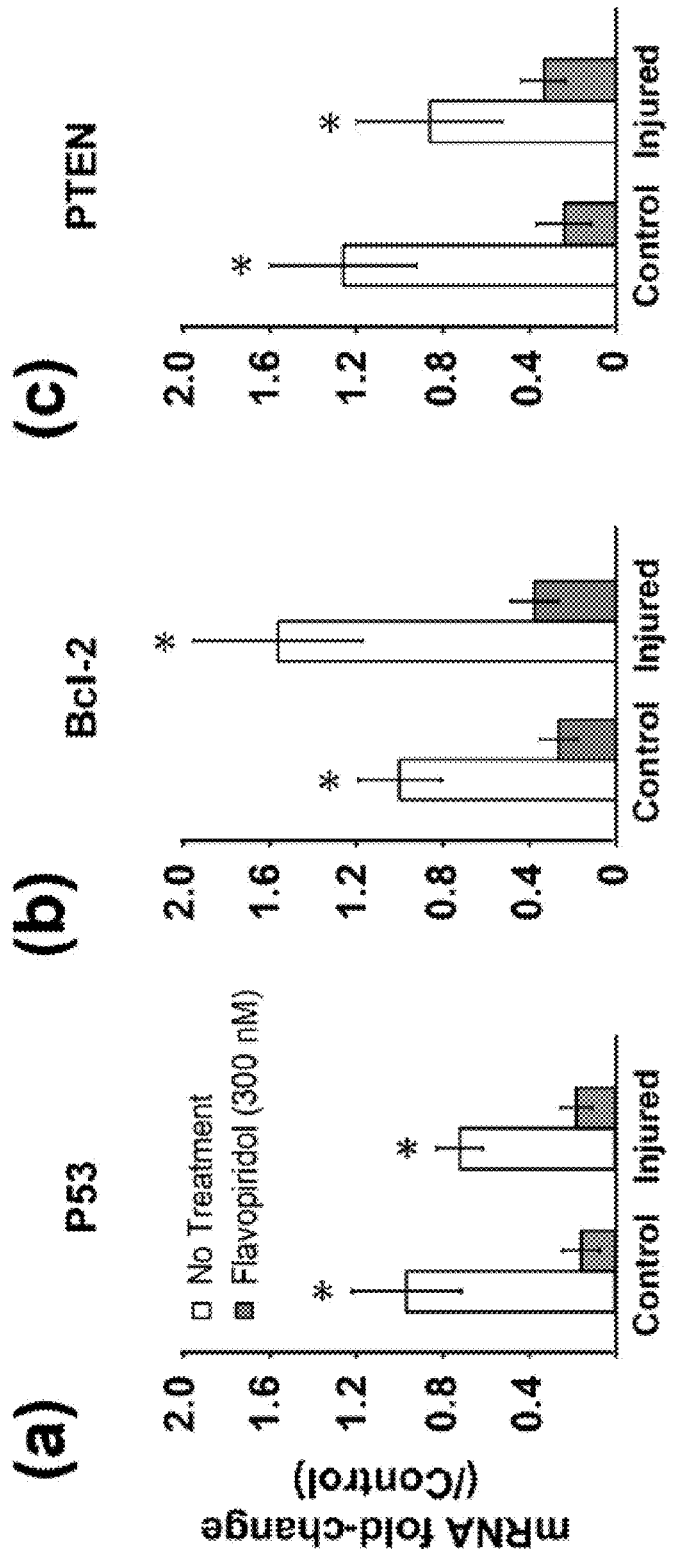
Figure 10A-C

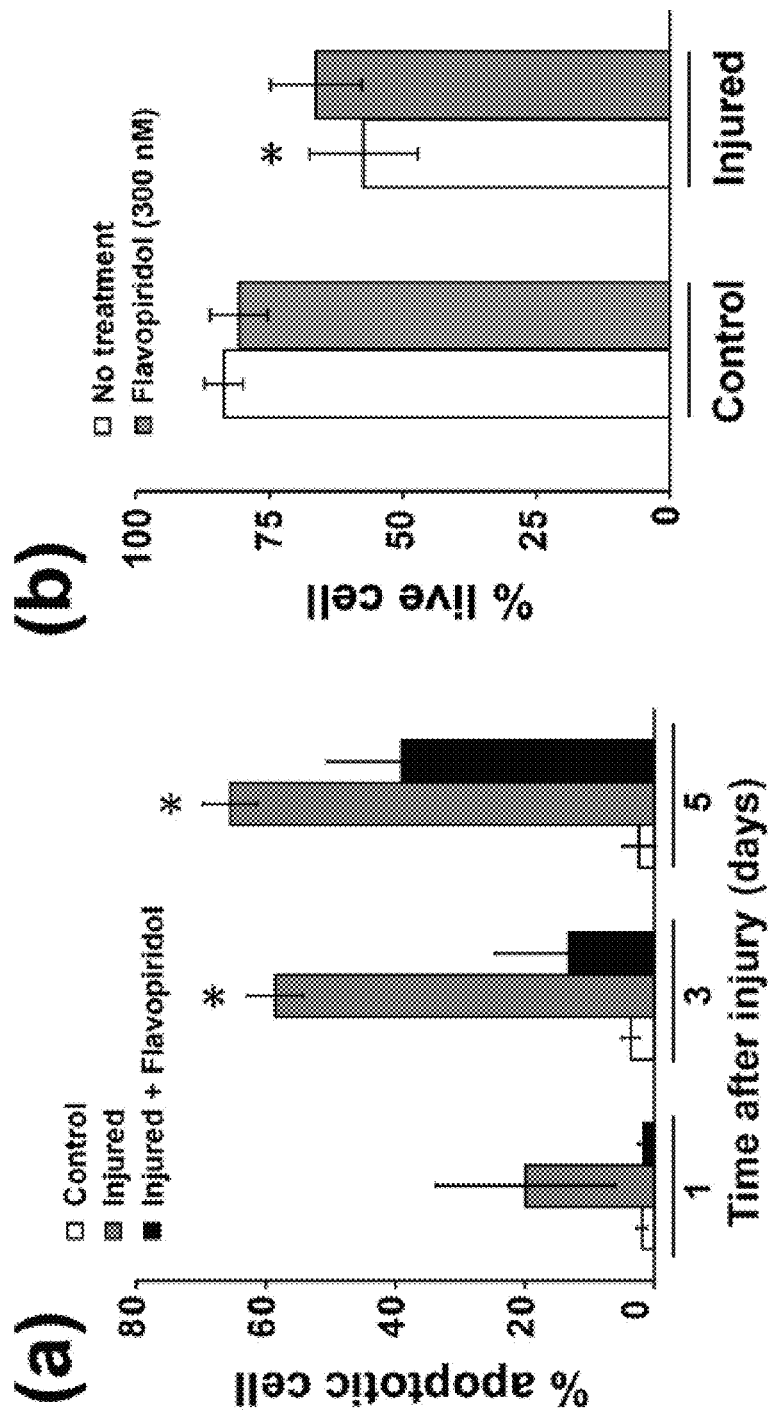
*Figure 11A-B*

USE OF CDK9 AND BRD4 INHIBITORS TO INHIBIT INFLAMMATION

CROSS-REFERENCE TO RELATED APPLICATIONS

This application is the U.S. national phase under 35 U.S.C. § 371 of Intl. Appl. No. PCT/US2015/055394, filed on Oct. 13, 2015, which claims the benefit under 35 U.S.C. 119(e) of U.S. Provisional Appl. No. 62/063,839, filed on Oct. 14, 2014, which are hereby incorporated herein by reference in their entireties for all purposes.

STATEMENT OF GOVERNMENTAL SUPPORT

This invention was made with government support under Grant No. AR063348 awarded by the National Institutes of Health and Grant No. W81XWH-12-1-0311 awarded by the Department of Defense. The government has certain rights in the invention.

FIELD

Provided are methods for the combined use of cyclin-dependent kinase 9 (CDK9) inhibitors and bromodomain containing 4 (BRD4) inhibitors to reduce, inhibit and/or prevent cartilage degradation and systemic traumatic inflammation. A combination of CDK9 inhibitors and BRD4 inhibitors can be used to reduce, inhibit and/or prevent cartilage degradation and loss of cartilage viability during allograft storage. A combination of CDK9 inhibitors and BRD4 inhibitors can be used as a post-injury intervention treatment to reduce, inhibit and/or prevent the acute cellular responses that lead to future cartilage degradation and osteoarthritis.

BACKGROUND

A host of pro-inflammatory and cellular stress induces inflammatory response in chondrocytes, leading to upregulation of matrix metalloproteinases (MMPs) and aggrecanases that degrade the cartilage matrix. Chronic deregulation of these catabolic pathways is suspected of causing osteoarthritis. Regardless of the sources of inflammation, the downstream signals all converge on a common mechanism that activates transcription of all primary response genes. This regulatory point is controlled by the transcription factor cyclin-dependent kinase 9 (CDK9) and its T-type cyclin partner. It was believed for many years that the rate-limiting step in transcriptional activation is the recruitment of transcription factors and RNA Polymerase II (Pol II) to gene promoters. However, recent studies on primary response genes have shown that in their basal and unstimulated states, Pol II is already pre-assembled but is paused at the promoters (Hargreaves, et al., *Cell* 2009, 138:129-45; Zippo, et al., *Cell* 2009, 138:1122-36). The rapid activation of these genes is the result of signal-induced recruitment of CDK9 to the promoters, where it phosphorylates Pol II. Phosphorylation by CDK9 induces a conformational change that allows Pol II to enter possessive elongation to efficiently transcribe full-length mRNAs (Zhou and Yik, *MMBR* 2006, 70(3): 646-659). Given that CDK9 controls a common mechanism of transcriptional activation of inducible genes, it is an effective target for inhibiting the undesirable inflammatory responses from diverse cellular stress, such as sports-related injuries. The present invention is based, in part, on the discovery that pharmacological CDK9 inhibitors, e.g., flavopiridol, and analogs and salts thereof, can effectively suppress primary inflammatory genes in human articular chondrocytes in vitro. Effective suppression of inflammatory responses allows for longer storage life for osteochondral explants used commonly in cartilage repair, and also has therapeutic implications in preventing cartilage breakdown in post-traumatic osteoarthritis.

Severe combat trauma such as those received from explosive devices cause devastating damage to the human body, resulting in dramatic tissue loss, burns, orthopaedic injuries, and hemorrhagic shock. The reaction to such severe polytrauma can include a whole body response called systemic inflammatory response syndrome (SIRS). SIRS is the results of an exaggerated production of pro-inflammatory cytokines that illicit an overwhelming inflammatory response throughout the entire body. While a controlled local inflammation facilitates wound healing, the overwhelming inflammatory response of SIRS significantly increases the risk of life-threatening events such as multiple organ dysfunction and failure. Surgical treatment of injuries is often delayed after polytrauma due to the risk of SIRS-induced organ failure or death. This delays recovery and increases associated medical costs. No pharmacologic agents effectively prevent the onset of SIRS or significantly improve its outcome; there is an urgent need to develop such drugs. Current anti-inflammatory treatments are ineffective in part because they target individual cytokines and pathways, but in SIRS there are simply too many cytokines and pathways involved.

Since the problems of SIRS stem from the activation of the inflammatory response, the conventional approaches to prevent SIRS have targeted one or several of the many individual inflammatory signals or pathways. The results from these studies are mostly disappointing. Severe traumatic injuries activate too many inflammatory signals and pathways, with significant cross talk between the pathways, for this one-by-one approach to be effective. The diverse inflammatory signals propagate through dozens of different cell surface receptors and an intricate network of intracellular signaling pathways, which are then transmitted into the cell nucleus for the activation of thousands of inflammatory mediator genes. To make matters worse, the inflammatory receptors and signaling pathways have multiple levels of redundancy and cross talk. Therefore, no single agent that targets only a specific inflammatory receptor/mediator, signaling pathway, or cell type can prevent SIRS. It is also impractical to formulate a drug cocktail that targets all known inflammatory mediators and pathways at once. In addition, the initial exaggerated pro-inflammatory response in SIRS is activated rapidly after trauma; and therefore, the ideal anti-SIRS agents must also be able to act almost as quickly.

SUMMARY

In one aspect, methods of reducing, preventing, inhibiting, mitigating and/or ameliorating cartilage degradation and/or chondrocyte death in a subject in need thereof are provided. In some embodiments, the methods comprise co-administering to the subject an effective amount of an inhibitor of cyclin-dependent kinase 9 (CDK9) and an inhibitor of bromodomain containing 4 (BRD4), thereby reducing, preventing, inhibiting, mitigating and/or ameliorating cartilage degradation and/or chondrocyte death in the subject. In a further aspect, methods of reducing, preventing, inhibiting, mitigating and/or ameliorating the onset and/or progression of post-traumatic osteoarthritis in a subject in need thereof are provided. In some embodiments, the methods comprise co-administering to the subject an effective amount of an inhibitor of cyclin-dependent kinase 9 (CDK9) and an inhibitor of bromodomain containing 4 (BRD4), thereby reducing, preventing, inhibiting, mitigating and/or ameliorating post-traumatic osteoarthritis in the subject. In varying embodiments, the subject has experienced a traumatic injury to cartilage tissue. In varying embodiments, the traumatic injury induces acute overexpression of primary response genes. In varying embodiments, the subject has undergone joint surgery. In another aspect, provided are methods of reducing, preventing, inhibiting, mitigating and/or ameliorating severe polytrauma or systemic inflammatory response syndrome (SIRS) in a subject in need thereof. In some embodiments, the methods comprise administering to the subject an effective amount of an inhibitor of cyclin-dependent kinase 9 (CDK9), thereby reducing, preventing, inhibiting, mitigating and/or ameliorating severe polytrauma or systemic inflammatory response syndrome (SIRS) in the subject. In a related aspect, provided are methods of reducing, preventing, inhibiting, mitigating and/or ameliorating severe polytrauma or systemic inflammatory response syndrome (SIRS) in a subject in need thereof. In some embodiments the methods comprise co-administering to the subject an effective amount of an inhibitor of cyclin-dependent kinase 9 (CDK9) and an inhibitor of bromodomain containing 4 (BRD4), thereby reducing, preventing, inhibiting, mitigating and/or ameliorating severe polytrauma or systemic inflammatory response syndrome (SIRS) in the subject. In some embodiments, the subject may have experienced a traumatic injury, e.g., leading to acute systemic inflammation and to multiple organ system failure. In varying embodiments, one or both of the inhibitor of CDK9 and the inhibitor of BRD4 are initially co-administered during the acute response phase and reduce and/or inhibit transcriptional activation of one or more primary response genes after experiencing traumatic injury. In some embodiments, the one or more primary response genes are selected from the group consisting of IL-1β, inducible nitric oxide synthase (iNOS), IL-6, TNF-α, MMP-1, MMP-3, MMP-9, MMP-13 and ADAMTS4 (aggrecanase). In varying embodiments, one or both of the inhibitor of CDK9 and the inhibitor of BRD4 are initially co-administered within about 72 hours, about 48 hours, about 24 hours, e.g., within about 22, 20, 18, 16, 14, 12, 10, 8, 6, 4, 2, 1 or fewer hours, after experiencing traumatic injury. In varying embodiments, one or both of the inhibitor of CDK9 and the inhibitor of BRD4 are administered to the subject within about 10 days after damage or injury. In varying embodiments, one or both of the inhibitor of CDK9 and the inhibitor of BRD4 are administered over a course of 10 days. In varying embodiments, one or both of the inhibitor of CDK9 and the inhibitor of BRD4 are administered multiple times. In varying embodiments, one or both of the inhibitor of CDK9 and the inhibitor of BRD4 are administered daily for three consecutive days post-injury. In varying embodiments, the subject has undergone surgery to repair damaged cartilage tissue. In varying embodiments, the subject has received an osteochondral explant. In varying embodiments, the osteochondral explant is a cartilage allograft. In varying embodiments, one or both of the inhibitor of CDK9 and the inhibitor of BRD4 are co-administered concurrently with or prior to surgery. In varying embodiments, one or both of the inhibitor of CDK9 and the inhibitor of BRD4 are initially co-administered within about 72 hours, about 48 hours, about 24 hours, e.g., within about 22, 20, 18, 16, 14, 12, 10, 8, 6, 4, 2, 1 or fewer hours, after surgery. In varying embodiments, one or both of the inhibitor of CDK9 and the inhibitor of BRD4 are co-administered systemically. In varying embodiments, one or both of the inhibitor of CDK9 and the inhibitor of BRD4 are co-administered intravenously. In varying embodiments, one or both of the inhibitor of CDK9 and the inhibitor of BRD4 are co-administered directly to the site of injured cartilage tissue. In varying embodiments, one or both of the inhibitor of CDK9 and the inhibitor of BRD4 are delivered from a matrix. In varying embodiments, the inhibitor of CDK9 is a small organic compound. In varying embodiments, the inhibitor of CDK9 is flavopiridol. In varying embodiments, one of claims 1 to 16, wherein the inhibitor of BRD4 is a small organic compound. In varying embodiments, the inhibitor of BRD4 is selected from JQ1 and GSK525762A. In varying embodiments, one or both of the inhibitor of CDK9 and the inhibitor of BRD4 are administered at a subtherapeutic or non-efficacious dose for the individual inhibitors.

In another aspect, provided are methods of reducing, preventing or inhibiting degradation of an osteochondral explant and/or reducing, preventing or inhibiting chondrocyte death during storage. In some embodiments, the methods comprise storing the osteochondral explant and/or chondrocytes in a solution comprising an inhibitor of cyclin-dependent kinase 9 (CDK9) and an inhibitor of bromodomain containing 4 (BRD4). In varying embodiments, the osteochondral explant is allograft cartilage. In varying embodiments, the inhibitor of CDK9 is a small organic compound. In varying embodiments, the inhibitor of CDK9 is flavopiridol. In varying embodiments, the inhibitor of BRD4 is a small organic compound. In varying embodiments, the inhibitor of BRD4 is selected from JQ1 and GSK525762A. In varying embodiments, the osteochondral explant is submerged in the solution comprising the inhibitor of CDK9 and the inhibitor of BRD4. In varying embodiments, the solution comprises a sub-efficacious amount of one or both of the inhibitor of CDK9 and the inhibitor of BRD4.

In a further aspect, provided are compositions comprising an osteochondral explant in a solution comprising an inhibitor of cyclin-dependent kinase 9 (CDK9) and an inhibitor of bromodomain containing 4 (BRD4). In varying embodiments, the osteochondral explant is allograft cartilage. In varying embodiments, the inhibitor of CDK9 is a small organic compound. In varying embodiments, the inhibitor of CDK9 is flavopiridol. In varying embodiments, the inhibitor of BRD4 is a small organic compound. In varying embodiments, the inhibitor of BRD4 is selected from JQ1 and GSK525762A. In varying embodiments, the osteochondral explant is submerged in the solution comprising the inhibitor of CDK9 and the inhibitor of BRD4. In varying embodiments, the solution comprises a sub-efficacious amount of one or both of the inhibitor of CDK9 and the inhibitor of BRD4. In varying embodiments, the compositions are packaged in a kit.

Definitions

The term "cyclin-dependent kinase 9" or "CDK9" refers to a member of the cyclin-dependent protein kinase (CDK) family. CDK family members are highly similar to the gene products of S. cerevisiae cdc28, and S. pombe cdc2, and known as important cell cycle regulators. CDK9 was found to be a component of the multiprotein complex TAK/P-TEFb, which is an elongation factor for RNA polymerase II-directed transcription and functions by phosphorylating the C-terminal domain of the largest subunit of RNA polymerase II. CDK9 forms a complex with and is regulated by its regulatory subunit cyclin T or cyclin K. HIV-1 Tat protein was found to interact with this protein and cyclin T. Structurally, "CDK9" refers to nucleic acids and polypeptide polymorphic variants, alleles, mutants, and interspecies homologs that: (1) have an amino acid sequence that has greater than about 90% amino acid sequence identity, for example, 91%, 92%, 93%, 94%, 95%, 96%, 97%, 98% or 99% or greater amino acid sequence identity, preferably over a region of at least about 25, 50, 100, 200, 400, or more amino acids, or over the full-length, to an amino acid sequence encoded by a CDK9 nucleic acid (see, e.g., GenBank Accession No. NM_001261.3); (2) bind to antibodies, e.g., polyclonal antibodies, raised against an immunogen comprising an amino acid sequence of a CDK9 polypeptide (e.g., GenBank Accession No. NP_001252.1); or an amino acid sequence encoded by a CDK9 nucleic acid (e.g., CDK9 polynucleotides described herein), and conservatively modified variants thereof; (3) specifically hybridize under stringent hybridization conditions to an anti-sense strand corresponding to a nucleic acid sequence encoding a CDK9 protein, and conservatively modified variants thereof; (4) have a nucleic acid sequence that has greater than about 90%, preferably greater than about 91%, 92%, 93%, 94%, 95%, 96%, 97%, 98%, 99%, or higher nucleotide sequence identity, preferably over a region of at least about 25, 50, 100, 200, 500, 1000, 2000 or more nucleotides, or over the full-length, to a CDK9 nucleic acid (e.g., CDK9 polynucleotides, as described herein, and CDK9 polynucleotides that encode CDK9 polypeptides, as described herein). Based on the knowledge of CDK9 homologs, those of skill can readily determine residue positions that are more tolerant to substitution. For example, amino acid residues conserved amongst species are less tolerant of substitution or deletion. Similarly, amino acid residues that are not conserved amongst species are more tolerant of substitution or deletion, while retaining the function of the CDK9 protein.

The term "bromodomain containing 4" or "BRD4" refers to a homologue of the murine protein MCAP, which associates with chromosomes during mitosis, and to the human RING3 protein, a serine/threonine kinase. BRD4 contains two bromodomains, a conserved sequence motif which may be involved in chromatin targeting. Structurally, "BRD4" refers to nucleic acids and polypeptide polymorphic variants, alleles, mutants, and interspecies homologs that: (1) have an amino acid sequence that has greater than about 90% amino acid sequence identity, for example, 91%, 92%, 93%, 94%, 95%, 96%, 97%, 98% or 99% or greater amino acid sequence identity, preferably over a region of at least about 25, 50, 100, 200, 400, or more amino acids, or over the full-length, to an amino acid sequence encoded by a BRD4 nucleic acid (see, e.g., GenBank Accession Nos. NM_014299.2 (short transcript variant) and NM_058243.2 (long transcript variant)); (2) bind to antibodies, e.g., polyclonal antibodies, raised against an immunogen comprising an amino acid sequence of a BRD4 polypeptide (e.g., GenBank Accession Nos. NP_055114.1 (short transcript variant) and NP_490597.1 (long transcript variant)); or an amino acid sequence encoded by a BRD4 nucleic acid (e.g., BRD4 polynucleotides described herein), and conservatively modified variants thereof; (3) specifically hybridize under stringent hybridization conditions to an anti-sense strand corresponding to a nucleic acid sequence encoding a BRD4 protein, and conservatively modified variants thereof; (4) have a nucleic acid sequence that has greater than about 90%, preferably greater than about 91%, 92%, 93%, 94%, 95%, 96%, 97%, 98%, 99%, or higher nucleotide sequence identity, preferably over a region of at least about 25, 50, 100, 200, 500, 1000, 2000 or more nucleotides, or over the full-length, to a BRD4 nucleic acid (e.g., BRD4 polynucleotides, as described herein, and BRD4 polynucleotides that encode BRD4 polypeptides, as described herein). Based on the knowledge of BRD4 homologs, those of skill can readily determine residue positions that are more tolerant to substitution. For example, amino acid residues conserved amongst species are less tolerant of substitution or deletion. Similarly, amino acid residues that are not conserved amongst species are more tolerant of substitution or deletion, while retaining the function of the BRD4 protein.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, α-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine I, Lysine (K);
5) Isoleucine (I), Leucine (L), Methionine (M), Valine (V);
6) Phenylalanine (F), Tyrosine (Y), Tryptophan (W); and
7) Serine (S), Threonine (T)
(see, e.g., Creighton, Proteins (1984)).

The terms "identical" or percent "identity," and variants thereof in the context of two or more polypeptide sequences, refer to two or more sequences or subsequences that are the same. Sequences are "substantially identical" if they have a specified percentage of amino acid residues or nucleotides that are the same (i.e., at least 60% identity, optionally at least 65%, 70%, 75%, 80%, 85%, 90%, 95%, 96%, 97%, 98%, or 99% identity over a specified region (or the whole reference sequence when not specified)), when compared and aligned for maximum correspondence over a comparison window, or designated region as measured using one of the following sequence comparison algorithms or by manual alignment and visual inspection. The present invention provides polypeptides substantially identical to CDK9, as described herein. Optionally, the identity exists over a region that is at least about 50 amino acids in length, or more preferably over a region that is 100 to 500 or 1000 or more amino acids in length, or over the full-length of the sequence.

The terms "similarity," or "percent similarity," and variants thereof in the context of two or more polypeptide sequences, refer to two or more sequences or subsequences that have a specified percentage of amino acid residues that are either the same or similar as defined in the 8 conservative amino acid substitutions defined above (i.e., 60%, optionally 65%, 70%, 75%, 80%, 85%, 90%, 95%, 96%, 97%, 98% or 99% similar over a specified region), when compared and aligned for maximum correspondence over a comparison window, or designated region as measured using one of the following sequence comparison algorithms or by manual alignment and visual inspection. Sequences having less than 100% similarity but that have at least one of the specified percentages are said to be "substantially similar." Optionally, this identity exists over a region that is at least about 50 amino acids in length, or more preferably over a region that is at least about 100 to 500 or 1000 or more amino acids in length, or over the full-length of the sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The term "comparison window", and variants thereof, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can also be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), Karlin and Altschul Proc. Natl. Acad. Sci. (U.S.A.) 87:2264-2268 (1990), or by manual alignment and visual inspection (see, e.g., Ausubel et al., Current Protocols in Molecular Biology (1995 supplement)).

Examples of an algorithm that is suitable for determining percent sequence identity and sequence similarity include the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information (on the internet at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-

5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. Standard BLAST algorithm parameters have an expected threshold of 10 (according to the stochastic model of Karlin and Altschul (PNAS, 87:2264-2268 (1990)); a word size of 28; reward and penalty of 1/−2 (a ratio of 0.5, or 1/−2, is used for sequences that are 95% conserved); and a linear GAP cost.

The term "effective amount" refers to an amount (here of an inhibitor of CDK9) which provides either subjective relief of a symptom(s) or an objectively identifiable improvement as noted by the clinician or other qualified observer. Determination of an effective amount is well within the capability of those skilled in the art, especially in light of the detailed disclosure provided herein. Generally, an efficacious or effective amount of a combination of one or more polypeptides of the present invention is determined by first administering a low dose or small amount of a polypeptide or composition and then incrementally increasing the administered dose or dosages, adding a second or third medication as needed, until a desired effect of is observed in the treated subject with minimal or no toxic side effects. Applicable methods for determining an appropriate dose and dosing schedule for administration of a combination of the present invention are described, for example, in *Goodman and Gilman's The Pharmacological Basis of Therapeutics,* 12th Edition, 2010, supra; in a Physicians' Desk Reference (PDR), 68$^{th}$ Edition, 2014, PDR Network; in *Remington: The Science and Practice of Pharmacy,* 21$^{st}$ Ed., 2006, supra; and in *Martindale: The Complete Drug Reference, Sweetman,* 2005, London: Pharmaceutical Press., and in Martindale, *Martindale: The Extra Pharmacopoeia,* 31st Edition., 1996, Amer Pharmaceutical Assn, each of which are hereby incorporated herein by reference.

"Subtherapeutic dose or amount" or "non-efficacious does or amount" interchangeably refer to a dose of a pharmacologically active agent(s), either as an administered dose of pharmacologically active agent, or actual level of pharmacologically active agent in a subject that functionally is insufficient to elicit the intended pharmacological effect in itself (e.g., to obtain anti-inflammatory effects), or that quantitatively is less than the established therapeutic dose for that particular pharmacological agent (e.g., as published in a reference consulted by a person of skill, for example, doses for a pharmacological agent published in the Physicians' Desk Reference, 68th Ed., 2014, PDR Network or Brunton, et al., Goodman & Gilman's The Pharmacological Basis of Therapeutics, 12th edition, 2010, McGraw-Hill Professional). A "subtherapeutic dose" can be defined in relative terms (i.e., as a percentage amount (less than 100%) of the amount of pharmacologically active agent conventionally administered). For example, a subtherapeutic dose amount can be about 1% to about 75% of the amount of pharmacologically active agent conventionally administered. In some embodiments, a subtherapeutic dose can be about 75%, 50%, 30%, 25%, 20%, 10% or less, than the amount of pharmacologically active agent conventionally administered.

The terms "treating" and "treatment" and variants thereof refer to promoting healing, delaying the onset of, retarding or reversing the progress of, alleviating or preventing either the disease or condition to which the term applies (e.g., cartilage degradation), or one or more symptoms of such disease or condition. Treating and treatment encompass both therapeutic and prophylactic treatment regimens.

The terms "subject," "patient," or "individual" interchangeably refer to any mammal, for example, humans and non-human primates, domestic mammals (e.g., canine, feline), agricultural mammals (e.g., bovine, equine, ovine, porcine) and laboratory mammals (e.g., mouse, rat, rabbit, hamster).

As used herein, "administering" refers to local and systemic administration, e.g., including enteral, parenteral, pulmonary, and topical/transdermal administration. Routes of administration for compounds (e.g., inhibitors of CDK9, e.g., flavopiridol, and analogs and salts thereof) that find use in the methods described herein include, e.g., oral (per os (P.O.)) administration, nasal or inhalation administration, administration as a suppository, topical contact, transdermal delivery (e.g., via a transdermal patch), intrathecal (IT) administration, intravenous ("iv") administration, intraperitoneal ("ip") administration, intramuscular ("im") administration, intralesional administration, or subcutaneous ("sc") administration, or the implantation of a slow-release device e.g., a mini-osmotic pump, a depot formulation, etc., to a subject. Administration can be by any route including parenteral and transmucosal (e.g., oral, nasal, vaginal, rectal, or transdermal). Parenteral administration includes, e.g., intravenous, intramuscular, intra-arterial, intradermal, subcutaneous, intraperitoneal, intraventricular, ionophoretic and intracranial. Other modes of delivery include, but are not limited to, the use of liposomal formulations, intravenous infusion, transdermal patches, etc.

The terms "systemic administration" and "systemically administered" refer to a method of administering a compound or composition to a mammal so that the compound or composition is delivered to sites in the body, including the targeted site of pharmaceutical action, via the circulatory system. Systemic administration includes, but is not limited to, oral, intranasal, rectal and parenteral (e.g., other than through the alimentary tract, such as intramuscular, intravenous, intra-arterial, transdermal and subcutaneous) administration.

The term "co-administering" or "concurrent administration", when used, for example with respect to the compounds (e.g., inhibitors of CDK9, e.g., flavopiridol, and analogs and salts thereof) and/or analogs thereof and another active agent, refers to administration of the compound and/or analogs and the active agent such that both can simultaneously achieve a physiological effect. The two agents, however, need not be administered together. In certain embodiments, administration of one agent can precede administration of the other. Simultaneous physiological effect need not necessarily require presence of both agents in the circulation at the same time. However, in certain embodiments, co-administering typically results in both agents being simultaneously present in the body (e.g., in the plasma) at a significant fraction (e.g., 20% or greater, preferably 30% or 40% or greater, more preferably 50% or 60% or greater, most preferably 70% or 80% or 90% or greater) of their maximum serum concentration for any given dose. For example, in various embodiments, an inhibitor of CDK9 is co-administered with protein complexes or protein scaffolds comprising one or more monomers of cartilage oligomeric matrix protein (COMP) bound to one or more growth factors, as described in co-owned and co-pending International Appl. No. PCT/US2011/051610.

The phrase "cause to be administered" refers to the actions taken by a medical professional (e.g., a physician), or a person controlling medical care of a subject, that control and/or permit the administration of the agent(s)/compound(s) at issue to the subject. Causing to be administered can involve diagnosis and/or determination of an appropriate therapeutic or prophylactic regimen, and/or prescribing particular agent(s)/compounds for a subject. Such prescribing can include, for example, drafting a prescription form, annotating a medical record, and the like.

BRIEF DESCRIPTION OF THE DRAWINGS

FIG. 2A illustrates the structure of Flavopiridol, a small molecule (MW=402) kinase inhibitor with a Kd of 3-6 nM for Cdk9. FIG. 2B illustrates the structure of JQ1, a small molecule Brd4 inhibitor (MW=456) that prevents Brd4 from binding acetylated histones and recruiting Cdk9 to promoters.

FIGS. 5A-C illustrate that Cdk9 inhibition, alone and with concurrent Brd4 inhibition blocks multiple upstream inflammatory signals. A) Cdk9 inhibition by Flavopiridol is effective against multiple inflammatory stimuli. Human primary chondrocytes (n=3 donors) were treated with 3 different inflammatory stimuli (10 ng/ml of either IL-1β, LPS, or TNF) with or without 300 nM Flavopiridol for 5 hours. The inducible nitric oxide synthase (iNOS) mRNA was quantified by real-time PCR as a representative of primary response genes. iNOS induction by each stimulus alone was arbitrarily set to 100% (first bar) and compared to the respective samples co-treated with Flavopiridol. Panel C) demonstrates that both Flavopiridol and JQ1 suppress the inflammatory response induced by IL-6. B) siRNA-mediated depletion of Cdk9 represses iNOS induction. Chondrocytes were transduced with lentiviral particles harboring siRNA against Cdk9 or GFP as control. After 5 days, cells were treated with IL-1β for 5 hours and harvested for Western (inset) and iNOS mRNA analysis. For all the above experiments, each data point was the mean+/−standard deviation from 3 different human donors. (*/**$p<0.05$).

FIGS. 6A-B illustrate that Cdk9 inhibition protects cartilage explants from mechanical injury-induced inflammation and apoptosis. Bovine cartilage explants (6 mm diameter×3 mm height, n=6) were subjected to a single load of compression of 30% strain/sec, then placed into media with or without 300 nM Flavopiridol. A) The expression of IL-6 mRNA over a period of 24 hours post-injury was determined by qPCR. (C=control, I=mechanically injured). Injury induced IL-6 mRNA but the induction was prevented by Cdk9 inhibitors. B) Cdk9 inhibition prevents injury induced apoptosis in cartilage explants. Mechanically injured cartilage explants (n=3 donors) were cultured with or with Flavopiridol and processed for histology. Apoptotic cells were detected with TUNEL staining (DeadEnd Fluorometric TUNEL system, Promega) and calculated as percentage of total cells (DAPI stain). Injury increased apoptotic cell population but the effect was reduced by Cdk9 inhibition in all time points tested (*$p<0.05$).

FIGS. 9A-H illustrate that CDK9 inhibition prevents injury-induced upregulation of pro-inflammatory cytokine and catabolic genes. A) Schematic representation of the cartilage explant injury and drug treatment, and the subsequent tests. B-F) Suppression of pro-inflammatory cytokine and catabolic enzyme genes by Flavopiridol in cartilage explants (C=control uninjured, I=injured) within 24 hours post-injury, G-H) Flavopiridol does not affect the expression of the anabolic genes aggrecan and collagen 2A. All values were the mean+/−standard deviation obtained from n=6 individual donors (*$p<0.05$).

FIGS. 10A-C illustrate that CDK9 inhibition reduces mRNA expression of apoptotic mediators. Flavopiridol suppresses mRNA expression of the pro-apoptotic genes p53, Bcl-2, and PTEN. All values were the mean+/−standard deviation obtained from n=6 individual donors (*$p<0.05$).

FIGS. 11A-B illustrate CDK9 inhibition rescues chondrocyte from injury-induced apoptosis. A) Flavopiridol treatment prevents chondrocyte apoptosis. At the indicated times, cartilage explants were processed for histological examination and TUNEL staining. Injury increased apoptosis in cartilage explants but Flavopiridol reduced the apoptotic cell population. Results were the mean+/−standard deviation obtained from n=3 individual donors (*p<0.05). B) Flavopiridol enhances chondrocyte survival. At 5-days post-injury, cartilage explants were stained with LIVE/DEAD viability stain. Injury decreased cell viability but the cells were rescued by Flavopiridol. Results were the mean+/− standard deviation obtained from n=6 individual donors (*p<0.05).

DETAILED DESCRIPTION

1. Introduction

Figure 1:
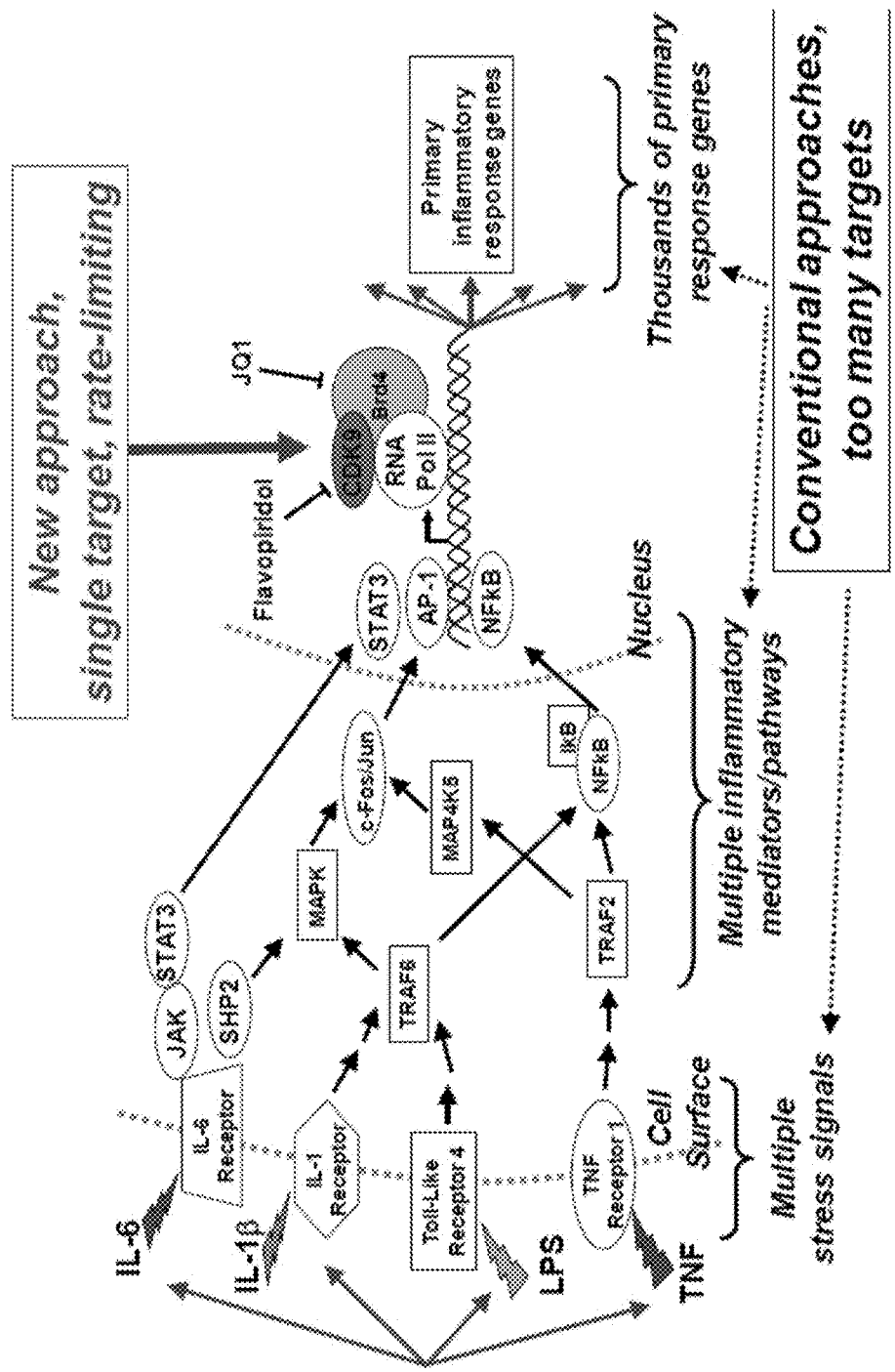
FIG. 1 illustrates an approach for anti-inflammatory therapy: Cdk9 controls the rate-limiting step for activation of primary inflammatory response genes. There are many different inflammatory stimuli, for example, IL-1β, LPS, and TNF activate their respective cell surface receptors and signal through different intracellular mediators/pathways, which ultimately converge on Cdk9-dependent activation of RNA pol II for transcription of most, if not all, primary inflammatory response genes. Therefore, targeting Cdk9's kinase activity, or its recruitment to promoter via Brd4, is ideal for effectively blocking all inflammatory genes activation regardless of the inflammatory source. Flavopiridol and JQ1 are small molecules Cdk9 and Brd4 inhibitors, respectively.

Provided are methods based, in part, on the discovery that combined inhibition of CDK9 and BRD4 activity finds use to prevent, reduce, and/or mitigate polytrauma or SIRS, preserve cartilage after injury (e.g., traumatic injury and/or surgical injury) and during storage (e.g., allograft storage). Any combination of CDK9 and BRD4 inhibitors known in the art can be used in the present methods, including inhibitory nucleic acids and inhibitory compounds (e.g., flavopiridol, JQ1, GSK525762A, and analogs and salts thereof).

Many different stimuli can induce inflammation, and several of these are being investigated individually as arthritis drugs (e.g., IL-1 antagonists, TNF antagonists, antioxidants). The focus has been on inhibition of the pathway so that transcription of response genes does not occur. None of these existing investigations have addressed the process of transcription. The present invention is based, in part, on the discovery that all of these pathways converge on the combined activation of CDK9 and BRD4 for the transcriptional elongation of the primary response genes. Inhibition of the transcriptional elongation by combined inhibition of CDK9 and BRD4 is limited to the primary response inflammatory genes, and combined CDK9 and BRD4 inhibition does not affect transcription of housekeeping genes, and therefore is not detrimental to cells or tissues in the short term. The combined advantage of CDK9 and BRD4 inhibition is that it reduces transcriptional elongation of inflammatory genes from all inflammatory stimuli. In various embodiments, CDK9 and BRD4 can be specifically and reversibly inhibited, e.g., with small-molecule drugs (e.g., flavopiridol and other known CDK9 inhibitors; JQ1, GSK525762A, and other known BRD4 inhibitors, and analogs and salts thereof) and/or inhibitory nucleic acids (e.g., siRNA, miRNA, antisense RNA).

Symptomatic osteoarthritis (OA) can be defined as the end-stage failure of load bearing joints at the organ level (1). While the etiology of OA remains incompletely understood, it is well established that joint injuries often progress to OA over time (2). High-energy joint traumas that cause intra-articular fractures often result in the rapid development of joint degradation and post-traumatic osteoarthritis (PTOA) (3). Even lower-energy traumas to the joint, which are much more common, will initiate slowly progressing cartilage and joint degradation that results in symptomatic PTOA many years later (2). As an example, from a total of 900,000 knee injuries annually in the United States (4), the American Academy of Orthopaedic Surgeons estimates 200,000 injuries of the anterior cruciate ligament (ACL) in the general population (5), including 2500 to 3000 ACL reconstructions in military patients (6). Strikingly, approximately 50% of these ACL injury patients will develop knee PTOA after a 10- to 20-year asymptomatic lag phase (7). NFL retirees under the age of 50 are five times more likely to have arthritis than comparable men in the general population, approximately 80% of retirees report having joint pain lasting most of the day, and over 23% of NFL retirees over 50 years of age have had a joint replacement.

Despite a lack of joint pain during the asymptomatic lag phase, progressive deterioration of bone and cartilage begins to develop soon after traumatic joint injury. In OA of the knee or hip joints, the asymptomatic cartilage degeneration phase can last many years or even decades (8). By the time arthritic joints become painful, there is often widespread cartilage damage with areas of complete cartilage loss. As a result of the extended painless "pre-OA" condition, the typical OA patient is seen in the clinic only after extensive joint damage has already occurred. At these late stages, treatment of the underlying causes of joint degeneration is no longer possible and the damage has become irreversible. Current OA treatments address the associated joint pain, but do not improve joint function or alter the underlying pathology. When these palliative treatments eventually fail, invasive surgical joint replacement is the only remaining treatment for pain-free ambulation. Although there is abundant evidence that joint traumas such as anterior cruciate ligament (ACL) tears will ultimately lead to OA (9-11), current clinical treatment does nothing at the time of these injuries to prevent the future onset of OA. Currently, clinical treatment is aimed at reducing the immediate pain and swelling in the joint and restoring normal joint movement. The most common recommendations are to apply ice, gently compress the joint with an elastic bandage, and take pain medications such as aspirin, acetaminophen, or ibuprofen. Importantly, these treatments do not address the initiation of OA. The incidence of OA is independent of whether patients undergo surgical reconstruction of the ACL (7,12), suggesting that the injury event, in addition to the chronic joint instability, has a causative role in OA pathogenesis.

The mechanical damage that a joint experiences during an impact has immediate effects on the tissues: cell death and physical damage to the joint tissues occur within milliseconds of impact. The immediate mechanical damage then triggers an acute cellular response, which occurs within a time-scale of minutes to hours (13). The acute response phase is characterized by the release of inflammatory mediators from the injured joint tissues, including IL-1, IL-6, iNOS, and TNF-α (13,14). This causes the transcriptional activation of primary response genes (or inflammatory genes), and leads to increased production of matrix degrading enzymes such as MMPs, collagenases, aggrecanases, and cathepsins. The enzymatic degradation of matrix contributes to OA via a cascade of destructive events, including:

(1) reducing the stiffness and elasticity of cartilage, thus increasing the mechanical stresses on chondrocytes,
(2) increasing the hydraulic permeability of cartilage, leading to loss of interstitial fluid and increased diffusion of solutes (i.e. degradative enzymes, proteoglycans),
(3) increasing the accessibility of remaining cartilage matrix structures to enzymatic digestion,
(4) thickening of the subchondral bone plate,
(5) structural changes to the trabecular bone, and
(6) formation of osteophytes and heterotopic bone (8).

We believe that a window for therapeutic intervention exists shortly after injury, during which attenuating the acute cellular response decreases production of matrix degrading enzymes and thus decreases the likelihood of developing post-traumatic osteoarthritis (PTOA).

One strategy to attenuate the systemic inflammatory response would be to target a common mechanism that controls these multiple inflammatory factors. Herein, we have identified a single conserved mechanism, in the cell nucleus, that controls the transcriptional elongation of all primary response genes. Inhibition of this common mechanism is possible with small molecule drugs already in clinical trials. Applying this completely new therapeutic strategy to severe trauma patients has great potential to save lives and decrease the medical costs by reducing the effects of SIRS, allowing the trauma team to more quickly stabilize the patient and treat injuries.

The transcriptional activation of primary response genes is an important step of the acute cellular response to injury. Transcriptional activation of primary response genes occurs in a timeframe of minutes to hours after the injury event. The majority of the primary response genes are 'primed' for transcription at a moment's notice, with the transcription complex already assembled on the promoters and the RNA polymerase complex stalled just before entering the transcription elongation stage. In a recent Cell paper, Hargreaves et al elegantly demonstrated that the rate-limiting step in transcriptional elongation of primary response genes is the recruitment of cyclin-dependent kinase-9 (CDK9) (15). In the case of inflammatory gene transcription, CDK9 is recruited to the transcription complex by NFκB (16,17). Importantly, CDK9 kinase activity is required for transcription of the primary response inflammatory genes to proceed, and this mechanism of regulation is conserved amongst primary response genes (18). Thus, combined inhibition of CDK9 kinase activity and BRD4 activity represents a new molecular target to inhibit the acute inflammatory response after joint injury.

After severe trauma, a plethora of conditions and sources can cause systemic inflammatory response syndrome (SIRS). Conventional anti-inflammatory drugs are ineffective against SIRS, because they only target a specific branch of the upstream inflammatory signaling networks, or one of the hundreds of inflammatory mediator genes (see FIG. 1). For example, corticosteroids, TLR4 antagonist, TNF and IL-1 receptor antagonists, antibradykinin, platelet activating factor receptor antagonists, and anticoagulants (antithrombin III) have all been studied without showing significant benefits in clinical trials. The present methods concurrently inhibit Cdk9 and Brd4 for suppressing systemic inflammation. By simultaneously inhibiting Cdk9 and Brd4, we block the rate-limiting step and bottle-neck for activation of all primary inflammatory response genes. The advantages of our approach are two-fold. First, it is effective against all upstream inflammatory stimuli regardless of their initiating signaling pathways. Second, it is efficient in suppressing the expression of most downstream inflammatory response genes. Therefore, blocking Cdk9 will block the full spectrum of inflammatory responses and represent a far more superior approach for modulating systemic inflammation after severe trauma.

2. Subjects Who May Benefit

Subjects who can benefit from a regime of combined one or more CDK9 inhibitors and one or more BRD4 inhibitors generally have experienced or imminently will experience a traumatic injury resulting in acute systemic inflammation, and/or an injury to cartilage tissue. In some embodiments, the subject may have experienced an injury (e.g., a traumatic injury), e.g., that damages cartilage tissue. In some embodiments, the subject may have experienced a traumatic injury, e.g., leading to acute systemic inflammation and possibly to multiple organ system failure. The subject may also undergo or have undergone surgery, e.g., to repair damaged cartilage tissue and/or to receive an osteochondral explant.

In various embodiments, a regime of combined one or more CDK9 inhibitors and one or more BRD4 inhibitors is administered to the subject within about 10 days after damage or injury to cartilage tissue, for example, within about 9, 8, 7, 6, 5, 4, 3, 2 or 1 days after damage or injury to cartilage tissue. In various embodiments, a regime of combined one or more CDK9 inhibitors and one or more BRD4 inhibitors are initially administered to the subject within about 72 hours, about 48 hours or about 24 hours after damage or injury to cartilage tissue or experiencing trauma, for example, within about 22, 20, 18, 16, 14, 12, 10, 9, 8, 7, 6, 5, 4, 3, 2, 1, or fewer, hours after damage or injury to cartilage tissue or experiencing trauma.

3. Inhibitors of CDK9 and BRD4

Generally, the activity of a CDK9, e.g., a polypeptide having at least 80% sequence identity, e.g., at least about 85%, 90%, 91%, 92%, 93%, 94%, 95%, 96%, 97%, 98% or 99% sequence identity, to an amino acid sequence of NP_001252.1, is inhibited or reduced, thereby preventing, reducing, delaying or inhibiting degradation of cartilage and/or onset or progression of post-traumatic osteoarthritis.

a. Small Organic Compounds i. CDK9 Inhibitors

CDK9 is a member of the cyclin-dependent kinase family, and most proteins in this family regulate cell-cycle progression. Over the last 2 decades there has been intense research into CDK inhibitors as anti-proliferative agents that arrest cell cycle progression in cancers, and numerous CDK inhibitors are in phase II and III clinical trials (19,20). CDK9, unlike most CDK proteins that regulate cell cycle progression, is mainly thought to regulate RNA synthesis and transcriptional elongation (21). There are small-molecule inhibitors with relatively good specificity for CDK9, including flavopiridol, and analogs and salts thereof. Commercial preparations of flavopiridol are called Alvocidib The IUPAC name for flavopiridol is 2-(2-chlorophenyl)-5,7-dihydroxy-8-[(3 S,4R)-3-hydroxy-1-methyl-4-piperidinyl]-4-chromenone). The structure of flavopiridol is shown below.

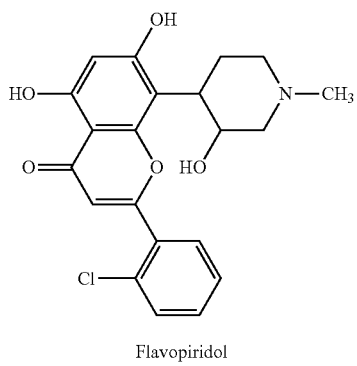 [SMILES: CN1CCC(c2c(O)cc(O)c3c(=O)cc(-c4ccccc4Cl)oc23)C(O)C1]

Flavopiridol

Flavopiridol inhibits CDK9 kinase activity by a high affinity (Kd=3 nM to 6 nM) interaction with the ATP-binding pocket of CDK9 (22,23). Inhibition of CDK9 kinase activity prevents transcriptional activation of primary response genes by preventing transcriptional elongation (15). Systemic administration of flavopiridol is well tolerated, and clinical trials with flavopiridol are successful in treating refractory chronic lymphocytic leukemia (24-26). Recently, Sekine et al have taken advantage of the anti-proliferative effects of flavopiridol in mouse models of rheumatoid arthritis (RA). They demonstrated that flavopiridol reduced synovial hyperplasia and effectively prevented rheumatoid arthritis (27). The anti-arthritic effect was reversible; when flavopiridol treatment was stopped, synovial hyperplasia resumed and RA progressed rapidly.

Other CDK inhibitors that can find use include without limitation, e.g., 4-(3,5-Diamino-1H-pyrazol-4-ylazo)-phenol (Calbiochem Catalog No. 238811), 2-(Pyridin-4-yl)-1,5,6,7-tetrahydro-4H-pyrrolo[3,2-c]pyridinone, PHA-767491 (Calbiochem Catalog No. 217707), and those described, e.g., in International Publication Nos. WO 2012/101066 (pyridine biaryl amine compounds); WO 2012/101065 (pyrimidine biaryl amine compounds); WO 2012/101064 (N-acyl pyrimidine biaryl compounds); WO 2012/101063 (N-acyl pyridine biaryl compounds); WO 2012/066070 (3-(aminoaryl)-pyridine compounds); WO 2012/066065 (phenyl-heteroaryl amine compounds); WO 2011/012661 (pyridine and pyrazine derivatives); WO 2011/077171 (4-phenylamino-pyrimidine derivatives); WO 2010/020675 (pyrrolopyrimidine compounds); WO 2008/079933 (heteroaryl-heteroaryl compounds); WO 2007/117653 (CDK9-PI3K-AKT inhibitors); WO 2006/024858 (4-arylazo-3,5-diamino-pyrazole compounds); WO 2006/021803 (purine and pyrimidine CDK inhibitors) and in U.S. Patent Publication Nos. 2012/0225899; 2012/0196855; 2012/0142680; 2010/0160350; 2010/0249149; 2010/0076000; 2010/0035870; 2010/0003246; 2009/0325983; 2009/0318446; 2009/0318441; 2009/0270427; 2009/0258886; 2009/0215805; 2009/0215805; 2009/0137572; 2008/0125404; 2007/0275963; 2007/0225270; 2007/0072882; 2007/0021452; 2007/0021419; and 2006/0264628, all of which are hereby incorporated herein by reference in their entirety for all purposes.

ii. BRD4 Inhibitors

Figure 2:
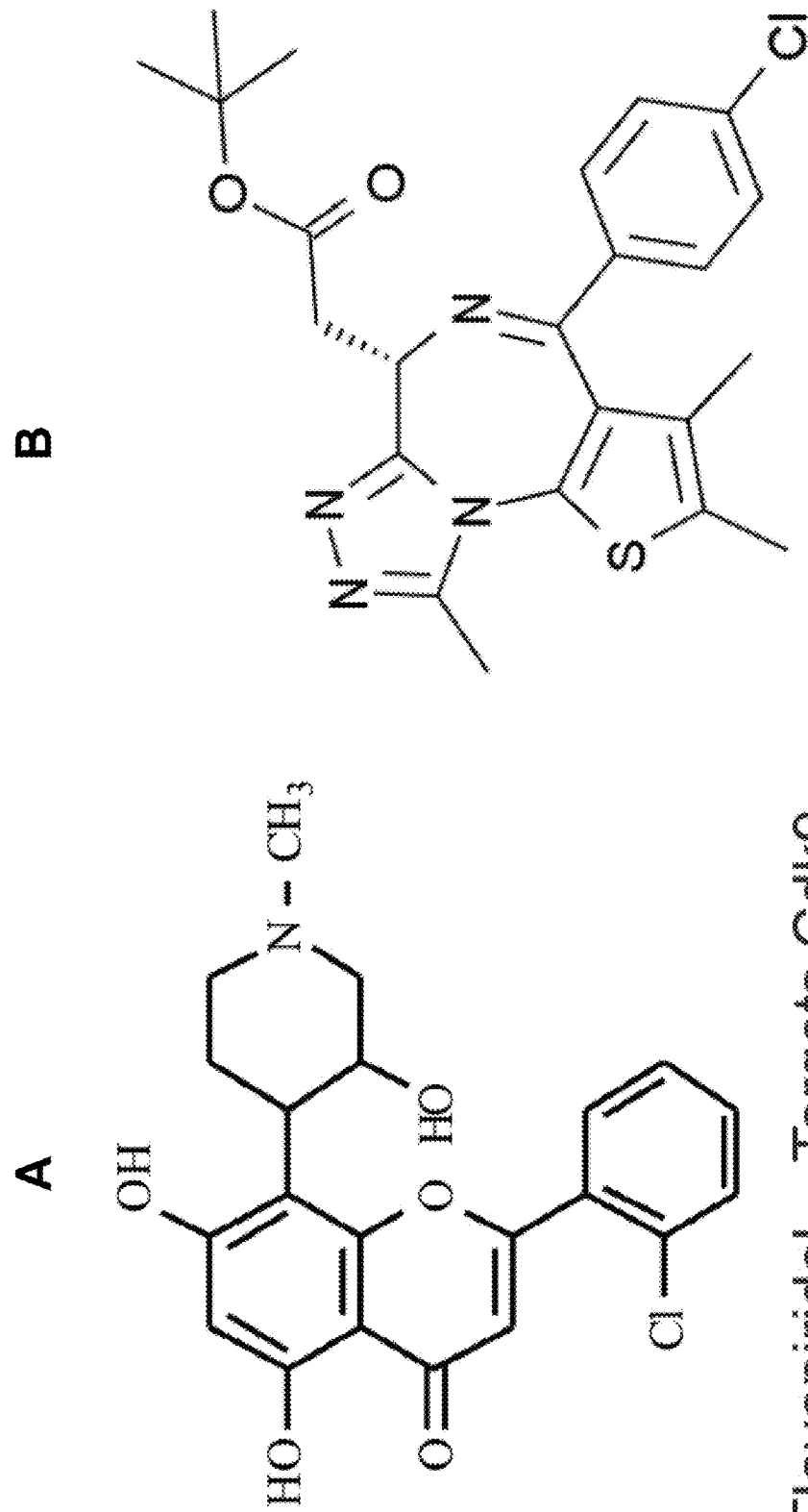
FIGS. 2A-B.

In addition to directly targeting the kinase activity of Cdk9 to suppress inflammation, a new class of small molecule inhibitors that blocks its recruitment to activated gene promoters by the bromodomain protein Brd4 was recently discovered as an effective Cdk9 inhibitors (Filippakopoulos, et al., (2010) Nature 468, 1067-1073). The compound JQ1 (FIG. 2 and below) is a bromodomain inhibitor that prevents Brd4 from binding acetylated histones at the chromosome near the promoters of activated primary response genes. Thus, JQ1 indirectly interferes with Cdk9 recruitment by Brd4 and has shown promising potential as a broad-spectrum anti-inflammatory agent in animal models (Belkina, et al., (2013) J. Immunol 190, 3670-3678). In our data herein, we demonstrate strong synergy between Cdk9 and Brd4 inhibitors in reducing and preventing inflammatory mediators.

Other BRD4 and bromodomain inhibitors that can find use include without limitation, e.g., those described in U.S. Patent Publication Nos. 2014/0296246, 2014/0296243, 2014/0243322, 2014/0243321, 2014/0243286, 2014/0044770, 2012/0208800 and 2012/0157428; and in Intl. Publication Nos. WO 2014/143768, WO 2014/160873, WO 2014/128067, WO 2014/026997, WO 2014/095775, WO 2014/095774, WO 2014/048945, WO 2014/128070; and WO 2014/128111. Preferred bromodomain inhibitors preferentially or specifically inhibit BRD4 activity. Additional BRD4 inhibitors of use are described in, e.g., Schulze, et al., J Biomol Screen. 2014 Sep. 29. PMID: 2526656; Philpott, et al., Epigenetics Chromatin. 2014 Jul. 13; 7:14; Wang, et al., Zhonghua Xue Ye Xue Za Zhi. 2014 June; 35(6):528-32; and Muvva, et al, Mol Biosyst. 2014 Jul. 29; 10(9):2384-97.

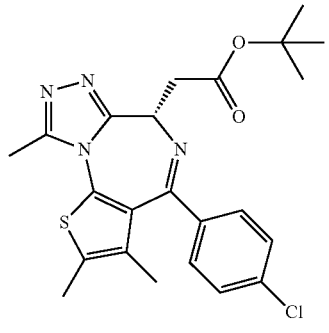

JQ1-Targets Brd4 b. Inhibitory Nucleic Acids

Concurrently or simultaneously decreasing or inhibiting CDK9 gene expression and BRD4 gene expression can be achieved using any method in the art, including through the use of inhibitory nucleic acids (e.g., small interfering RNA (siRNA), micro RNA (miRNA), antisense RNA, ribozymes, etc.). Inhibitory nucleic acids can be single-stranded nucleic acids that can specifically bind to a complementary nucleic acid sequence. By binding to the appropriate target sequence, an RNA-RNA, a DNA-DNA, or an RNA-DNA duplex or triplex is formed. Such inhibitory nucleic acids can be in either the "sense" or "antisense" orientation. See, for example, Tafech, et al., Curr Med Chem (2006) 13:863-81; Mahato, et al., Expert Opin Drug Deliv (2005) 2:3-28; Scanlon, Curr Pharm Biotechnol (2004) 5:415-20; and Scherer and Rossi, Nat Biotechnol (2003) 21:1457-65.

In one embodiment, the inhibitory nucleic acid can specifically bind to a target nucleic acid sequence or subsequence that encodes CDK9, BRD4 or both CDK9 and BRD4. Administration of such inhibitory nucleic acids can decrease or inhibit the activity of CDK9 and BRD4, and consequently, cartilage degradation. Nucleotide sequences encoding CDK9 are known for several mammalian species, including human, e.g., NM_001261.3. Nucleotide sequences encoding BRD4 are known for several mammalian species, including human, e.g., NM_014299.2→NP_055114.1 short isoform; and NM_058243.2→NP_490597.1 long isoform. From known CDK9 and BRD4 nucleotide sequences, one can derive a suitable inhibitory nucleic acid.

1. Antisense Oligonucleotides

In some embodiments, the inhibitory nucleic acid is an antisense molecule. Antisense oligonucleotides are relatively short nucleic acids that are complementary (or antisense) to the coding strand (sense strand) of the mRNA encoding CDK9 and/or BRD4. Although antisense oligonucleotides are typically RNA based, they can also be DNA based. Additionally, antisense oligonucleotides are often modified to increase their stability.

Without being bound by theory, the binding of these relatively short oligonucleotides to the mRNA is believed to induce stretches of double stranded RNA that trigger degradation of the messages by endogenous RNAses. Additionally, sometimes the oligonucleotides are specifically designed to bind near the promoter of the message, and under these circumstances, the antisense oligonucleotides may additionally interfere with translation of the message. Regardless of the specific mechanism by which antisense oligonucleotides function, their administration to a cell or tissue allows the degradation of the mRNA encoding CDK9 and/or BRD4. Accordingly, antisense oligonucleotides decrease the expression and/or activity of CDK9 and/or BRD4.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or agents facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. WO 88/09810) or the blood-brain barrier (see, e.g., PCT Publication No. WO 89/10134), hybridization-triggered cleavage agents (See, e.g., Krol et al., 1988, BioTechniques 6:958-976) or intercalating agents. (See, e.g., Zon, 1988, Pharm. Res. 5:539-549). To this end, the oligonucleotide can be conjugated to another molecule.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetyl cytosine, 5-(carboxyhydroxytriethyl) uracil, 5-carboxymethylaminomethyl-2-thiouridine, 5-carboxymethylaminomet-hyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methyl cytosine, 5-methyl cytosine, N6-adenine, 7-methylguanine, 5-methyl aminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

The antisense oligonucleotide can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an -anomeric oligonucleotide. An anomeric oligonucleotide forms specific double-stranded hybrids with complementary RNA in which, contrary to the usual-units, the strands run parallel to each other (Gautier et al., 1987, Nucl. Acids Res. 15:6625-6641). The oligonucleotide is a 2'-O-methylribonucleotide (Inoue et al., 1987, Nucl. Acids Res. 15:6131-6148), or a chimeric RNA-DNA analogue (Inoue et al., 1987, FEBS Lett. 215:327-330).

Oligonucleotides may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448-7451), etc.

The selection of an appropriate oligonucleotide can be readily performed by one of skill in the art. Given the nucleic acid sequence encoding CDK9 and/or BRD4, one of skill in the art can design antisense oligonucleotides that bind to a target nucleic acid sequence and test these oligonucleotides in an in vitro or in vivo system to confirm that they bind to and mediate the degradation of the mRNA encoding the CDK9. To design an antisense oligonucleotide that specifically binds to and mediates the degradation of a CDK9 and/or BRD4 encoding nucleic acid, it is preferred that the sequence recognized by the oligonucleotide is unique or substantially unique to the CDK9 and/or BRD4 to be inhibited. For example, sequences that are frequently repeated across an encoding sequence may not be an ideal choice for the design of an oligonucleotide that specifically recognizes and degrades a particular message. One of skill in the art can design an oligonucleotide, and compare the sequence of that oligonucleotide to nucleic acid sequences that are deposited in publicly available databases to confirm that the sequence is specific or substantially specific for CDK9 and/or BRD4.

A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it may be difficult to achieve intracellular concentrations of the antisense sufficient to suppress translation on endogenous mRNAs in certain instances. Therefore another approach utilizes a recombinant DNA construct in which the antisense oligonucleotide is placed under the control of a strong pol III or pol II promoter. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al, 1982, Nature 296:39-42), etc. Any type of plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route (e.g., systematically).

2. Small Interfering RNA (siRNA or RNAi)

In some embodiments, the inhibitory nucleic acid is a small interfering RNA (siRNA or RNAi) molecule. RNAi constructs comprise double stranded RNA that can specifically block expression of a target gene. "RNA interference" or "RNAi" is a term initially applied to a phenomenon where double-stranded RNA (dsRNA) blocks gene expression in a specific and post-transcriptional manner. RNAi provides a useful method of inhibiting gene expression in vitro or in vivo. RNAi constructs can include small interfering RNAs (siRNAs), hairpin RNAs, and other RNA species which can be cleaved in vivo to form siRNAs. RNAi constructs herein also include expression vectors ("RNAi expression vectors") capable of giving rise to transcripts which form dsRNAs or hairpin RNAs in cells, and/or transcripts which can produce siRNAs in vivo.

RNAi expression vectors express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences. The choice of promoter and other regulatory elements generally varies according to the intended host cell.

The RNAi constructs contain a nucleotide sequence that hybridizes under physiologic conditions of the cell to the nucleotide sequence of at least a portion of the mRNA transcript for the gene to be inhibited (i.e., a nucleic acid sequence encoding CDK9 and/or BRD4). The double-stranded RNA need only be sufficiently similar to natural RNA that it has the ability to mediate RNAi. Thus, the invention has the advantage of being able to tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity can be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, for example, 95%, 96%, 97%, 98%, 99%, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of an nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, any modified ribonucleotide can be introduced by in vitro enzymatic or organic synthesis.

Methods of chemically modifying RNA molecules can be adapted for modifying RNAi constructs (see, for example, Heidenreich et al. (1997) Nucleic Acids Res, 25:776-780; Wilson et al. (1994) J Mol Recog 7:89-98; Chen et al. (1995) Nucleic Acids Res 23:2661-2668; Hirschbein et al. (1997) Antisense Nucleic Acid Drug Dev 7:55-61). Merely to illustrate, the backbone of an RNAi construct can be modified with phosphorothioates, phosphoramidate, phosphodithioates, chimeric methylphosphonate-phosphodie-sters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules of the present invention can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Caplen, et al. (2001) Proc Natl Acad Sci USA, 98:9742-9747; Elbashir, et al. (2001) EMBO J, 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the Drosophila in vitro system is used. In this embodiment, dsRNA is combined with a soluble extract derived from Drosophila embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In certain preferred embodiments, at least one strand of the siRNA molecules has a 3' overhang from about 1 to about 6 nucleotides in length, though may be from 2 to 4 nucleotides in length. More preferably, the 3' overhangs are 1-3 nucleotides in length. In certain embodiments, one strand having a 3' overhang and the other strand being blunt-ended or also having an overhang. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

In other embodiments, the RNAi construct is in the form of a long double-stranded RNA. In certain embodiments, the RNAi construct is at least 25, 50, 100, 200, 300 or 400 bases. In certain embodiments, the RNAi construct is 400-800 bases in length. The double-stranded RNAs are digested intracellularly, e.g., to produce siRNA sequences in the cell. However, use of long double-stranded RNAs in vivo is not always practical, presumably because of deleterious effects which may be caused by the sequence-independent dsRNA response. In such embodiments, the use of local delivery systems and/or agents which reduce the effects of interferon are preferred.

In certain embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., Genes Dev, 2002, 16:948-58; McCaffrey et al., Nature, 2002, 418:38-9; McManus et al., RNA, 2002, 8:842-50; Yu et al., Proc Natl Acad Sci USA, 2002, 99:6047-52). Preferably, such hairpin RNAs are engineered in cells or in an animal to ensure continuous and stable suppression of a desired gene. It is known in the art that siRNAs can be produced by processing a hairpin RNA in the cell.

In yet other embodiments, a plasmid is used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO 01/77350 describes an exemplary vector for bi-directional transcription of a transgene to yield both sense and antisense RNA transcripts of the same transgene in a eukaryotic cell. Accordingly, in certain embodiments, the present invention provides a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

RNAi constructs can comprise either long stretches of double stranded RNA identical or substantially identical to the target nucleic acid sequence or short stretches of double stranded RNA identical to substantially identical to only a region of the target nucleic acid sequence. Exemplary methods of making and delivering either long or short RNAi constructs can be found, for example, in WO 01/68836 and WO 01/75164.

Exemplary RNAi constructs that specifically recognize a particular gene, or a particular family of genes can be selected using methodology outlined in detail above with respect to the selection of antisense oligonucleotide. Similarly, methods of delivery RNAi constructs include the methods for delivery antisense oligonucleotides outlined in detail above.

3. Ribozymes

In some embodiments, the inhibitory nucleic acid is a ribozyme. Ribozymes molecules designed to catalytically cleave an mRNA transcripts can also be used to prevent translation of mRNA (See, e.g., PCT International Publication WO 90/11364; Sarver et al., 1990, Science 247:1222-1225 and U.S. Pat. No. 5,093,246). While ribozymes that cleave mRNA at site-specific recognition sequences can be used to destroy particular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585-591.

The ribozymes of the present invention also include RNA endoribonucleases (hereinafter "Cech-type ribozymes") such as the one which occurs naturally in Tetrahymena thermophila (known as the IVS, or L-19 IVS RNA) and which has been extensively described by Thomas Cech and collaborators (Zaug, et al., 1984, Science, 224:574-578; Zaug and Cech, 1986, Science, 231:470-475; Zaug, et al., 1986, Nature, 324:429-433; WO 88/04300; Been and Cech, 1986, Cell, 47:207-216). The Cech-type ribozymes have an eight base pair active site that hybridizes to a target RNA sequence whereafter cleavage of the target RNA takes place. The invention encompasses those Cech-type ribozymes that target eight base-pair active site sequences.

As in the antisense approach, the ribozymes can be composed of modified oligonucleotides (e.g., for improved stability, targeting, etc.) and can be delivered to cells in vitro or in vivo. A preferred method of delivery involves using a DNA construct "encoding" the ribozyme under the control of a strong constitutive pol III or pol II promoter, so that transfected cells will produce sufficient quantities of the ribozyme to destroy targeted messages and inhibit translation. Because ribozymes unlike antisense molecules, are catalytic, a lower intracellular concentration is required for efficiency.

DNA enzymes incorporate some of the mechanistic features of both antisense and ribozyme technologies. DNA enzymes are designed so that they recognize a particular target nucleic acid sequence, much like an antisense oligonucleotide, however much like a ribozyme they are catalytic and specifically cleave the target nucleic acid.

There are currently two basic types of DNA enzymes, and both of these were identified by Santoro and Joyce (see, for example, U.S. Pat. No. 6,110,462). The 10-23 DNA enzyme comprises a loop structure which connect two arms. The two arms provide specificity by recognizing the particular target nucleic acid sequence while the loop structure provides catalytic function under physiological conditions.

Briefly, to design an ideal DNA enzyme that specifically recognizes and cleaves a target nucleic acid, one of skill in the art must first identify the unique target sequence. This can be done using the same approach as outlined for antisense oligonucleotides. Preferably, the unique or substantially sequence is a G/C rich of approximately 18 to 22 nucleotides. High G/C content helps insure a stronger interaction between the DNA enzyme and the target sequence.

When synthesizing the DNA enzyme, the specific antisense recognition sequence that will target the enzyme to the message is divided so that it comprises the two arms of the DNA enzyme, and the DNA enzyme loop is placed between the two specific arms.

Methods of making and administering DNA enzymes can be found, for example, in U.S. Pat. No. 6,110,462. Similarly, methods of delivery DNA ribozymes in vitro or in vivo include methods of delivery RNA ribozyme, as outlined in detail above. Additionally, one of skill in the art will recognize that, like antisense oligonucleotide, DNA enzymes can be optionally modified to improve stability and improve resistance to degradation.

4. Formulation and Administration

In therapeutic applications, a combination of the one or more CDK9 inhibitors and the one or more BRD4 inhibitors can be administered to an individual who has suffered a traumatic injury to cartilage tissue, who has undergone surgery to repair cartilage tissue and/or who has received a cartilage allograft. Compositions that contain a combination of one or more CDK9 inhibitors and one or more BRD4 inhibitors are administered to a patient in an amount sufficient to suppress the undesirable inflammation and to eliminate or at least partially arrest symptoms and/or complications. An amount adequate to accomplish this is defined as a "therapeutically effective dose." Amounts effective for this use will depend on, e.g., the inhibitor composition, the manner of administration, the stage and severity of the disease being treated, the weight and general state of health of the patient, and the judgment of the prescribing physician. A combination of inhibitors of CDK9 and BRD4 activity can be administered chronically or acutely to reduce, inhibit or prevent cartilage degradation and post traumatic osteoarthritis. In certain instances, it will be appropriate to administer one or more inhibitors of CDK9 activity and one or more inhibitors of BRD4 activity prophylactically, for instance in subjects at risk of or suspected of developing cartilage degradation and/or post traumatic osteoarthritis.

Alternatively, DNA or RNA that inhibits expression of one or more sequences encoding a CDK9 protein, such as an antisense nucleic acid, a small-interfering nucleic acid (i.e., siRNA), a micro RNA (miRNA), or a nucleic acid that encodes a peptide that blocks expression or activity of a CDK9 can be introduced into patients to achieve inhibition. U.S. Pat. No. 5,580,859 describes the use of injection of naked nucleic acids into cells to obtain expression of the genes which the nucleic acids encode.

Therapeutically effective amounts of CDK9 inhibitor or enhancer compositions of the present invention generally range for the initial administration (that is for therapeutic or prophylactic administration) from about 0.1 µg to about 10 mg, or less, of CDK9 inhibitor and/or BRD4 inhibitor for a 70 kg patient, usually from about 1.0 µg to about 1 mg, or less, for example, between about 10 µg to about 0.1 mg (100 µg), or less, particularly when the CDK9 inhibitor and BRD4 inhibitor are co-administered. Whereas the combination of the CDK9 inhibitor and BRD4 inhibitor are together efficacious, the amounts of the individual CDK9 inhibitor and/or BRD4 inhibitor can be non-efficacious. Typically, lower doses are initially administered and incrementally increased until a desired efficacious dose is reached. These doses can be followed by repeated administrations over weeks to months depending upon the patient's response and condition by evaluating symptoms associated with cartilage degradation and/or post-traumatic osteoarthritis.

For prophylactic use, administration should be given to subjects at risk for or suspected of developing cartilage degradation and/or post-traumatic osteoarthritis. Therapeutic administration may begin concurrently with surgical and/or allograft procedures, and/or as soon as possible after traumatic injury or surgery. This is often followed by repeated administration until at least symptoms are substantially abated and for a period thereafter. In some embodiments, the inhibitor of CDK9 and the inhibitor of BRD4 are co-administered within 10 days, e.g., within 9, 8, 7, 6, 5, 4, 3, 2, 1 days, e.g., within 24, 20, 18, 16, 14, 12, 10, 9, 8, 7, 6, 5, 4, 3, 2, 1 hours after experiencing traumatic injury. In some embodiments, the subject has undergone surgery to repair damaged cartilage tissue. In some embodiments, the subject has received an osteochondral explant, e.g., a cartilage allograft. In some embodiments, the inhibitor of CDK9 and the inhibitor of BRD4 are co-administered concurrently with or prior to surgery. In some embodiments, the inhibitor of CDK9 and the inhibitor of BRD4 are co-administered within 10 days, e.g., within 9, 8, 7, 6, 5, 4, 3, 2, 1 days, e.g., within 24, 20, 18, 16, 14, 12, 10, 9, 8, 7, 6, 5, 4, 3, 2, 1 hours after surgery. In some embodiments, the inhibitor of CDK9 and the inhibitor of BRD4 are co-administered over a course of 10 days, e.g., over 9, 8, 7, 6, 5, 4, 3, 2, 1 days. In various embodiments, the inhibitor of CDK9 and the inhibitor of BRD4 are co-administered every 2 days, every day, or twice daily, as appropriate.

The combination of one or more CDK9 inhibitors and one or more BRD4 inhibitors for therapeutic or prophylactic treatment are intended for systemic (e.g., parenteral, topical, oral, transdermal) or local (e.g., intralesional) administration. Preferably, the compositions are formulated for oral administration. In certain embodiments, the pharmaceutical compositions are administered parenterally, e.g., intravenously, intranasally, inhalationally, subcutaneously, intradermally, or intramuscularly. Compositions are also suitable for oral administration. Thus, the invention provides compositions for parenteral administration which comprise a solution of the CDK9 inhibiting agent and the BRD4 inhibiting agent dissolved or suspended in an acceptable carrier, preferably an aqueous carrier. A variety of aqueous carriers may be used, e.g., water, buffered water, 0.9% saline, 0.3% glycine or another suitable amino acid, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

In embodiments where one or both of the CDK9 inhibitor and the BRD4 inhibitor are small organic compounds, the compound (e.g., flavopiridol, JQ1, GSK525762A) and/or an analog thereof can be administered orally, parenterally, (intravenously (IV), intramuscularly (IM), depo-IM, subcutaneously (SQ), and depo-SQ), sublingually, intranasally (inhalation), intrathecally, transdermally (e.g., via transdermal patch), topically, ionophoretically or rectally. Typically the dosage form is selected to facilitate delivery to the brain (e.g., passage through the blood brain barrier). In this context it is noted that the compounds described herein are readily delivered to the brain. Dosage forms known to those of skill in the art are suitable for delivery of the compound.

In varying embodiments, the CDK9 inhibitor and the BRD4 inhibitor are co-administered intravenously. In embodiments where the CDK9 inhibitor is flavopiridol, dosing can be in accordance with concentrations and scheduling reported in the art. For example, in various embodiments, flavopiridol is administered intravenously in a concentration range of about 10 to about 105 mg/m$^2$ in infusions delivered over 1 to 4 hours, as appropriate. See, e.g., Ramaswamy, et al., *Invest New Drugs*. (2012) 30(2):629-38; Phelps, et al., *Blood*. (2009) 113(12):2637-45; and Byrd, et al., *Blood*. (2007) 109(2):399-404. In varying embodiments, JQ1 can be administered at nanomolar concentrations, e.g., 10-5000 nM, e.g., 50-1000 nM, e.g., 50-500 nM. In varying embodiments, JQ1 is administered at a dose of about 50 mg/kg. See, e.g., Trabucco, et al., Clin Cancer Res. 2014 Jul. 9, PMID 25009295; and Spiltoir, et al., J Mol Cell Cardiol. 2013 October; 63:175-9.

Compositions are provided that contain therapeutically effective amounts of the compound. The compounds are preferably formulated into suitable pharmaceutical preparations such as tablets, capsules, or elixirs for oral administration or in sterile solutions or suspensions for parenteral administration. Typically the compounds described above are formulated into pharmaceutical compositions using techniques and procedures well known in the art.

These active agents (e.g., flavopiridol and/or analogs thereof) can be administered in the "native" form or, if desired, in the form of salts, esters, amides, prodrugs, derivatives, and the like, provided the salt, ester, amide, prodrug or derivative is suitable pharmacologically effective, e.g., effective in the present method(s). Salts, esters, amides, prodrugs and other derivatives of the active agents can be prepared using standard procedures known to those skilled in the art of synthetic organic chemistry and described, for example, by March (1992) *Advanced Organic Chemistry; Reactions, Mechanisms and Structure*, 4th Ed. N.Y. Wiley-Interscience.

Methods of formulating such derivatives are known to those of skill in the art. For example, the disulfide salts of a number of delivery agents are described in PCT Publication WO 2000/059863 which is incorporated herein by reference. Similarly, acid salts of therapeutic peptides, peptoids, or other mimetics, and can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, orotic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the active agents herein include halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. In certain embodiments basic salts include alkali metal salts, e.g., the sodium salt, and copper salts.

For the preparation of salt forms of basic drugs, the pKa of the counterion is preferably at least about 2 pH lower than the pKa of the drug. Similarly, for the preparation of salt forms of acidic drugs, the pKa of the counterion is preferably at least about 2 pH higher than the pKa of the drug. This permits the counterion to bring the solution's pH to a level lower than the pHmax to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (e.g., break down into the individual entities of drug and counterion) in an aqueous environment.

Preferably, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

In various embodiments preparation of esters typically involves functionalization of hydroxyl and/or carboxyl groups that are present within the molecular structure of the active agent. In certain embodiments, the esters are typically acyl-substituted derivatives of free alcohol groups, e.g., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

The concentration of CDK9 inhibiting agents and the BRD4 inhibiting agents in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The CDK9 inhibitors and/or the BRD4 inhibitors may also be administered via liposomes, which can be designed to target the conjugates to a particular tissue, for example, cartilage tissue. Liposomes include emulsions, foams, micelles, insoluble monolayers, liquid crystals, phospholipid dispersions, lamellar layers and the like. In these preparations, the peptide, nucleic acid or organic compound to be delivered is incorporated as part of a liposome, alone or in conjunction with a molecule which binds to, e.g., a receptor prevalent among the desired cells, or with other therapeutic compositions. Thus, liposomes filled with a desired peptide, nucleic acid, small molecule or conjugate can be directed to the damaged or injured lesion, for example, cartilage tissue, joints, injured lesions, where the liposomes then deliver the selected CDK9 inhibitor and/or BRD4 inhibitor compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid liability and stability of the liposomes in the blood stream. A variety of methods are available for preparing liposomes, as described in, e.g., Szoka et al., Ann. Rev. Biophys. Bioeng. 9:467 (1980), U.S. Pat. Nos. 4,235,871, 4,501,728 and 4,837,028.

The targeting of liposomes using a variety of targeting agents is well known in the art (see, e.g., U.S. Pat. Nos. 4,957,773 and 4,603,044). For targeting to desired cells, a ligand to be incorporated into the liposome can include, e.g., antibodies or fragments thereof specific for cell surface determinants of the target cells. A liposome suspension containing a CDK9 inhibitor and/or BRD4 inhibitor may be administered intravenously, locally (e.g., intralesionally), topically, etc., in a dose which varies according to, inter alia, the manner of administration, the conjugate being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more conjugates, and more preferably at a concentration of 25%-75%.

For aerosol administration, the inhibitors are preferably supplied in a suitable form along with a surfactant and propellant. Typical percentages of CDK9 inhibitors and BRD4 inhibitors are 0.01%-20% by weight, preferably 1%-10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A carrier can also be included, as desired, as with, e.g., lecithin for intranasal delivery.

An effective treatment is indicated by a decrease in observed symptoms (e.g., pain, swelling, joint mobility) as measured according to a clinician or reported by the patient. Alternatively, methods for detecting levels of specific CDK9 activities and/or BRD4 activities can be used. Standard assays for detecting CDK9 activity and/or BRD4 activity are described herein. Again, an effective treatment is indicated by a substantial reduction in activity of CDK9 and/or BRD4. As used herein, a "substantial reduction" in CDK9 activity and/or BRD4 activity refers to a reduction of at least about 30% in the test sample compared to an untreated control.

Preferably, the reduction is at least about 50%, more preferably at least about 75%, and most preferably CDK9 and/or BRD4 activity levels are reduced by at least about 90% in a sample from a treated mammal compared to an untreated control. In some embodiments, the CDK9 activity and/or BRD4 activity is completely inhibited.

5. Matrices Comprising an Inhibitor of CDK9 and an Inhibitor of BRD4

In various embodiments, a combination of one or more CDK9 inhibitors and one or more BRD4 inhibitors can be contained within a matrix or a depot. The matrix can serve, in one capacity, as a delivery vehicle for the composition to be delivered to the site of a cartilage lesion or a bone lesion. The matrix also provides a suitable scaffold upon which cartilage repair and regeneration can occur. In one embodiment, the matrix is bioresorbable or biodegradable.

In various embodiments, the matrix can be formed of any material that is suitable for in vivo use, and which provides the characteristics facilitating cartilage repair or bone repair in the presence of an inhibitor of CDK9 and an inhibitor of BRD4. The matrix can be formed of materials which include, but are not limited to, synthetic polymers and/or a ground substance. Preferred ground substances include natural polymers and proteoglycans. Natural polymers include, but are not limited to collagen, elastin, reticulin and analogs thereof Proteoglycans include, but are not limited to, any glycosaminoglycan-containing molecules. Particularly preferred glycosaminoglycans include chondroitin sulfate, dermatan sulphate, heparan sulphate, keratan sulphate and hyaluronan. Other preferred ground substances include, but are not limited to, type I collagen, type II collagen, type III collagen, type IV collagen and hyaluronic acid. Preferred synthetic polymers include poly(lactic acid) and poly(glycolic acid).

In one embodiment of the present invention, the matrix includes collagen. For example, the matrix can contain from about 20% to about 100% collagen by dry weight of the matrix, for example, from about 50% to about 100% collagen by dry weight of the matrix, for example, from about 75% to about 100% collagen by dry weight of the matrix.

A matrix suitable for use with one or more inhibitors of CDK9 and one or more inhibitors of BRD4 can include materials in any suitable form for use in repairing a cartilage lesion or a bone lesion, including a sponge, a membrane, a film or a gel. In one embodiment, a suitable repair matrix includes demineralized bone matrix, synthetic bone graft substitute, autograft tissue, allograft tissue and/or xenograft tissue. In some embodiments, the matrix is formulated for use as a bone graft, for example, as a spinal graft.

Suitable methods for associating an inhibitor of CDK9 and an inhibitor of BRD4 with a matrix include any method which allows the inhibitors to be delivered to a site of cartilage repair or bone repair together with the matrix such that the cartilage repair or bone repair product is effective to repair and/or regenerate cartilage or bone at the site. Such methods of association include, but are not limited to, suspension of the composition within the matrix, freeze-drying of the composition onto a surface of the matrix and suspension within the matrix of a carrier/delivery formulation containing the composition. Additionally, the one or more inhibitors of CDK9 and the one or more inhibitors of BRD4 can be associated with the matrix prior to placement of the product into a cartilage lesion (i.e., the association of the composition with matrix occurs ex vivo) or alternatively, the matrix can first be implanted into a lesion, followed by association of the one or more inhibitors of CDK9 and the one or more inhibitors of BRD4 with the matrix, such as by injection into or on top of the matrix (i.e., the association of the composition with matrix occurs in vivo).

The combination of one or more inhibitors of CDK9 and one of more inhibitors of BRD4 can contain additional delivery formulations or carriers which enhance the association of the composition with the matrix, which enhance the delivery of the composition to the appropriate cells and tissue at the site of the lesion, and which assist in controlling the release of the factors in the composition at the site of the lesion. Suitable delivery formulations include carriers, which, as used herein, include compounds that increase the half-life of a cartilage-inducing composition in the treated animal. Suitable carriers include, but are not limited to, polymeric controlled release vehicles, biodegradable implants, liposomes, bacteria, viruses, oils, cells, esters, and glycols. Preferably, the matrices are bioresorbable or biodegradable.

The combination of one or more inhibitors of CDK9 and one or more inhibitors of BRD4 are present in the matrix at a concentration that is effective to induce, at the site of a cartilage lesion or a bone lesion, one or more of: cellular infiltration, cellular proliferation, angiogenesis, and cellular differentiation to type II collagen-producing chondrocytes. Individually, one or more inhibitors of CDK9 and/or one or more inhibitors of BRD4 can be present at non-efficacious concentrations. In varying embodiments, the one or more inhibitors of CDK9 and one or more BRD4 inhibitors are present in the matrices at a concentration that the combination is effective to induce cartilage repair and/or regeneration at the site of a cartilage lesion or a bone lesion. One of skill in the art will be able to adjust the concentration of proteins and/or nucleic acid molecules in the composition depending on the types and number of proteins to be provided by the composition, and the delivery vehicle used.

The matrices can also contain one or more substances that non-covalently attach to the one or more inhibitors of CDK9 and the one or more inhibitors of BRD4 in the composition and thus, modify the release rate of the growth factor. Such substances include, but are not limited to, any ground substance or other polymeric substance. As used herein, a ground substance is defined as the non-living matrix of connective tissue, which includes natural polymers and proteoglycans. Natural polymers include, but are not limited to collagen, elastin, reticulin and analogs thereof. Proteoglycans include, but are not limited to any glycosaminoglycan-containing molecules, and include chondroitin sulfate, dermatan sulphate, heparan sulphate, keratan sulphate and hyaluronan. Preferred ground substances include, but are not limited to, type I collagen, type II collagen, type III collagen, type IV collagen and hyaluronic acid. Preferred other polymeric substances include, but are not limited to, poly(lactic acid) and poly(glycolic acid).

In a further embodiment, the matrices can include one or more types of cells which are provided to further enhance chondrogenesis at the site of the cartilage lesion. Such cells include, but are not limited to, fibrochondrocytes, chondrocytes, mesenchymal precursors, and any other cell that can serve as a chondrocyte precursor. Such cells can be associated with the composition and the matrix by any of the methods described above.

In some aspects of the present invention, matrices comprising the one or more inhibitors of CDK9 and one or more inhibitors of BRD4 further comprise at least one bone matrix protein. As used herein, "bone matrix proteins" are any of a group of proteins known in the art to be a component of or associated with the minute collagenous fibers and ground substances which form bone matrix. In various embodiments, the matrices comprise a bone matrix protein that is a member of the TGF-β superfamily, a growth factor protein and/or Cartilage Oligomeric Matrix Protein (COMP). Bone matrix proteins can also include, but are not limited to, osteocalcin, osteonectin, bone sialoprotein (BSP), lysyloxidase, cathepsin L pre, osteopontin, matrix GLA protein (MGP), biglycan, decorin, proteoglycan-chondroitin sulfate III (PG-CS III), bone acidic glycoprotein (BAG-75), thrombospondin (TSP) and/or fibronectin. Preferably, bone matrix proteins suitable for use with the product of the present invention include one or more of: osteocalcin, osteonectin, MGP, TSP, BSP, lysyloxidase and cathepsin L pre. In one embodiment, the at least one bone matrix protein includes at least osteocalcin, osteonectin, BSP, lysyloxidase and cathepsin L pre. A particularly preferred bone matrix protein is MGP, and more preferred is osteonectin, and most preferred is TSP.

The matrices comprising the one or more inhibitors of CDK9 and the one or more inhibitors of BRD4 are useful for repairing a variety of defects in cartilage, including both tears and segmental defects in both vascular and avascular cartilage tissue. The product is particularly useful for repairing defects in hyaline (e.g., articular) and/or fibrocartilage (e.g., meniscal). For example, matrices comprising one or more inhibitors of CDK9 and one or more inhibitors of find use promoting repair of a meniscal radial tear; a meniscal triple bucket handle tear; a longitudinal tear in the avascular area of a meniscus; or a meniscal segmental lesion.

Because cartilage defects and bone defects (i.e., lesions) can occur in a variety of shapes, sizes, and locations, a matrix comprising the one or more inhibitors of CDK9 and the one or more inhibitors of BRD4 is of a shape and size sufficient to conform to a specific defect in the cartilage or the bone of the patient to be treated. Preferably, the matrix, when used in the repair of a cartilage defect or bone defect, achieves a geometry at the defect site that is suitable to provide a therapeutic benefit to the patient. Such a therapeutic benefit can be any improvement in a patient's health and well-being that is related to a correction of the cartilage defect or the bone defect, and preferably, the therapeutic benefit includes the repair of the defect such that the natural configuration of the cartilage or the bone is at least partially restored. The matrix can be fixed or implanted directly into a cartilage lesion or a bone lesion.

6. Compositions and Kits

In a related aspect, the invention provides compositions comprising an osteochondral explant (e.g., ex vivo cartilage tissue) and/or chondrocytes in a solution comprising an inhibitor of cyclin-dependent kinase 9 (CDK9) and an inhibitor of bromodomain containing 4 (BRD4). In some embodiments, the osteochondral explant is allograft cartilage. In some embodiments, the inhibitor of CDK9 is a small organic compound, e.g., flavopiridol, or analogs and salts thereof. In some embodiments, the inhibitor of BRD4 is a small organic compound, e.g., JQ1, GSK525762A, or analogs and salts thereof. In some embodiments, the osteochondral explant is submerged in the solution comprising the inhibitor of CDK9 and the inhibitor of BRD4. In varying embodiments, the solution is an aqueous solution, e.g., a physiologically isotonic solution. In some embodiments, the solution comprises flavopiridol at a concentration in the range of about 100 nM to about 1000 nM, e.g., about 300 nM, or less. In some embodiments, the solution comprises JQ1 and/or GSK525762A at a concentration in the range of about 100 nM to about 1000 nM, e.g., about 300 nM, or less. When the solution contains a combination of a CDK9 inhibitor (e.g., flavopiridol) and a BRD4 inhibitor (e.g., JQ1 and/or GSK525762A), one or both compounds can be at a non-efficacious concentration, e.g., 75%, 50% or 25% of a concentration in the range of about 100 nM to about 1000 nM, e.g., about 300 nM. The solution may contain additional pharmaceutically acceptable excipients, described herein. In some embodiments, the composition is provided as a packaged kit.

EXAMPLES

The following examples are offered to illustrate, but not to limit the claimed invention.

Example 1

Inhibition of CDK9 and BRD4 in Chondrocytes Under Inflammatory Stimuli

Materials and Methods

Treatment of Chondrocytes.

Primary chondrocytes were isolated from cartilage of healthy human donors with IRB approval and cultured in DMEM with 10% FBS. Statistical design-of-experiment was performed using JMP 10.0 software to identify the minimum concentration of each drug alone, or in combination, required for complete inhibition of IL-1β-induced iNOS transcription. Chondrocytes were treated with either 10 ng/ml of IL-1β or 10 ng/ml of TNF-α as inflammatory stimuli for 5 hours, and with 5 drug combinations as follows;
1) no drug without cytokine stimulus (control group)
2) no drug with stimulus (stimulus group)
3) JQ1 with stimulus (J group)
4) Flavopiridol with stimulus (F group)
5) JQ1 and Flavopiridol with stimulus (JF group).
The cells were harvested for RNA extraction.

Quantitative Real-Time RT-PCR.

Total RNA was extracted from the chondrocytes (n=3 donors) using miRNeasy Mini Kit (Qiagen). After the first-strand Cdna was synthesized using Quantitect Reverse Transcription Kit (Qiagen), the converted cDNA samples were amplified in triplicate by a 7900HT real-time PCR system (Applied Biosystems) with gene specific probes and normalized to 18s rRNA.

Microarray Analysis.

Affymetrix GeneChip Human Gene 2.0 ST Array Analysis was performed with total RNA extracted from the chondrocytes (n=2 donors) of 5 groups as described above. First, we selected genes whose expression levels in the stimulus group were 5-fold higher than in the control group, and were repressed by drugs (JQ1, Flavopiridol or both). GeneSpring software identified genes that showed significant difference among the 5 groups by one-way ANOVA. The differentially regulated genes were input into the Ingenuity Pathway Analysis Software to evaluate the changes in canonical pathways.

Figure 3:
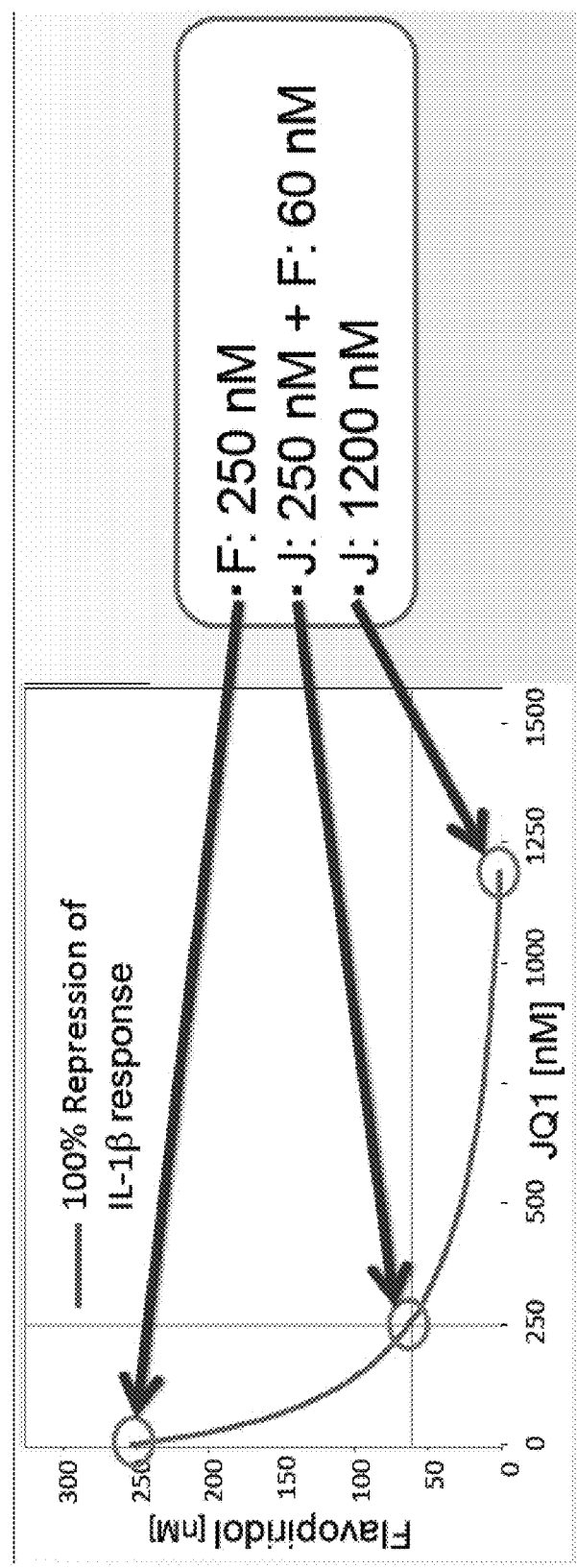
FIG. 3 illustrates determination of the minimal combined dosage for Flavopiridol and JQ1 to achieve complete repression of IL-1β response. The red curve indicates the combined drug dose at which the IL-1β response is completely repressed. Combined treatment reduced the required dosage of Flavopiridol and JQ1 to 60 and 250 nM, about 20-25% of the required dose of each drug individually to achieve 100% repression. Results were generated from healthy human chondrocytes from 4 individual donors, and DOE performed using JMP 11.0 statistical software.
Figure 4:
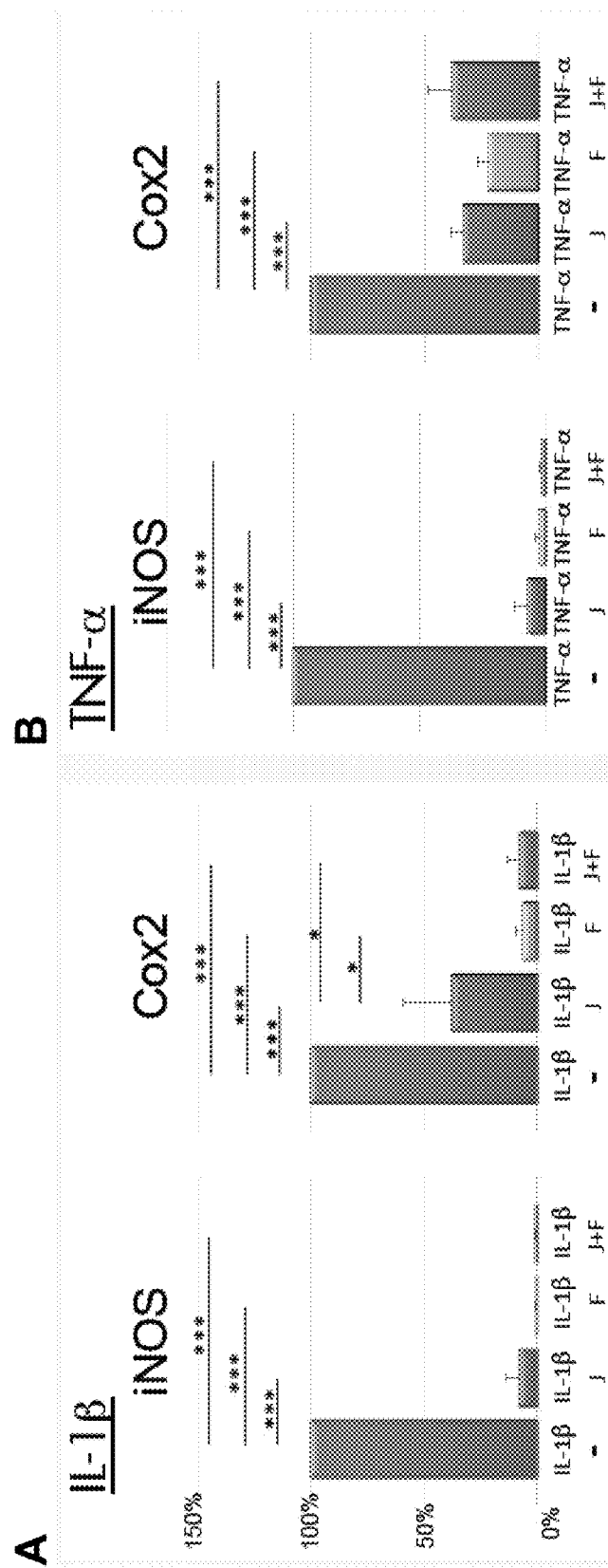
FIGS. 4A-B illustrate CDK9/BRD4 inhibitors repress chondrocyte response to multiple catabolic cytokines. Induction of iNOS and Cox2 by inflammatory cytokines (IL-1β and TNF) requires BRD4 and CDK9 activity. mRNA expression of the cytokine-treated groups were normalized to 100% (blue bars) and compared to groups with cytokine plus CDK9/BRD4 inhibitors (***:$p<0.001$, *:$p<0.05$).

Results are shown in FIGS. 3, 4 and 7. Inhibition of CDK9 and BRD4 with Flavopiridol and JQ1 effectively repressed a panel of pro-inflammatory and catabolic genes. The combination of JQ1 and Flavopiridol showed a synergistic interaction, with similar or better repression of inflammatory response achieved at reduced drug doses (e.g., subtherapeutic or non-efficacious for the individual agents). Brd4 and Cdk9 regulate the transcription of primary response inflammatory genes not only through common mechanisms, but also through independent mechanisms.

Example 2

Transcriptional Control of Trauma-Induced Systemic Inflammatory Response

Inhibition of Cdk9 after knee trauma is highly effective at preventing the local inflammatory response, and is further effective in preventing post-traumatic osteoarthritis (Yik, et al., *Arthritis & Rheumatology* (2014) 66, 1537-1546). The method of treating SIRS and traumatic systemic inflammation is an expansion of our traumatic knee injury studies into other orthopaedic related traumas, such as multiple long bone fractures, that are a major risk factor for systemic inflammation. Systemic inflammation significantly delays fracture healing and increases medical costs (Bastian, et al., *Journal of Leukocyte Biology* (2011) 89, 669-673). Therefore, an effective treatment for SIRS would benefit patients with orthopaedic trauma. As discussed below, our data clearly demonstrate that inhibiting CDK9 alone and concurrently inhibiting Cdk9 and Brd4 effectively suppresses the activation of primary inflammatory response genes resulting from numerous immunological challenges and prevents inflammation induced secondary health effects.

Figure 5C:
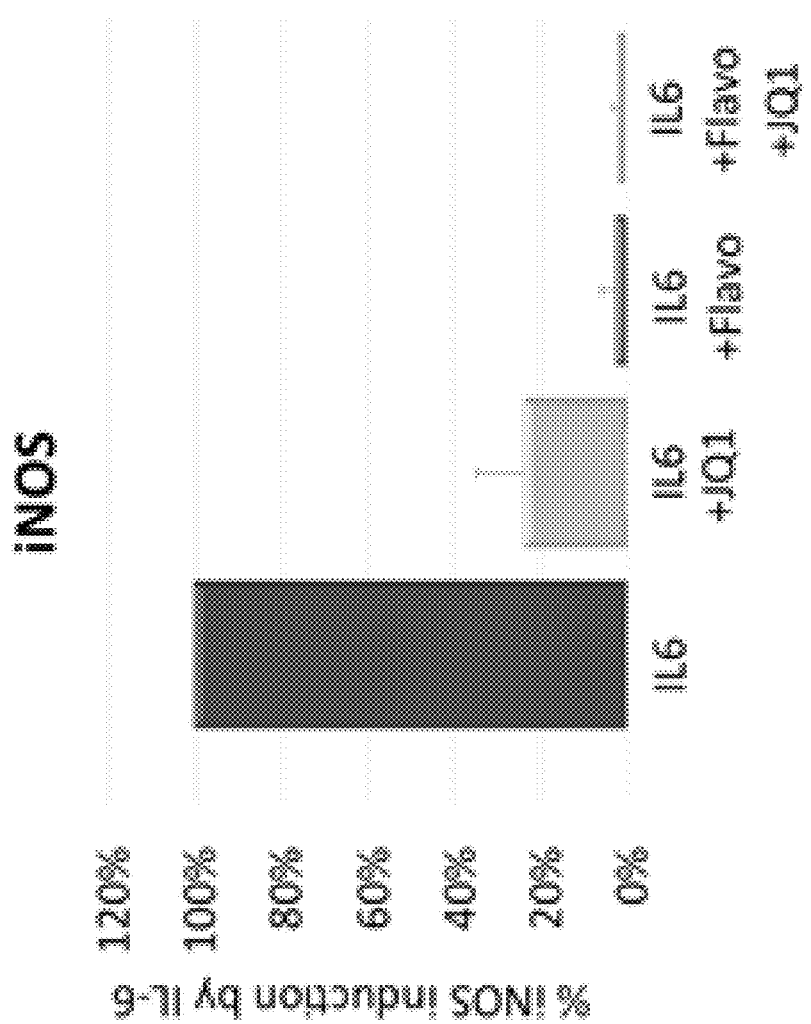

Cdk9 inhibition blocks multiple upstream inflammatory signals. To demonstrate that Cdk9 regulates the common bottle-neck of inflammatory gene activation, human primary chondrocytes were treated separately with four different pro-inflammatory stimuli, IL-1β, lipopolysaccharide (LPS), TNF (in FIG. 5A), or IL-6 (in FIG. 5C), which activate different cell surface receptors and signaling pathways (see FIG. 1). The mRNA induction of the primary inflammatory gene inducible nitric oxide synthase (iNOS) was then determined. The results showed that Cdk9 inhibition by Flavopiridol markedly suppressed iNOS induction by all four inflammatory stimuli (FIGS. 5A & C). Moreover, the observed effects were specifically mediated by Cdk9 because siRNA-mediated knocked down of Cdk9 also prevented iNOS induction by IL-1β treatment (FIG. 5B). Besides iNOS, we have shown that the four stimuli also induced mRNA of other inflammatory cytokines and catabolic genes such as multiple matrix metalloproteases (MMPs), but all the induction was suppressed by Flavopiridol (Yik, et al., *Arthritis & Rheumatology* (2014) 66, 1537-1546). Finally, Cdk9 inhibition prevented IL-6 mRNA induction from cartilage explants subjected to mechanical injuries (FIG. 6A), and the associated apoptosis (FIG. 6B), indicating Cdk9 inhibition protects cartilage from the deleterious effects of inflammation and injuries.

Figure 7A:
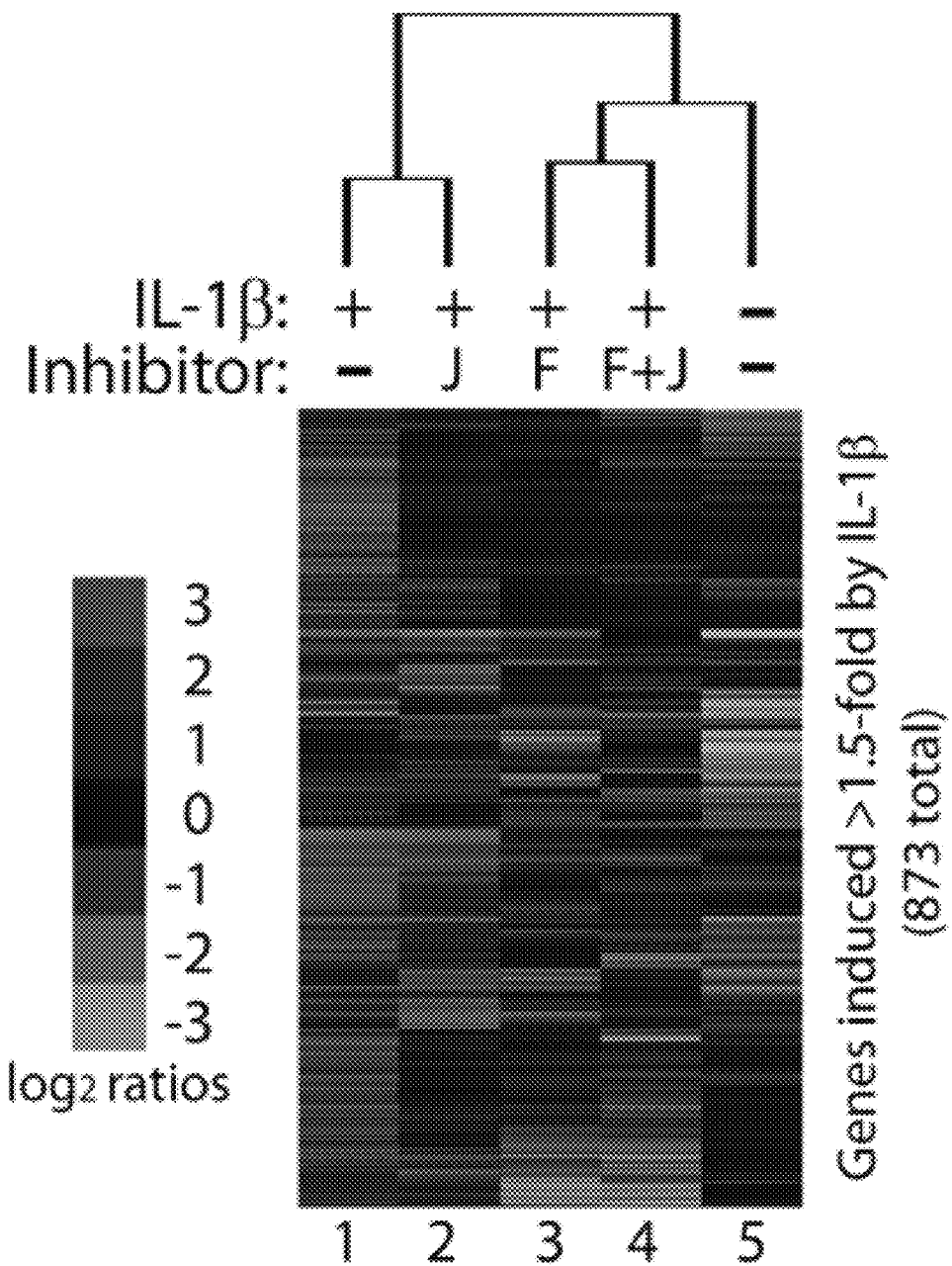
FIGS. 7A-B illustrate that Cdk9 inhibition globally and effectively suppresses activation of downstream primary inflammatory response genes. A) Primary human chondrocytes (n=2) were treated with 10 ng/ml IL-1β, with or without Flavopiridol (F) and/or JQ1 (J) for 5 hours. The entire transcriptomes were analyzed by microarrays (GeneChip Human Gene 2.0 ST Array, Affymetrix). Among the expressed genes, 873 were induced>1.5-fold by IL-1β (compared lanes 1 to 5). The normalized intensities of each of these 873 genes were shown as heat map. Flavopiridol and/or JQ1 treatment suppressed the majority of these genes. B) Highly effective suppression of IL-1β-induced genes by Cdk9 inhibitors. The numbers of inducible genes suppressed by Cdk9 inhibitors were categorized into four quadrants according to the percentage of repression from their maximum induction. Induction of most genes was strongly suppressed by Cdk9 inhibitors. Co-treatment with both Flavopiridol and JQ1 showed a maximal synergistic effect at about 20-25% of the original dosages (250:60 nM), demonstrating the benefits of combined drug treatments in reducing total dosage and potential off-target effects.
Figure 7B:
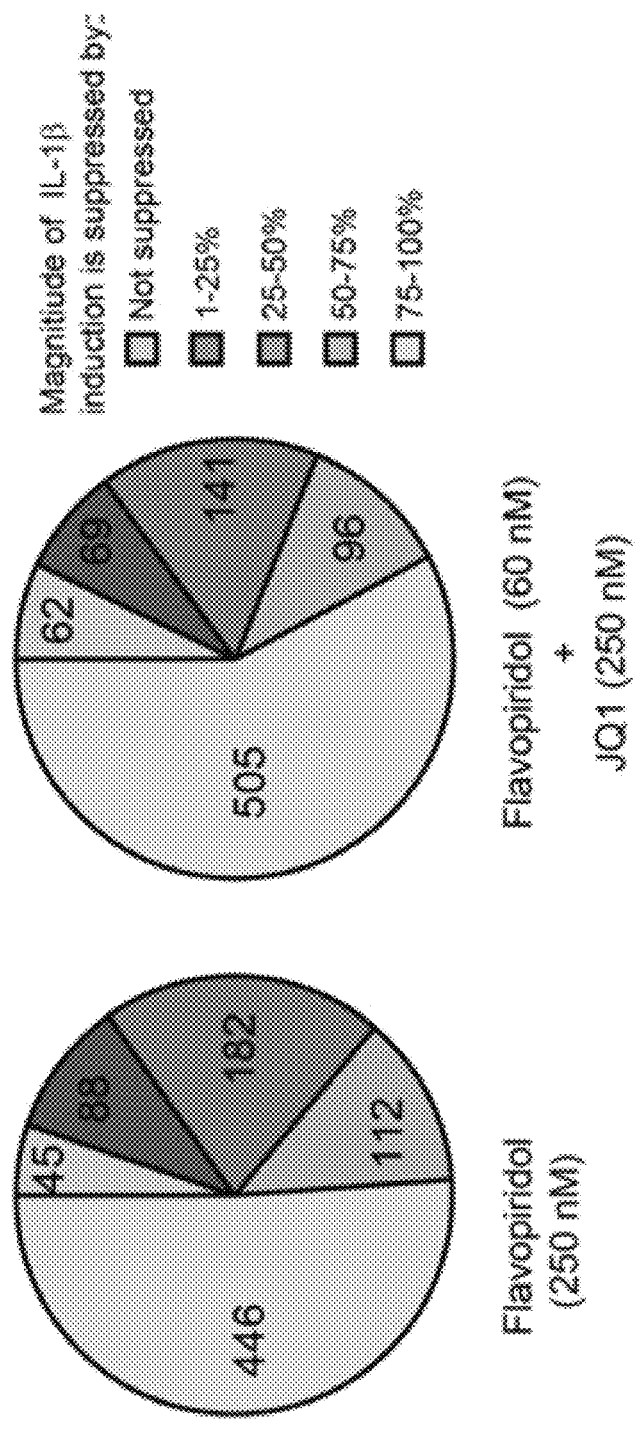
Figure 8A:
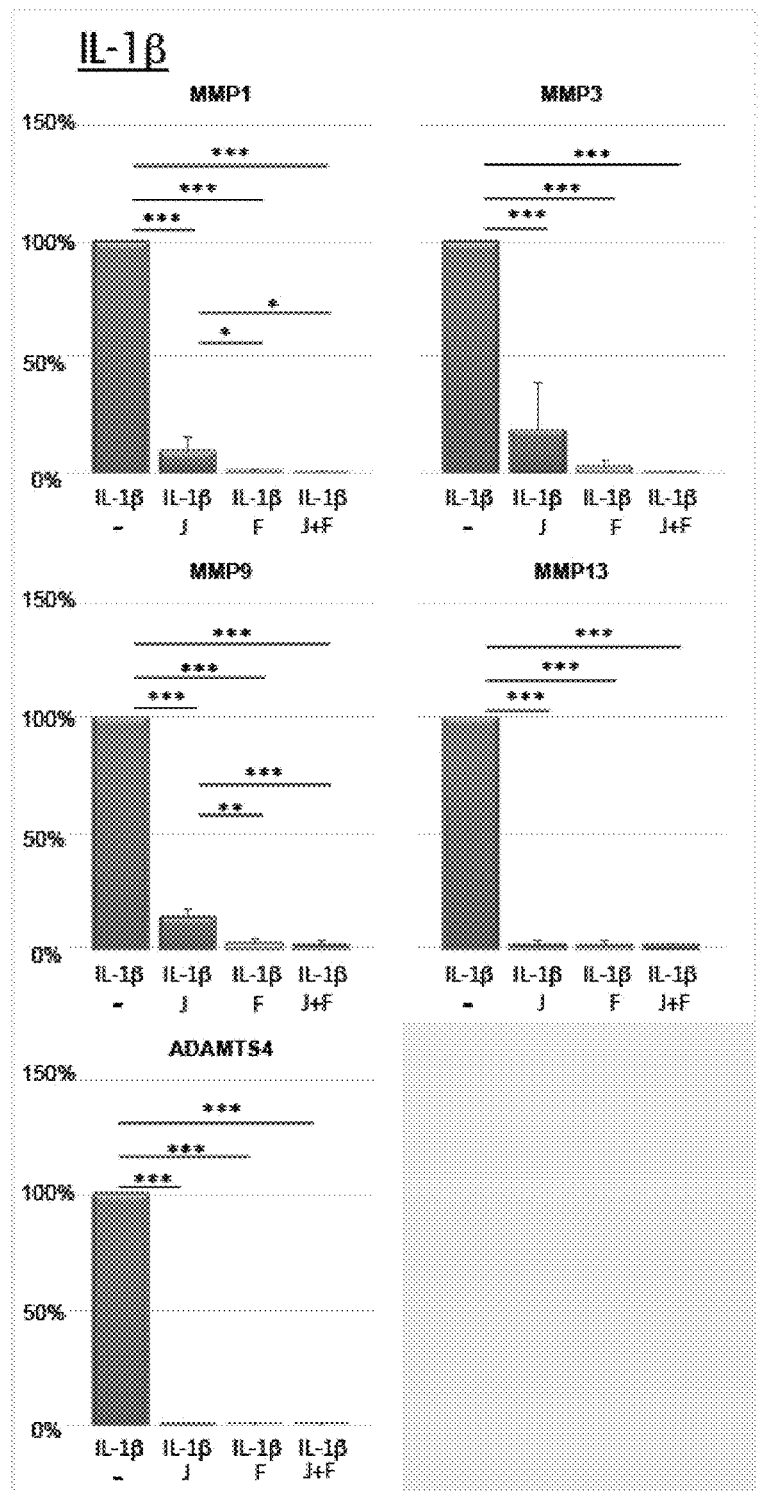
FIGS. 8A-B illustrate Catabolic genes in chondrocytes were repressed by CDK9 and BRD4 inhibitors. Induction of matrix-degrading proteases by inflammatory cytokines requires BRD4 and CDK9 activity. Inhibition of BRD4, CDK9 activity almost completely repressed cytokine-induced expression of MMPs and ADAMTS4.
Figure 8B:
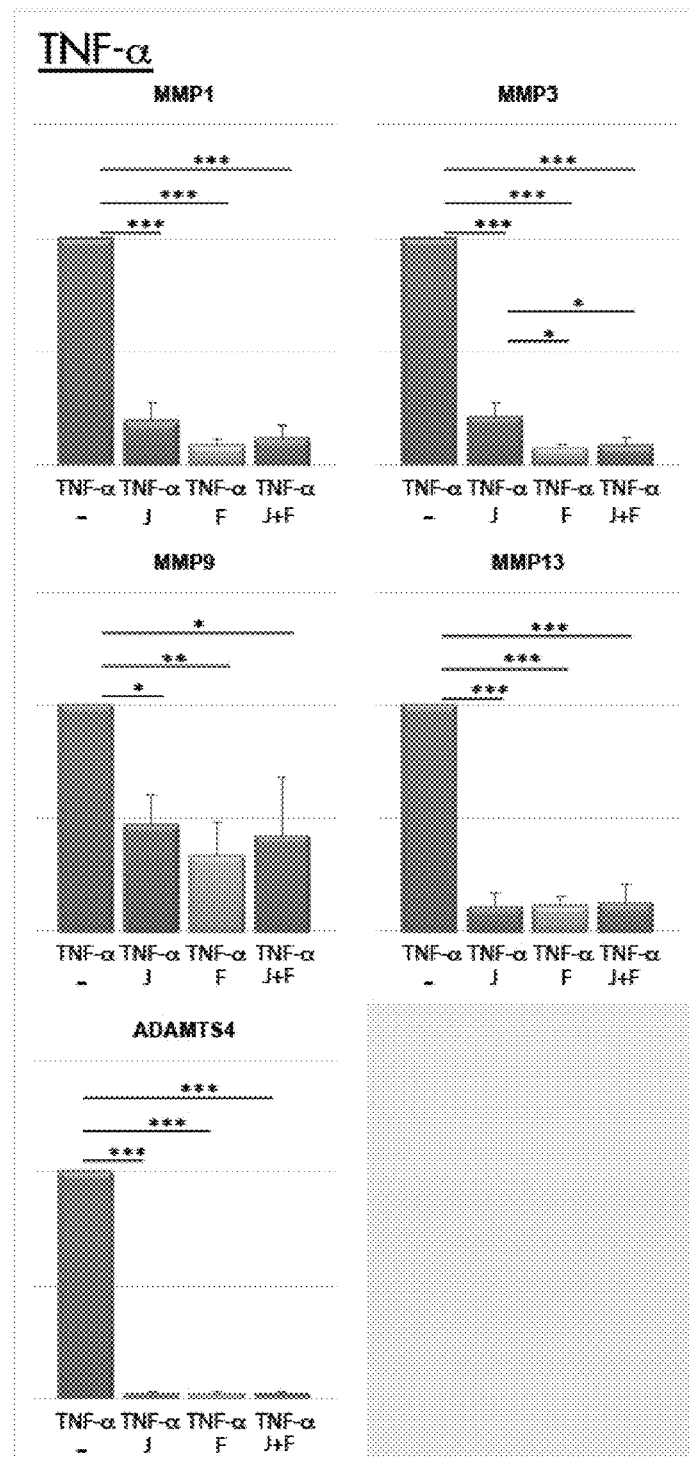

In summary, blocking Cdk9 alone, and concurrently blocking Cdk9 and Brd4, prevents the transcription of inflammatory genes in response to diverse signals including IL-1β, LPS, TNF, IL-6, and mechanical injury. These data confirm the central role of transcriptional activation in stress response, and strongly indicate that this approach would also be successful in blocking SIRS after severe trauma. Cdk9 inhibition effectively suppresses activation of most downstream inflammatory response genes. We next performed microarray screening to demonstrate the effects of Cdk9 inhibition on the activation of a broad spectrum of inflammatory response genes. Primary human chondrocytes in culture were treated with IL-1β as an inflammatory stimulus, in the presence or absence of Flavopiridol and/or JQ1 for 5 hours. Microarrays detected 873 genes within the entire transcriptome that were induced >1.5-fold by IL-1β. Heat map representation of relative gene expression levels showed that JQ1 and Flavopiridol preferentially suppressed a distinct population of these 873 genes (FIG. 7A, compare lanes 2 and 3). A synergistic effect was observed in co-treatment of JQ1 and Flavopiridol at about 20-25% of the original doses, and produced a gene expression profile that most closely resembles untreated samples (FIG. 7A, compare lanes 4 and 5). These data highlight the advantage of the synergistic and complementary effects of using both Flavopiridol and JQ1 for anti-inflammatory therapy Our results also demonstrate the effectiveness and the magnitude of Cdk9 inhibitors in suppressing the induction of primary inflammatory genes. For example, induction of nearly half of the 873 IL-1β-induced genes was suppressed by Flavopiridol to levels that were at least 75% less than their maximum induction values (FIG. 7B, yellow). Only ~5% of the 873 genes were not suppressed at all by Flavopiridol (FIG. 7B, grey). Furthermore, strong synergy was seen between with Flavopiridol and JQ1. Co-treatment with the two drugs achieved better suppression even at a reduced dosages of 60 nM Flavopiridol and 250 nM JQ1 (FIGS. 3 and 7B), when compared to the dosages for single treatments of 250 nM Flavopiridol or 1200 nM JQ1. Reducing the dosages will minimize potential off-target effects. Moreover, our microarray data demonstrated that only inducible genes were affected by Cdk9 inhibition, while the uninduced genes and housekeeping genes were not affected, indicating that Cdk9 inhibition, alone and concurrently with Brd4 inhibition, has minimal off-target effects within the short duration of our experiments. Taken together, the results provided herein and our published data (Yik, et al., *Arthritis & Rheumatology* (2014) 66, 1537-1546) demonstrate the effectiveness of Cdk9 inhibitors, alone and in combination with Brd4 inhibitors, as anti-inflammatory agents that block most inflammatory gene transcription.

Our data herein provide strong evidence that inhibiting Cdk9, alone and in combination with Brd4 inhibition, is a viable anti-inflammatory strategy that sets itself apart from conventional anti-inflammatory agents for the treatment of SIRS. In vitro Cdk9 inhibition not only blocks multiple upstream inflammatory signals, but also suppresses the induction of most downstream inflammatory response genes. Second, in vivo Cdk9 inhibition, alone and concurrently with Brd4 inhibition, reduces tissue inflammation and catabolic responses in our mouse knee injury model. Most importantly, using the LPS-induced systemic inflammation mouse model, we demonstrate that Cdk9 inhibition markedly suppresses plasma levels of the systemic inflammatory marker IL-6. Taken together, these data strongly support that inhibiting Cdk9, alone and in combination with inhibiting Brd4, is a viable strategy to prevent and treat SIRS resulting from severe trauma.

REFERENCES

1. Brandt, K. D.; Dieppe, P.; and Radin, E.: Etiopathogenesis of osteoarthritis. The Medical clinics of North America, 93(1): 1-24, xv, 2009.
2. Anderson, D. D.; Chubinskaya, S.; Guilak, F.; Martin, J. A.; Oegema, T. R.; Olson, S. A.; and Buckwalter, J. A.: Post-traumatic osteoarthritis: Improved understanding and opportunities for early intervention. Journal of orthopaedic research: official publication of the Orthopaedic Research Society, 29(6): 802-9, 2011.
3. Lewis, J. S. et al.: Acute joint pathology and synovial inflammation is associated with increased intra-articular fracture severity in the mouse knee. Osteoarthritis and cartilage/OARS, Osteoarthritis Research Society, 2011.
4. Brown, T. D.; Johnston, R. C.; Saltzman, C. L.; Marsh, J. L.; and Buckwalter, J. A.: Posttraumatic osteoarthritis: a first estimate of incidence, prevalence, and burden of disease. J Orthop Trauma, 20(10): 739-44, 2006.
5. AAOS: http://orthoinfo.aaos.org/topic.cfm?topic=a00297. 2009.
6. Bottoni, C.: Anterior Cruciate Ligament Reconstructions in Active-Duty Military Patients. Operative Techniques in Sports Medicine, 13(3): 169-175, 2005.
7. Lohmander, L. S.; Englund, P. M.; Dahl, L. L.; and Roos, E. M.: The long-term consequence of anterior cruciate ligament and meniscus injuries: osteoarthritis. The American journal of sports medicine, 35(10): 1756-69, 2007.
8. Firestein, G. S., and Kelley, W. N.: Kelley's textbook of rheumatology. Edited, Philadelphia, Pa., Saunders/Elsevier, 2009.
9. Nielsen, A. B., and Yde, J.: Epidemiology of acute knee injuries: a prospective hospital investigation. The Journal of Trauma, 31(12): 1644-8, 1991.
10. Buckwalter, J. A., and Brown, T. D.: Joint injury, repair, and remodeling: roles in post-traumatic osteoarthritis. Clinical Orthopaedics and Related Research, (423): 7-16, 2004.
11. Roos, H.; Adalberth, T.; Dahlberg, L.; and Lohmander, L. S.: Osteoarthritis of the knee after injury to the anterior cruciate ligament or meniscus: the influence of time and age. Osteoarthritis and cartilage/OARS, Osteoarthritis Research Society, 3(4): 261-7, 1995.
12. Felson, D. T.: Osteoarthritis in 2010: New takes on treatment and prevention. Nature reviews. Rheumatology, 7(2): 75-6, 2011.
13. Lotz, M. K.: New developments in osteoarthritis. Post-traumatic osteoarthritis: pathogenesis and pharmacological treatment options. Arthritis Res Ther, 12(3): 211, 2010.
14. Catterall, J. B.; Stabler, T. V.; Flannery, C. R.; and Kraus, V. B.: Changes in serum and synovial fluid biomarkers after acute injury (NCT00332254). Arthritis Research & Therapy, 12(6): R229, 2010.
15. Hargreaves, D. C.; Horng, T.; and Medzhitov, R.: Control of inducible gene expression by signal-dependent transcriptional elongation. Cell, 138(1): 129-45, 2009.
16. Amir-Zilberstein, L.; Ainbinder, E.; Toube, L.; Yamaguchi, Y.; Handa, H.; and Dikstein, R.: Differential regulation of NF-kappaB by elongation factors is determined by core promoter type. Molecular and cellular biology, 27(14): 5246-59, 2007.
17. Brasier, A. R.: Expanding role of cyclin dependent kinases in cytokine inducible gene expression. Cell cycle, 7(17): 2661-6, 2008.
18. Barboric, M.; Nissen, R. M.; Kanazawa, S.; Jabrane-Ferrat, N.; and Peterlin, B. M.: NF-kappaB binds P-TEFb to stimulate transcriptional elongation by RNA polymerase II. Molecular Cell, 8(2): 327-37, 2001.
19. Malumbres, M.; Pevarello, P.; Barbacid, M.; and Bischoff, J. R.: CDK inhibitors in cancer therapy: what is next? Trends in pharmacological sciences, 29(1): 16-21, 2008.
20. Krystof, V., and Uldrijan, S.: Cyclin-dependent kinase inhibitors as anticancer drugs. Current drug targets, 11(3): 291-302, 2010.
21. Zhou, Q., and Yik, J. H.: The Yin and Yang of P-TEFb regulation: implications for human immunodeficiency virus gene expression and global control of cell growth and differentiation. Microbiology and molecular biology reviews: MMBR, 70(3): 646-59, 2006.
22. Rizzolio, F.; Tuccinardi, T.; Caligiuri, I.; Lucchetti, C.; and Giordano, A.: CDK inhibitors: from the bench to clinical trials. Current drug targets, 11(3): 279-90, 2010.
23. Karaman, M. W. et al.: A quantitative analysis of kinase inhibitor selectivity. Nature biotechnology, 26(1): 127-32, 2008.
24. Phelps, M. A. et al.: Clinical response and pharmacokinetics from a phase 1 study of an active dosing schedule of flavopiridol in relapsed chronic lymphocytic leukemia. Blood, 113(12): 2637-45, 2009.
25. Ni, W. et al.: Flavopiridol pharmacogenetics: clinical and functional evidence for the role of SLCO1B1/OATP1B1 in flavopiridol disposition. PLoS ONE, 5(11): e13792, 2010.
26. Byrd, J. C. et al.: Flavopiridol administered using a pharmacologically derived schedule is associated with marked clinical efficacy in refractory, genetically high-risk chronic lymphocytic leukemia. Blood, 109(2): 399-404, 2007.
27. Sekine, C.; Sugihara, T.; Miyake, S.; Hirai, H.; Yoshida, M.; Miyasaka, N.; and Kohsaka, H.: Successful treatment of animal models of rheumatoid arthritis with small-molecule cyclin-dependent kinase inhibitors. Journal of immunology, 180(3): 1954-61, 2008.
28. Glasson, S. S. et al.: Deletion of active ADAMTS5 prevents cartilage degradation in a murinemodel of osteoarthritis. Nature, 434(7033): 644-8, 2005.
29. Kamekura, S. et al.: Osteoarthritis development in novel experimental mouse models induced byknee joint instability. Osteoarthritis and cartilage/OARS, Osteoarthritis Research Society, 13(7): 632-41, 2005.
30. Glasson, S. S.; Blanchet, T. J.; and Morris, E. A.: The surgical destabilization of the medialmeniscus (DMM) model of osteoarthritis in the 129/SvEv mouse. Osteoarthritis and cartilage/OARS, Osteoarthritis Research Society, 15(9): 1061-9, 2007.
31. Poulet, B.; Hamilton, R. W.; Shefelbine, S.; and Pitsillides, A. A.: Characterizing a novel and adjustable non-invasive murine joint loading model. Arthritis & Rheumatism, 63(1): 137-147, 2011.
32. van Osch, G. J.; van der Kraan, P. M.; Blankevoort, L.; Huiskes, R.; and van den Berg, W. B.: Relation of ligament damage with site specific cartilage loss and osteophyte formation incollagenase induced osteoarthritis in mice. The Journal of rheumatology, 23(7): 1227-32, 1996.
33. Joosten, L. A. et al.: Interleukin-18 promotes joint inflammation and induces interleukin-1-driven cartilage destruction. The American journal of pathology, 165(3): 959-67, 2004.
34. Ameye, L. G., and Young, M. F.: Animal models of osteoarthritis: lessons learned while seeking the"'"Holy Grail"'". Curr Opin Rheumatol, 18(5): 537-47, 2006.
35. Dahlberg, L.; Roos, H.; Saxne, T.; Heinegard, D.; Lark, M. W.; Hoerrner, L. A.; and Lohmander, L. S.: Cartilage metabolism in the injured and uninjured knee of the same patient [see comments]. AnnRheum Dis, 53: 823-7, 1994.
36. Glasson, S. S.; Chambers, M. G.; Van Den Berg, W. B.; and Little, C. B.: The OARSI histopathology initiative—recommendations for histological assessments of osteoarthritis in the mouse. Osteoarthritis and cartilage/OARS, Osteoarthritis Research Society, 18 Suppl 3: S17-23, 2010.
37. Aigner, T.; Cook, J. L.; Gerwin, N.; Glasson, S. S.; Laverty, S.; Little, C. B.; McIlwraith, W.; and Kraus, V.

B.: Histopathology atlas of animal model systems—overview of guiding principles. Osteoarthritis and cartilage/OARS, Osteoarthritis Research Society, 18 Suppl 3: S2-6, 2010.

Example 3

Inhibition of CDK9 Prevents Mechanical Injury-Induced Inflammation, Apoptosis, and Matrix Degradation in Cartilage Explants In this example, we examined the therapeutic potential of the CDK9 inhibitor Flavopiridol in a single impact injury model with bovine cartilage explants. The ability of Flavopiridol to prevent the activation of the injury-induced inflammatory and catabolic responses, chondrocytes apoptosis, and cartilage matrix degradation was determined.

Abstract

Joint injury often leads to post-traumatic osteoarthritis (PTOA). Acute injury responses to trauma induce production of pro-inflammatory cytokines and catabolic enzymes, which promote chondrocyte apoptosis and degrade cartilage to potentiate POTA development. Recent studies show that the rate-limiting step for transcriptional activation of injury response genes is controlled by cyclin-dependent kinase 9 (CDK9), and thus it is an attractive target for limiting the injury response. Here we determined the effects of CDK9 inhibition in suppressing the injury response in mechanically-injured cartilage explants. Bovine cartilage explants were injured by a single compressive load of 30% strain at 100%/second, and then treated with the CDK9 inhibitor Flavopiridol. To assess acute injury responses, we measured the mRNA expression of pro-inflammatory cytokines, catabolic enzymes, and apoptotic genes by RT-PCR, and chondrocyte viability and apoptosis by TUNEL staining. For long-term outcome, cartilage matrix degradation was assessed by soluble glycosaminoglycan release, and by determining the mechanical properties with instantaneous and relaxation moduli. Our data showed CDK9 inhibitor markedly reduced injury-induced inflammatory cytokine and catabolic gene expression. CDK9 inhibitor also attenuated chondrocyte apoptosis and reduced cartilage matrix degradation. Lastly, the mechanical properties of the injured explants were preserved by CDK9 inhibitor. Our results provide a temporal profile connecting the chain of events from mechanical impact, acute injury responses, to the subsequent induction of chondrocyte apoptosis and cartilage matrix deterioration. Thus, CDK9 is a potential disease modifying agent for injury response after knee trauma to prevent or delay PTOA development.

Materials and Methods

Cartilage Explants—

Bovine calf (~2 months old, n=40 joints, sex unknown) stifle joints were obtained from a local slaughterhouse (Petaluma, Calif.) within 1 day of slaughtering. 6-8 cylindrical cartilage explants were harvested from each femoral condyle with a 6 mm biopsy punch inserted perpendicular to the weight bearing area of the articular surface. The explants were then trimmed into ~3 mm thickness (with the articular surface intact and the deep layer cut flat) using a custom jig. The explants were washed with phosphate buffered saline and cultured for 24 hours in high-glucose Dulbecco's Modified Eagle's Medium (DMEM) supplemented with 10% fetal bovine serum (Invitrogen), penicillin ($1 \times 10^4$ units/ml) and streptomycin ($1 \times 10^4$ μg/ml) at 37° C., 5% $CO_2$, and 95% relative humidity.

Single Impact Ex-Vivo Injury Model—

After a 24-hours recovery and equilibration period, the cartilage explants were subjected to a single impact mechanical injury. The precise thickness of each individual explant was measured by a caliper before it was placed onto a custom-built unconfined loading chamber, with the articular surface facing upward. A 20 mm diameter stainless steel platen was lowered onto the explant surface to a pre-load of 0.5N (~17.7 kPa) on a hydraulic material testing instrument (Instron 8511.20). All explants including the uninjured controls were subjected to this 0.5N pre-loading step. To avoid potential variation due to the positional differences from where the explants were harvested on the condyles, two adjacent explants were purposefully matched as a control and injured pair for later comparison. After pre-loading, the Instron was programmed to deliver a single compression of 30% strain at 100%/second, followed by immediate release. After the single impact loading, the explant was sliced in half and weighed. One half of the explant was placed in 3 ml media and the other half placed in media containing 300 nM Flavopiridol (Sigma) and cultured for various times (see FIG. 9A). The media was changed every other day with fresh Flavopiridol added. The explants and the culturing media were then subjected to further processing and analysis as described below.

Quantitative Real-Time PCR—

At 2-, 6-, and 24-hours post-injury, the explants were frozen in liquid nitrogen and pulverized with a pestle and mortar while frozen. Total RNA was isolated with the miRNeasy Mini Kit (Qiagen) according to the manufacturer's instruction, with the exception that the RNA was extracted twice with the Qiazol reagents to adequately remove the cartilage matrix constituents. The quantity and quality of the total RNA were determined by a Nanodrop-2000 spectrophotometer. 2.5 ug of total RNA from each sample was used for reverse transcription with the SuperScript First-Strand RT kit (Invitrogen). Individual mRNA expression was determined with quantitative real-time PCR performed in triplicates in a 7900HT system (Applied Biosystem). Results were normalized to the 18s rRNA (catalog no. 4319413E, Applied Biosystem) and calculated as fold-change in mRNA expression relative to control, using the $2^{-\Delta\Delta C_T}$ method. Probes used for individual bovine genes were custom made by Integrated DNA Technologies.

Chondrocyte Viability—

The live and dead cells in the explants 5 days after mechanical injury were stained using a Live/Dead Viability/Cytotoxicity kit (catalog no. L3224, Invitrogen) according to the manufacturer's protocol. The percentages of live and dead cells were determined by counting the cell numbers in 3 random fields of the cross-sectional images of the explants (n=6 for each sample group) captured using a Nikon TE2000 inverted fluorescence microscope and a 20× objective.

Staining for Apoptotic Cells—

After 1, 3, and 5 days after injury, the explants were fixed with 4% paraformaldehyde for 24 hours and transferred to 75% ethanol, followed by sectioning for histological analysis. In situ detection of apoptosis was performed on 5 um-thick whole explant cross-section using the DeadEnd Fluorometric TUNEL system kit (Promega). This kit measures the fragmented DNA of apoptotic cells by catalytically incorporating fluorescein-12-dUTP at 3'-OH DNA ends using the Terminal Deoxynucleotidyl Transferase recombinant enzyme (rTdT). Nuclei were counter stained with DAPI. The sections were mounted and examined under a fluorescence microscope. The percentage of apoptotic cells (n=3 different donors) was determined by counting the number of TUNEL positive cells (green) and calculated as a percentage of the total cells (DAPI). Sections incubated with DNase I were used as positive control while those incubated with buffer only were used as negative control.

GAG Release—

At 5-days post-injury, the culturing media was collected and the amount of glycosylaminoglycan (GAG) was determined by the dimethyl-methylene blue (DMMB) colorimetric assay with chondroitin sulfate as the standard. Total GAG released into the medium was calculated and normalized to the wet weight of the explant (determined at the day of injury).

Cartilage Mechanical Properties—

To test if CDK9 inhibition preserves the mechanical properties of cartilage explants after injury, injured and control explants were cultured for 4 weeks in media with or without Flavopiridol. Cartilage sample compressive properties were assessed by stress-relaxation testing in unconfined compression using a mechanical testing system (Instron 5565, Norwood, Mass.). Prior to testing, a 3 mm diameter, 2 mm thick compression sample was prepared using a dermal biopsy punch, then placed in phosphate buffered saline and centered beneath a 16 mm stainless steel platen. The platen was slowly lowered until a preload of 0.2N was observed, indicating contact between the platen and the cartilage sample. The sample was then preconditioned via fifteen cycles of 5% strain. All strains, including the preconditioning, were applied at a strain rate of 10% per second. Immediately following preconditioning, the sample was subject to 10% compressive strain; the 10% strain was held constant and the load recorded for 380 seconds. At the end of the 10% strain application, the compressive strain was increased to 20% and held constant while the load was recorded for an additional 530 seconds. The compressive properties: instantaneous modulus, relaxation modulus, and coefficient of viscosity, were calculated from the individual stress-relaxation curves using data analysis software (MATLAB R2013a, Natick, Mass.) according to a standard linear solid model of viscoelasticity as previously described (Allen and Athanasiou, 2006). This mechanical test and model were chosen for their simplicity and accuracy in approximating the viscoelastic behavior of cartilage. The compressive properties of freshly isolated (day 0) bovine cartilage explants from 6 donors were determined as baseline values for comparison to 4-weeks post-injury samples.

Statistical Analysis—

Values of all measurements were expressed as the mean+/−standard deviation. Changes in gene expression were analyzed by one-way ANOVA with SPSS 16.0 software. The fold-change in mRNA was used as variables to compare samples between different treatment groups. The least significant difference post-hoc analysis was conducted with a significance level of $P<0.05$.

Changes in compressive properties were analyzed by one-way ANOVA with Tukey's post hoc test using JMP Pro software (version 11.2.0) with a significance level of $P<0.05$.

Results

CDK9 inhibition suppresses injury-induced pro-inflammatory and catabolic genes—CDK9 controls the rate-limiting step of inflammatory gene activation (Hargreaves et al., 2009; Zippo et al., 2009) and we have previously shown that in vitro CDK9 inhibition protects chondrocytes and cartilage from the catabolic effects of exogenously added pro-inflammatory cytokines (Yik et al., 2014). However, the effects of CDK9 inhibition on cartilage that receives a direct impact injury, similar to what may happen in a knee injury, have not been examined. We hypothesize that CDK9 inhibition in mechanically injured cartilage will prevent an inflammatory response, which in turn will reduce the subsequent deleterious effects on chondrocytes and the cartilage matrix. To test our hypothesis, bovine cartilage explants were mechanically injured by subjecting them to an impact loading at a 30% strain rate (FIG. 9A). This magnitude of loading induces chondrocyte apoptosis and cartilage matrix degradation (Borrelli et al., 2003; D'Lima et al., 2001; Hembree et al., 2007; Loening et al., 2000; Morel and Quinn, 2004; Rosenzweig et al., 2012; Waters et al., 2014). The injured explants were cultured in the presence or absence of the CDK9 inhibitor Flavopiridol for various times. The mRNA expression of inflammatory cytokines and catabolic genes induced in the injured explants were determined and compared to uninjured controls. The addition of Flavopiridol reduced the induction of cytokine mRNA by injury (FIGS. 9B&C, grey bars). This effect was most pronounced in the expression of IL-6 mRNA, which was significantly induced by injury at all time points tested (FIG. 9B, open bars), and the IL-6 induction was markedly suppressed by Flavopiridol (FIG. 9B, grey bars). Similar trends were observed for IL-1β (FIG. 9C), although this did not reach statistical significance. These data indicate that as expected, CDK9 inhibition in cartilage explants suppresses inflammatory cytokine induction in response to mechanical injury.

We next examined the injured-induced changes in mRNA expression of the catabolic genes MMP-1 and MMP-13, and ADAMTS4, which are induced by inflammatory cytokines and degrade the cartilage matrix. The results showed that injury induced MMP-1 and ADAMTS4 expression significantly at all time points, and MMP-13 at the 2-hour time point (FIG. 9D-F, open bars). Inhibition of CDK9 effectively prevented the induction of these genes in the injured samples at all time points tested (FIG. 9D-F, grey bars). In contrast, the mRNA expression of the anabolic genes Aggrecan and Col2a1 were not affected by injury whether or not Flavopiridol is present (FIG. 9G-H). Taken together, these results indicate that CDK9 inhibition suppressed injury-induced catabolic mediators of cartilage matrix degradation, while the basal levels of anabolic genes are not affected by injury or CDK9 inhibition at the time points tested.

CDK9 inhibition reduces injury-induced chondrocyte apoptosis—Besides inducing an inflammatory response, mechanical injury also causes chondrocytes apoptosis in cartilage explants (Borrelli et al., 2003; D'Lima et al., 2001; Hembree et al., 2007; Rosenzweig et al., 2012), we therefore investigated the effects of CDK9 inhibition on apoptosis using our explant injury model. The mRNA expression of three selected genes (P53, Bcl-2 and PTEN) that are central to the apoptotic process were examined in the cartilage explants 24-hour post-injury. P53 initiates apoptosis when DNA damage is irreparable (Amaral et al., 2010), Bcl-2 is the founding member of anti-apoptotic factors (Czabotar et al., 2014) and PTEN is a crucial regulator of apoptosis (Zheng et al., 2010). Although mechanical injury itself did not significantly change the mRNA expression of P53, Bcl-2, and PTEN (FIG. 10, open bars), Flavopiridol significantly decreased the expression of these apoptotic mediators in both the injured and uninjured groups (FIG. 10, grey bars).

The reduced basal level of apoptotic mediators has prompted us to directly determine the number of apoptotic chondrocytes in the injured cartilage explants. Cartilage explants from three different donors collected at 1-, 3-, and 5-day post-injury were examined by TUNEL stain and the percentage of apoptotic cells relative to the total number of nuclei in each sample was determined. The results showed that injury increased the percentage of apoptotic chondrocytes to ~20% at 1-day post-injury, and to ~60% 3 days after injury (FIG. 11A). In contrast, CDK9 inhibition significantly reduced the percentage of apoptotic cells in the injured explants in all time points tested (FIG. 11A). These results were further corroborated by the data on live/dead staining of cartilage explants collected 5-day post-injury (FIG. 11B). The live/dead stain showed that injury significantly reduced the number of live chondrocytes from ~80% to ~55% (FIG. 11B, open bars). Flavopiridol treatment enhanced cell survival in the injured explants and did not significantly affect cell survival in uninjured explants (FIG. 11B, grey bars). Taken together, the above results indicate that CDK9 inhibition decreases injury-induced apoptosis in cartilage explants and enhance chondrocyte survival after impact injury.

CDK9 inhibition prevents injury-induced cartilage matrix degradation—Since injury-induced catabolic response leads to upregulation of matrix degrading enzymes, we next investigated if CDK9 inhibition could prevent cartilage matrix degradation after injury. The cartilage explants were continuously cultured for 5 days in the presence or absence of 300 nM Flavopiridol after injury, the culturing media was collected and the GAG content released into the media was determined as a measure of matrix degradation. GAG release was significantly increased upon injury (FIG. 12, open bars); however, in samples treated with Flavopiridol, GAG release by injured cartilage was not increased above the uninjured control baseline. This result indicates that the CDK9 inhibition attenuates mechanical injury-induced cartilage matrix degradation and proteoglycan release.

Figure 13:
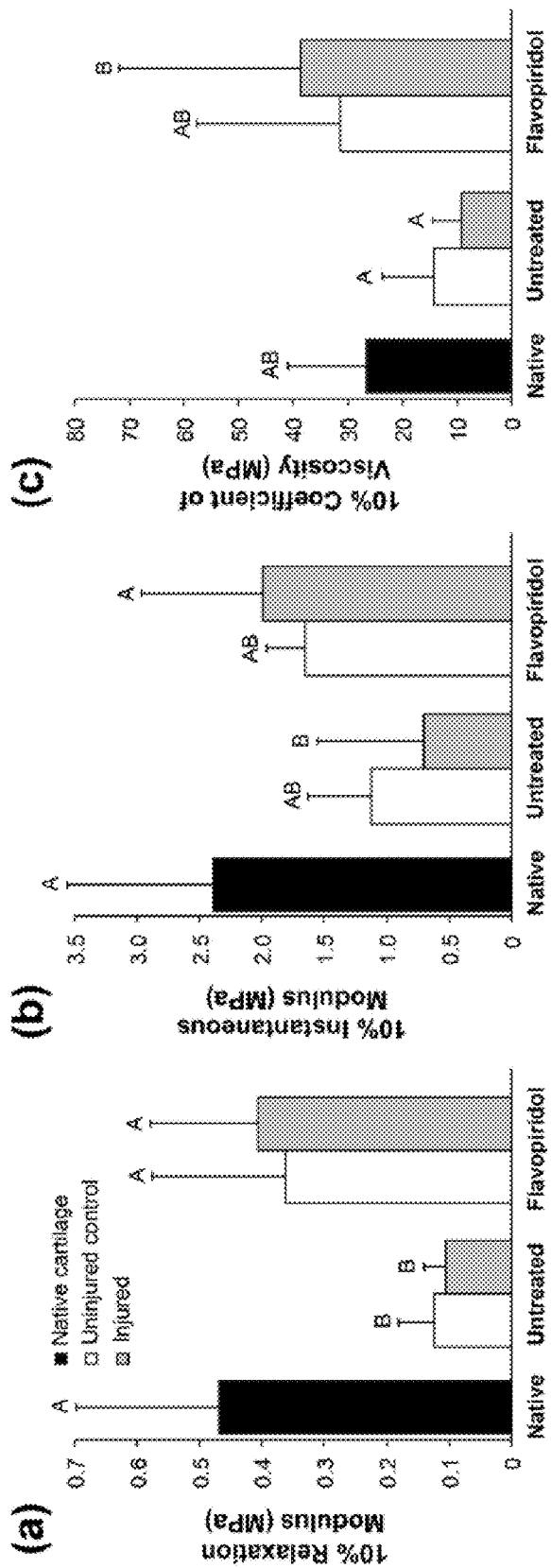
FIGS. 13A-C illustrate that CDK9 inhibition preserves the mechanical properties of injured cartilage. Cartilage explants were cultured for 4 weeks post-injury. The cartilage compressive properties were assessed by stress-relaxation testing in unconfined compression. The 10% relaxation and instantaneous moduli, and coefficient of viscosity are shown. Flavopiridol treatment enhanced the compressive properties of both the injured and uninjured explants. Results were the mean+/−standard deviation obtained from n=6 individual donors. Within each chart, means that do not share a letter are significantly different from each other (P<0.05).
Figure 14:
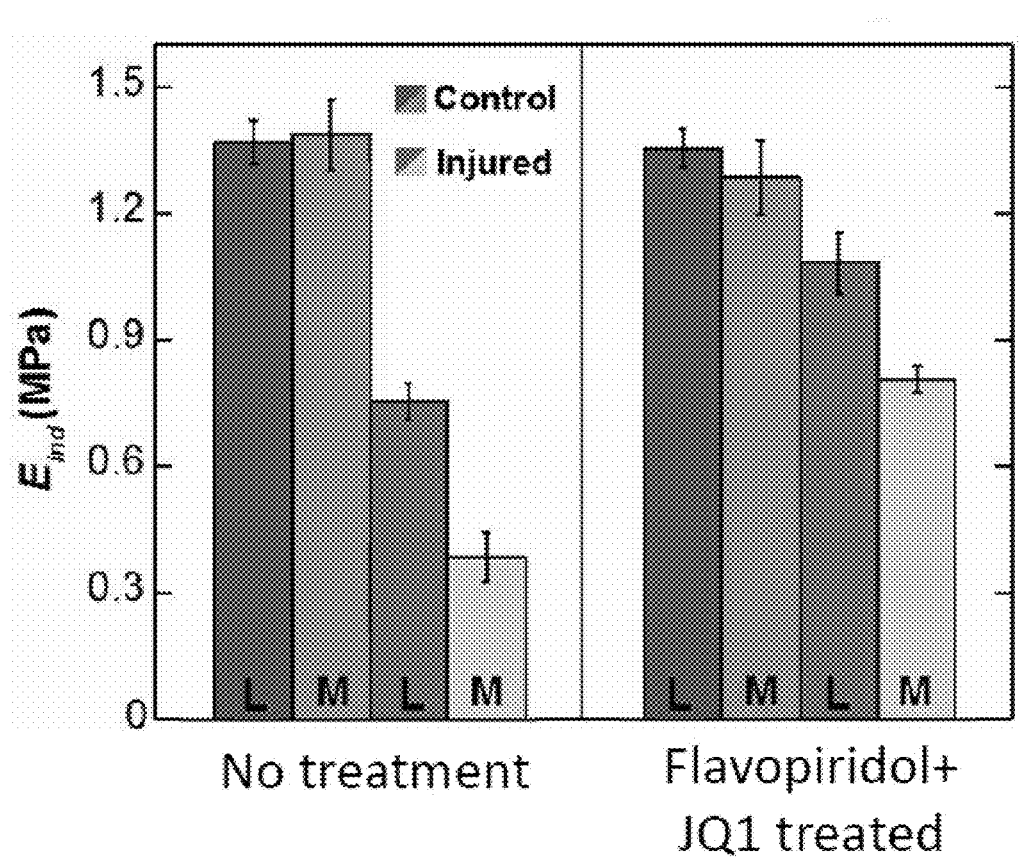
FIG. 14 illustrates that CDK9 inhibition reduces injury-induced loss of cartilage stiffness. Right knees of mice were injured (n=6) as described in Yik, et al., *Arthritis Rheumatol.* (2014) 66(6):1537-46. Left knees served as uninjured controls. Flavopiridol (2.5 mg/kg) and JQ1 (17 mg/kg) were administered daily by intraperitoneal injection for three consecutive days post-injury. At day 7, animal knees were harvested and the cartilage stiffness at the lateral (L) and medial (M) femoral condyles were determined with Atomic Force Microscopy as described (Li et al., *Journal of Biomechanics*. (2015) 48(8):1364-70). Injury induces a loss of cartilage stiffness but the loss is reduced buy the combined drug treatment. Non-invasive mouse models of post-traumatic osteoarthritis are also described in, e.g., Christiansen, et al., *Osteoarthritis Cartilage*. (2015) 23(10):1627-38.

CDK9 inhibition preserves the mechanical properties of cartilage explants after injury—The compressive properties of freshly isolated cartilage were determined from 6 individual donors and their mean values were indicated by the dotted lines in FIG. 13. The compressive properties of the cartilage explants following four weeks of culture demonstrate increased 10% relaxation modulus, 10% instantaneous modulus, and 10% coefficient of viscosity in samples treated with Flavopiridol, when compared to injured, untreated samples (FIG. 13). Similar results were observed for the moduli and coefficients of viscosity calculated from the 20% strain stress-relaxation curves (not shown). The positive effect of Flavopiridol on compressive properties was observed in both injured and uninjured cartilage samples; no significant difference was observed for any compressive property between injured and uninjured cartilage samples when treated with Flavopiridol. Although injured, untreated cartilage samples exhibited the lowest compressive properties among all groups, there was no significant difference between injured and uninjured cartilage samples in the absence of Flavopiridol. Interestingly, cartilage samples treated with Flavopiridol exhibited greater relaxation moduli than untreated, uninjured controls. Furthermore, injured cartilage samples treated with Flavopiridol also have greater instantaneous moduli and coefficients of viscosity than untreated, uninjured controls. These results indicate that Flavopiridol has a beneficial effect on the compressive properties of cartilage samples cultured in vitro.

Discussion

Figure 12:
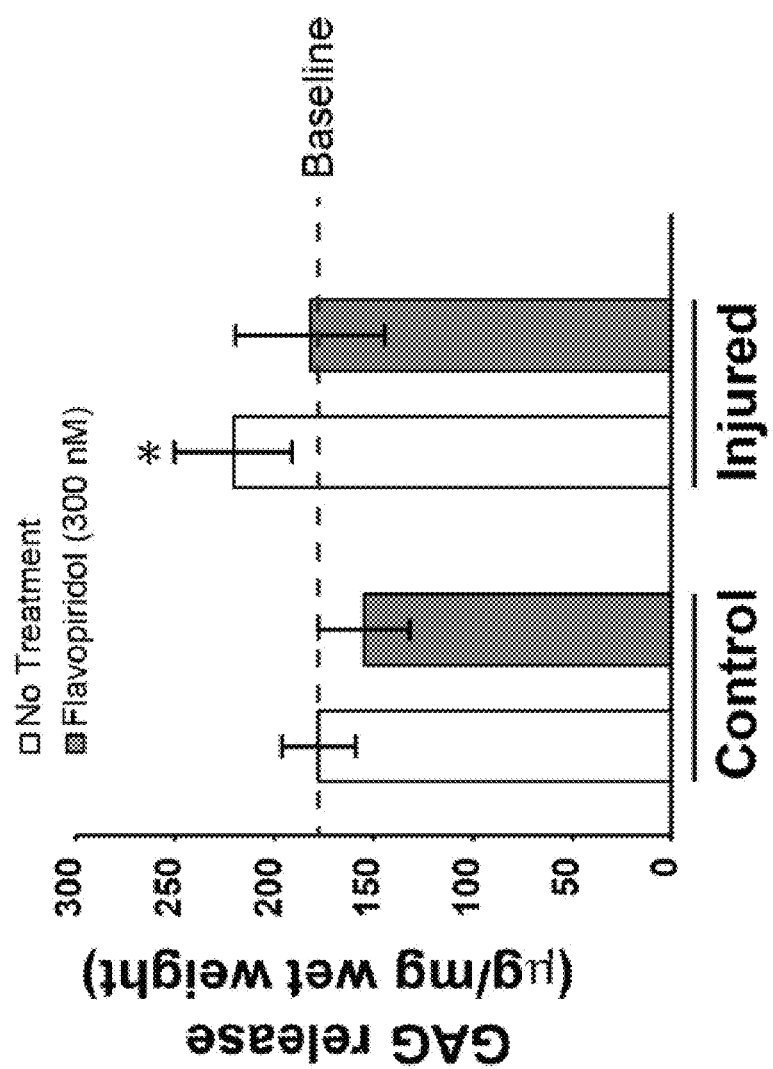
FIG. 12 illustrates that protection of cartilage from injury-induced matrix degradation. Mechanically injured cartilage explants were treated for 5 days with Flavopiridol. The amount of GAG released into the medium was measured by dimethylmethylene blue dye binding assay. Results were normalized to the wet weight of the explants. Injury caused cartilage degradation, as indicated by increased GAG release. In the presence of 300 nM Flavopiridol, levels of GAG release returned to baseline. Results were the mean+/− standard deviation obtained from n=6 individual donors (*p<0.05).

This study examined the effects of CDK9 inhibition on the biological and mechanical properties of cartilage explants after injury by compressive loading. This injury model caused a significant induction of pro-inflammatory cytokines and catabolic enzymes (FIG. 9) within the first 24 hours. Although apoptotic genes were unchanged within this period (FIG. 10), apoptotic chondrocytes could be detected in the explants at 1 day following injury and peaked after 5 days (FIG. 11). Injury also accelerated cartilage matrix degradation as measured by GAG release (FIG. 12). However, CDK9 inhibition by Flavopiridol suppressed all those changes and preserved the mechanical properties similar to those of native cartilage (FIG. 13), thus effectively protecting the chondrocytes and the cartilage from the harmful effects of physical injury and the inflammatory response that follows.

A high incidence of OA is associated with traumatic knee injury and hence the term post-traumatic OA (PTOA). Although the pathology of the development of PTOA from injury remains unclear, several lines of evidence point to the involvement of the inflammatory response in this process. Elevated levels of the inflammatory cytokines IL-1β and IL-6 are detected in the human joints within 24 hours after an ACL injury (Irie et al., 2003). Ko et al demonstrate that inflammation and the accompanying dysregulated cytokines activities likely contribute to the disruption of the balance between anabolism and catabolism in OA (Goldring and Berenbaum, 2004). In vitro and in vivo studies have implicated pro-inflammatory cytokines, particularly IL-1β, in the destruction of articular cartilage in OA (Goldring and Berenbaum, 2004; Kobayashi et al., 2005). In cartilage, chondrocytes are the main target of pro-inflammatory cytokines, which dysregulate the expression of catabolic and anabolic genes. Cytokine-stimulated chondrocytes produce a variety of matrix-degrading enzymes, like MMP-1, -3, -13 and the aggrecanase ADAMTS-4, -5 (Lee et al., 2005; Nishimuta and Levenston, 2012). All these data implicate the involvement of the inflammatory response in cartilage matrix degradation. Our results in this study strongly indicate that CDK9 inhibition prevents induction of inflammatory and catabolic response genes and thus is a novel target for preventing injury-induced damage.

The influences of mechanical injury on chondrocytes anabolic gene expression are still controversial. It has been reported that IL-1β suppresses the expression of Col2a1 in chondrocytes in vitro (Okazaki et al., 2002). However, other OA studies show that in osteoarthritic cartilage, there is enhanced aggrecan and Col2a1 gene expression and biosynthesis, when compared to normal cartilage (Bau et al., 2002; Hermansson et al., 2004). Our results showed no significant change of anabolic gene expression in injured cartilage in the first 24 hours. This is supported by large-scale expression profiling studies use full-thickness cartilage, which demonstrated that many anabolic genes, including Col2a1, are only enhanced in late-stage OA (Aigner et al., 2006; Ijiri et al., 2008). More importantly, our result demonstrates that Flavopiridol has no adverse side effects on anabolic gene expression in the first 24 hours after mechanical injury.

Mechanical injury to cartilage leads to chondrocyte apoptosis. D'Lima et al applied a 30% strain to injure cartilage explants and found 34% apoptotic chondrocytes in 96 hours, compare to only 4% apoptosis in the control group (D'Lima et al., 2001). Similarly, our explant injury model also leads to chondrocyte apoptosis, we detect ~20% apoptotic chondrocytes in 24 hours and more than 60% apoptotic cells after 72 hours (FIG. 11A). Given that injury to cartilage and chondrocyte apoptosis lead to cartilage degradation, the development of drugs designed to block this could be beneficial in preventing PTOA development (Borrelli et al., 2003; D'Lima et al., 2001). For example, when mechanically injured cartilage explants was treated with caspase inhibitors, a 50% reduction of apoptosis was seen (D'Lima et al., 2001). However, few studies have focused on the correlation between the acute injury response within hours, such as induction of inflammatory cytokine and catabolic genes, and the subsequent apoptosis that followed, usually at several days post-injury. Pro-inflammatory cytokines like IL-1β and IL-6 have the capacity to activate a diverse array of intracellular signaling pathways, such as JNK, p38 MAPK and NF-kB (Goldring et al., 2011), and further induce the expression of various pro-apoptotic genes like p53 (Amaral et al., 2010), BCL-2 (Czabotar et al., 2014) and PTEN (Zheng et al., 2010). In chondrocytes, JNK and p38 signaling pathways are thought to be pro-apoptotic in an injury response (Rosenzweig et al., 2012). Results from this study provide a temporal profile connecting the chain of events that happen after mechanical injury to cartilage, from the induction of inflammatory cytokines and catabolic genes, to the subsequent induction of chondrocyte apoptosis. Importantly, Flavopiridol treatment effectively blocks the initial phase of the injury response, and thus prevents subsequent damage to the cartilage.

In contrast to the anti-apoptotic property in this study, Flavopiridol has been reported to induce apoptosis in many cancer cells. Notably, Flavopiridol was originally known for its anti-proliferation properties by suppressing cell-cycle progression in rapidly dividing cells (e.g. cancers) (Wang and Ren, 2010). This is due to the off-target suppressive effect of Flavopiridol on other CDKs that directly regulate cell-cycle. We believe that mature chondrocytes, which do not normally divide (Kobayashi et al., 2005), are therefore less sensitive to the anti-proliferative effect of Flavopiridol.

Flavopiridol has a beneficial effect on the compressive, viscoelastic properties of injured cartilage explants after four weeks of culture. Specifically, both injured and uninjured cartilage samples treated with Flavopiridol have increased stiffness upon initial compression (instantaneous modulus) and upon reaching equilibrium during prolonged static compression (relaxation modulus) compared to injured-untreated samples. The increased instantaneous and relaxation moduli are likely associated with preservation of glycosaminoglycans (GAG) in the cartilage extracellular matrix (ECM) and of the elastic stiffness of the ECM, respectively. Furthermore, injured samples treated with Flavopiridol exhibit a slower rate of relaxation toward equilibrium following compression compared to injured-untreated samples as evidenced by a greater coefficient of viscosity in the treated samples. An increased coefficient of viscosity is likely associated with retention of GAG in the ECM, which resists movement of water out of cartilage during compression. Overall, treatment with Flavopiridol helps maintain the viscoelastic, compressive properties of cultured cartilage samples close to values observed for uncultured native cartilage samples (FIG. 13). Flavopiridol may preserve cartilage mechanical properties in vivo following injury as well as in vitro during culture.

The lack of difference in the mechanical properties between injured cartilage explants and uninjured control explants was an unexpected finding of this study. Although the injured explants cultured without Flavopiridol had the lowest instantaneous modulus and coefficient of viscosity among all treatment groups, the difference between injured and uninjured samples was not statistically significant ($P>0.05$). Cartilage degradation and loss of GAG known to occur during prolonged culture of immature cartilage (Bian et al., 2010) may have caused the loss of cartilage compressive properties observed in the untreated-uninjured cartilage explants. We suspect that testing samples after shorter culture duration may demonstrate a greater difference between the injured and uninjured cartilage.

In summary, out data for the first time demonstrated the effectiveness of CDK9 inhibition in the suppression of pro-inflammatory cytokine induced by mechanical injury and prevention of chondrocyte apoptosis in cartilage explants. In addition, our data strongly indicate that Flavopiridol is an effective agent to prevent cartilage matrix degradation and to preserve its mechanical properties after injury. Thus CDK9 inhibition by Flavopiridol provides an effective strategy to prevent or delay PTOA after knee joint trauma.

References for Example 3

Aigner T, Fundel K, Saas J, Gebhard P M, Haag J, Weiss T, Zien A, Obermayr F, Zimmer R, Bartnik E (2006) Large-scale gene expression profiling reveals major pathogenetic pathways of cartilage degeneration in osteoarthritis. Arthritis Rheum 54: 3533-3544.

Allen K D, Athanasiou K A (2006) Viscoelastic characterization of the porcine temporomandibular joint disc under unconfined compression. J Biomech 39: 312-322.

Amaral J D, Xavier J M, Steer C J, Rodrigues C M (2010) The role of p53 in apoptosis. Discov Med 9: 145-152.

Bau B, Haag J, Schmid E, Kaiser M, Gebhard P M, Aigner T (2002) Bone morphogenetic protein-mediating receptor-associated Smads as well as common Smad are expressed in human articular chondrocytes but not up-regulated or down-regulated in osteoarthritic cartilage. J Bone Miner Res 17: 2141-2150.

Bian L, Stoker A M, Marberry K M, Ateshian G A, Cook J L, Hung C T (2010) Effects of dexamethasone on the functional properties of cartilage explants during long-term culture. Am J Sports Med 38: 78-85.

Blumberg T J, Natoli R M, Athanasiou K A (2008) Effects of doxycycline on articular cartilage GAG release and mechanical properties following impact. Biotechnol Bioeng 100: 506-515.

Borrelli J, Jr., Tinsley K, Ricci W M, Burns M, Karl I E, Hotchkiss R (2003) Induction of chondrocyte apoptosis following impact load. J Orthop Trauma 17: 635-641.

Christiansen B A, Anderson M J, Lee C A, Williams J C, Yik J H, Haudenschild D R (2012) Musculoskeletal changes following non-invasive knee injury using a novel mouse model of post-traumatic osteoarthritis. Osteoarthritis Cartilage 20: 773-782.

Czabotar P E, Lessene G, Strasser A, Adams J M (2014) Control of apoptosis by the BCL-2 protein family: implications for physiology and therapy. Nat Rev Mol Cell Biol 15: 49-63.

D'Lima D D, Hashimoto S, Chen P C, Colwell C W, Jr., Lotz M K (2001) Human chondrocyte apoptosis in response to mechanical injury. Osteoarthritis Cartilage 9: 712-719.

Fowler T, Sen R, Roy A L (2011) Regulation of primary response genes. Mol Cell 44: 348-360.

Goldring M B, Berenbaum F (2004) The regulation of chondrocyte function by proinflammatory mediators: prostaglandins and nitric oxide. Clin Orthop Relat Res: S37-46.

Goldring M B, Otero M, Plumb D A, Dragomir C, Favero M, El Hachem K, Hashimoto K, Roach H I, Olivotto E, Borzi R M, Marcu K B (2011) Roles of inflammatory and anabolic cytokines in cartilage metabolism: signals and multiple effectors converge upon MMP-13 regulation in osteoarthritis. Eur Cell Mater 21: 202-220.

Guilak F, Fermor B, Keefe F J, Kraus V B, Olson S A, Pisetsky D S, Setton L A, Weinberg J B (2004) The role of biomechanics and inflammation in cartilage injury and repair. Clin Orthop Relat Res: 17-26.

Hargreaves D C, Horng T, Medzhitov R (2009) Control of inducible gene expression by signal-dependent transcriptional elongation. Cell 138: 129-145.

Hembree W C, Ward B D, Furman B D, Zura R D, Nichols L A, Guilak F, Olson S A (2007) Viability and apoptosis of human chondrocytes in osteochondral fragments following joint trauma. J Bone Joint Surg Br 89: 1388-1395.

Hermansson M, Sawaji Y, Bolton M, Alexander S, Wallace A, Begum S, Wait R, Saklatvala J (2004) Proteomic analysis of articular cartilage shows increased type II collagen synthesis in osteoarthritis and expression of inhibin betaA (activin A), a regulatory molecule for chondrocytes. J Biol Chem 279: 43514-43521.

Ijiri K, Zerbini L F, Peng H, Otu H H, Tsuchimochi K, Otero M, Dragomir C, Walsh N, Bierbaum B E, Mattingly D, van Flandern G, Komiya S, Aigner T, Libermann T A, Goldring M B (2008) Differential expression of GADD45beta in normal and osteoarthritic cartilage: potential role in homeostasis of articular chondrocytes. Arthritis Rheum 58: 2075-2087.

Imgenberg J, Rolauffs B, Grodzinsky A J, Schunke M, Kurz B (2013) Estrogen reduces mechanical injury-related cell death and proteoglycan degradation in mature articular cartilage independent of the presence of the superficial zone tissue. Osteoarthritis Cartilage 21: 1738-1745.

Irie K, Uchiyama E, Iwaso H (2003) Intraarticular inflammatory cytokines in acute anterior cruciate ligament injured knee. Knee 10: 93-96.

Ko F C, Dragomir C, Plumb D A, Goldring S R, Wright T M, Goldring M B, van der Meulen M C (2013) In vivo cyclic compression causes cartilage degeneration and subchondral bone changes in mouse tibiae. Arthritis Rheum 65: 1569-1578.

Kobayashi M, Squires G R, Mousa A, Tanzer M, Zukor D J, Antoniou J, Feige U, Poole A R (2005) Role of interleukin-1 and tumor necrosis factor alpha in matrix degradation of human osteoarthritic cartilage. Arthritis Rheum 52: 128-135.

Lee J H, Fitzgerald J B, Dimicco M A, Grodzinsky A J (2005) Mechanical injury of cartilage explants causes specific time-dependent changes in chondrocyte gene expression. Arthritis Rheum 52: 2386-2395.

Lockwood K A, Chu B T, Anderson M J, Haudenschild D R, Christiansen B A (2014) Comparison of loading rate-dependent injury modes in a murine model of post-traumatic osteoarthritis. J Orthop Res 32: 79-88.

Loening A M, James I E, Levenston M E, Badger A M, Frank E H, Kurz B, Nuttall M E, Hung H H, Blake S M, Grodzinsky A J, Lark M W (2000) Injurious mechanical compression of bovine articular cartilage induces chondrocyte apoptosis. Arch Biochem Biophys 381: 205-212.

Lohmander L S, Englund P M, Dahl L L, Roos E M (2007) The long-term consequence of anterior cruciate ligament and meniscus injuries: osteoarthritis. Am J Sports Med 35: 1756-1769.

Morel V, Quinn T M (2004) Cartilage injury by ramp compression near the gel diffusion rate. J Orthop Res 22: 145-151.

Murray M M, Zurakowski D, Vrahas M S (2004) The death of articular chondrocytes after intra-articular fracture in humans. J Trauma 56: 128-131.

Nishimuta J F, Levenston M E (2012) Response of cartilage and meniscus tissue explants to in vitro compressive overload. Osteoarthritis Cartilage 20: 422-429.

Okazaki K, Li J, Yu H, Fukui N, Sandell L J (2002) CCAAT/enhancer-binding proteins beta and delta mediate the repression of gene transcription of cartilage-derived retinoic acid-sensitive protein induced by interleukin-1 beta. J Biol Chem 277: 31526-31533.

Rosenzweig D H, Djap M J, Ou S J, Quinn T M (2012) Mechanical injury of bovine cartilage explants induces depth-dependent, transient changes in MAP kinase activity associated with apoptosis. Osteoarthritis Cartilage 20: 1591-1602.

Wang L M, Ren D M (2010) Flavopiridol, the first cyclin-dependent kinase inhibitor: recent advances in combination chemotherapy. Mini Rev Med Chem 10: 1058-1070.

Waters N P, Stoker A M, Carson W L, Pfeiffer F M, Cook J L (2014) Biomarkers affected by impact velocity and maximum strain of cartilage during injury. J Biomech 47: 3185-3195.

Yik J H, Hu Z, Kumari R, Christiansen B A, Haudenschild D R (2014) Cyclin-dependent kinase 9 inhibition protects cartilage from the catabolic effects of proinflammatory cytokines. Arthritis Rheumatol 66: 1537-1546.

Zheng T, Meng X, Wang J, Chen X, Yin D, Liang Y, Song X, Pan S, Jiang H, Liu L (2010) PTEN- and p53-mediated apoptosis and cell cycle arrest by FTY720 in gastric cancer cells and nude mice. Journal of Cellular Biochemistry 111: 218-228.

Zhou Q, Yik JH (2006) The Yin and Yang of P-TEFb regulation: implications for human immunodeficiency virus gene expression and global control of cell growth and differentiation. Microbiol Mol Biol Rev 70: 646-659.

Zippo A, Serafini R, Rocchigiani M, Pennacchini S, Krepelova A, Oliviero S (2009) Histone crosstalk between H3S10ph and H4K16ac generates a histone code that mediates transcription elongation. Cell 138: 1122-1136.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of reducing, inhibiting, mitigating and/or ameliorating cartilage degradation and/or chondrocyte death in a subject in need thereof, comprising co-administering to the subject an effective amount of an inhibitor of cyclin-dependent kinase 9 (CDK9) and an inhibitor of bromodomain containing protein 4 (BRD4), thereby reducing, inhibiting, mitigating and/or ameliorating cartilage degradation and/or chondrocyte death in the subject, wherein the CDK9 inhibitor and the BRD4 inhibitor are initially co-administered within about 10 day after experiencing traumatic injury.

2. The method of claim 1, wherein the subject has experienced a traumatic injury to cartilage tissue.

3. The method of claim 2, wherein the subject has undergone joint surgery.

4. The method of claim 1, wherein one or both of the inhibitor of CDK9 and the inhibitor of BRD4 are initially co-administered during the acute response phase and reduce and/or inhibit transcriptional activation of one or more primary response genes after experiencing traumatic injury.

5. The method of claim 4, wherein the one or more primary response genes are selected from the group consisting of IL-1β, inducible nitric oxide synthase (iNOS), IL-6, TNF-α, MMP-1, MMP-3, MMP-9, MMP-13 and ADAMTS4 (aggrecanase).

6. The method of claim 1, wherein one or both of the inhibitor of CDK9 and the inhibitor of BRD4 are initially co-administered within about 72 hours after experiencing traumatic injury.

7. The method of claim 1, wherein one or both of the inhibitor of CDK9 and the inhibitor of BRD4 are administered over a course of 10 days.

8. The method of claim 1, wherein one or both of the inhibitor of CDK9 and the inhibitor of BRD4 are administered multiple times.

9. The method of claim 1, wherein the subject has undergone surgery to repair damaged cartilage tissue.

10. The method of claim 1, wherein the subject has received an osteochondral explant.

11. The method of claim 10, wherein the osteochondral explant is a cartilage allograft.

12. The method of claim 1, wherein one or both of the inhibitor of CDK9 and the inhibitor of BRD4 are co-administered concurrently with or prior to surgery.

13. The method of claim 1, wherein one or both of the inhibitor of CDK9 and the inhibitor of BRD4 are co-administered within 24 hours after surgery.

14. The method of claim 1, wherein one or both of the inhibitor of CDK9 and the inhibitor of BRD4 are co-administered systemically.

15. The method of claim 14, wherein one or both of the inhibitor of CDK9 and the inhibitor of BRD4 are co-administered intravenously.

16. The method of claim 1, wherein one or both of the inhibitor of CDK9 and the inhibitor of BRD4 are co-administered directly to the site of injured cartilage tissue.

17. The method of claim 16, wherein one or both of the inhibitor of CDK9 and the inhibitor of BRD4 are delivered from a matrix.

18. The method of claim 1, wherein the inhibitor of CDK9 is a small organic compound.

19. The method of claim 18, wherein the inhibitor of CDK9 is flavopiridol.

20. The method of claim 1, wherein the inhibitor of BRD4 is a small organic compound.

21. The method of claim 20, wherein the inhibitor of BRD4 is selected from the group consisting of JQ1 (CAS Number 1268524-70-4) and GSK525762A (CAS Number 1260907-17-2).

22. The method of claim 1, wherein one or both of the inhibitor of CDK9 and the inhibitor of BRD4 are administered at a subtherapeutic or non-efficacious dose for the individual inhibitors.

23. A method of reducing, inhibiting, mitigating and/or ameliorating the onset and/or progression of post-traumatic osteoarthritis in a subject in need thereof, comprising co-administering to the subject an effective amount of an inhibitor of cyclin-dependent kinase 9 (CDK9) and an inhibitor of bromodomain containing protein 4 (BRD4), thereby reducing, inhibiting, mitigating and/or ameliorating post-traumatic osteoarthritis in the subject, wherein the CDK9 inhibitor and the BRD4 inhibitor are initially co-administered within about 10 days after experiencing traumatic injury.

24. A method of reducing, inhibiting, mitigating and/or ameliorating severe polytrauma or systemic inflammatory response syndrome (SIRS) in a subject in need thereof, comprising administering to the subject an effective amount of an inhibitor of cyclin-dependent kinase 9 (CDK9) and an inhibitor of bromodomain containing protein 4 (BRD4), thereby reducing, inhibiting, mitigating and/or ameliorating severe polytrauma or systemic inflammatory response syndrome (SIRS) in the subject, wherein the CDK9 inhibitor and the BRD4 inhibitor are initially co-administered within about 10 days after experiencing traumatic injury.

25. A method of reducing, inhibiting, mitigating and/or ameliorating severe polytrauma or systemic inflammatory response syndrome (SIRS) in a subject in need thereof, comprising co-administering to the subject an effective amount of an inhibitor of cyclin-dependent kinase 9 (CDK9) and an inhibitor of bromodomain containing protein 4 (BRD4), thereby reducing, inhibiting, mitigating and/or ameliorating severe polytrauma or systemic inflammatory response syndrome (SIRS) in the subject, wherein the CDK9 inhibitor and the BRD4 inhibitor are initially co-administered within about 10 days after experiencing traumatic injury.

26. A method of reducing, or inhibiting degradation of an osteochondral explant and/or reducing, preventing or inhibiting chondrocyte death during storage, comprising storing the osteochondral explant and/or chondrocytes in a solution comprising an inhibitor of cyclin-dependent kinase 9 (CDK9) and an inhibitor of bromodomain containing protein 4 (BRD4).

27. A composition comprising an osteochondral explant in a solution comprising an inhibitor of cyclin-dependent kinase 9 (CDK9) and an inhibitor of bromodomain containing protein 4 (BRD4).

\* \* \* \* \*